US010941389B2

(12) United States Patent
Jaeckel et al.

(10) Patent No.: US 10,941,389 B2
(45) Date of Patent: *Mar. 9, 2021

(54) VARIANTS OF CHYMOSIN WITH IMPROVED PROPERTIES

(71) Applicant: Chr. Hansen A/S, Hoersholm (DK)

(72) Inventors: Christian Jaeckel, Vaerloese (DK); Martin Lund, Copenhagen Ø (DK); Enikö Fodor Hansen, Helsingoer (DK); Lone Riisberg, Nivaa (DK); Iben Jeppesen, Alleroed (DK); Johannes Maarten Van Den Brink, Herlev (DK)

(73) Assignee: CHR. HANSEN A/S, Hoersholm (DK)

( * ) Notice: Subject to any disclaimer, the term of this patent is extended or adjusted under 35 U.S.C. 154(b) by 15 days.

This patent is subject to a terminal disclaimer.

(21) Appl. No.: 15/755,044

(22) PCT Filed: Aug. 31, 2016

(86) PCT No.: PCT/EP2016/070468
§ 371 (c)(1),
(2) Date: Feb. 23, 2018

(87) PCT Pub. No.: WO2017/037092
PCT Pub. Date: Mar. 9, 2017

(65) Prior Publication Data
US 2018/0251747 A1 Sep. 6, 2018

(30) Foreign Application Priority Data

Aug. 31, 2015 (EP) .................................... 15183205

(51) Int. Cl.
| C12N 9/20 | (2006.01) |
| C12N 15/00 | (2006.01) |
| C12N 9/64 | (2006.01) |

(52) U.S. Cl.
CPC ........... *C12N 9/6483* (2013.01); *C12N 15/00* (2013.01); *C12Y 304/23004* (2013.01)

(58) Field of Classification Search
CPC .................................................. C12N 9/6483
See application file for complete search history.

(56) References Cited

U.S. PATENT DOCUMENTS

| 7,390,936 B1 | 6/2008 | Rooijen et al. |
| 7,482,148 B2 | 1/2009 | Mule et al. |
| 9,930,899 B2 | 4/2018 | Van Den Brink et al. |
| 10,167,463 B2 * | 1/2019 | Dekker .......... C12Y 304/23004 |
| 2008/0226768 A1 | 9/2008 | Kappeler et al. |
| 2011/0287137 A1 | 11/2011 | Kappeler et al. |
| 2015/0140169 A1 * | 5/2015 | Dekker .......... C12Y 304/23004 426/36 |
| 2017/0067041 A1 | 3/2017 | Van Den Brink et al. |
| 2018/0110234 A1 | 4/2018 | Faiveley et al. |
| 2018/0317510 A1 | 11/2018 | Van Den Brink et al. |

FOREIGN PATENT DOCUMENTS

| EP | 0 123 928 A2 | 11/1984 |
| JP | 2010-046034 A | 3/2010 |
| RU | 2 192 137 C2 | 11/2002 |
| WO | WO 02/36752 A2 | 5/2002 |
| WO | WO 2004/031733 A2 | 4/2004 |
| WO | WO 2005/003345 A2 | 1/2005 |
| WO | WO 2008/098973 A1 | 8/2008 |
| WO | WO 2010/110464 A1 | 9/2010 |
| WO | WO-2013/164479 A2 | 11/2013 |
| WO | WO-2013/164481 A1 | 11/2013 |
| WO | WO-2013/174840 A1 | 11/2013 |
| WO | WO-2015/128417 A1 | 9/2015 |
| WO | WO-2017/037092 A1 | 3/2017 |

OTHER PUBLICATIONS

Studer. Residue mutations and their impact on protein structure and function: detecting beneficial and pathogenic changes. Biochem. J. (2013) 449, 581-594.—form PTO-892*

Bansal et al., "Suitability of recombinant camel (*Camelus dromedarius*) chymosin as a coagulant for Cheddar cheese", International Diary Journal (Mar. 2009) vol. 19, pp. 510-517.

Børsting et al., "Impact of selected coagulants and starters on primary proteolysis and amino acid release related to bitterness and structure of reduced-fat Cheddar cheese", Dairy Sd. & Technol. (Oct. 2012) vol. 92, pp. 593-612.

Creamer et al., "Rheological Evaluation of Maturing Cheddar Cheese", Journal of Food Science (1982) vol. 47, pp. 631-636.

Ehren et al., "Protein engineering of improved prolyl endopeptidases for celiac sprue therapy", Protein Engineering, Design & Selection (Oct. 2008) vol. 21, No. 12, pp. 699-707.

Gilliland et al., "The Three-Dimensional Structure of Recombinant Bovine Chymosin at 2.3 Å Resolution", Protiens: Structure Function, and Genetics, (Jan. 1990) vol. 8, pp. 82-101.

Govindarajan et al., "Mapping of Amino Acid Substitutions Conferring Herbicide Resistance in Wheat Glutathione Transferase", ACS Synthetic Biology (Jun. 2014) vol. 4, pp. 221-227.

Gustchina et al., "Post X-ray crystallographic studies of chymosin: the existence of two structural forms and the regulation of activity by the interaction with the histidine-proline cluster of $_k$-casein", FEBS Letters (1996) vol. 379 pp. 60-62.

Jensen et al., "Camel and bovine chymosin: the relationship between their structures and cheese-making properties", Acta Crystallographica (2013) vol. D69, pp. 901-913.

Kumar et al., "Chymosin and other milk coagulants: sources and biotechnological interventions", Critical Reviews in Biotechnology (2010) vol. 30 No. 4, pp. 243-258.

McSweeney "Biochemistry of cheese ripening", International Journal of Dairy Technology, (2004) vol. 57, No. 2/3, pp. 127-144.

(Continued)

*Primary Examiner* — Yong D Pak
(74) *Attorney, Agent, or Firm* — Foley & Lardner LLP

(57) ABSTRACT

Variants of chymosin with improved α S1-casein cleavage and C/P properties.

13 Claims, 3 Drawing Sheets

Figure 1:
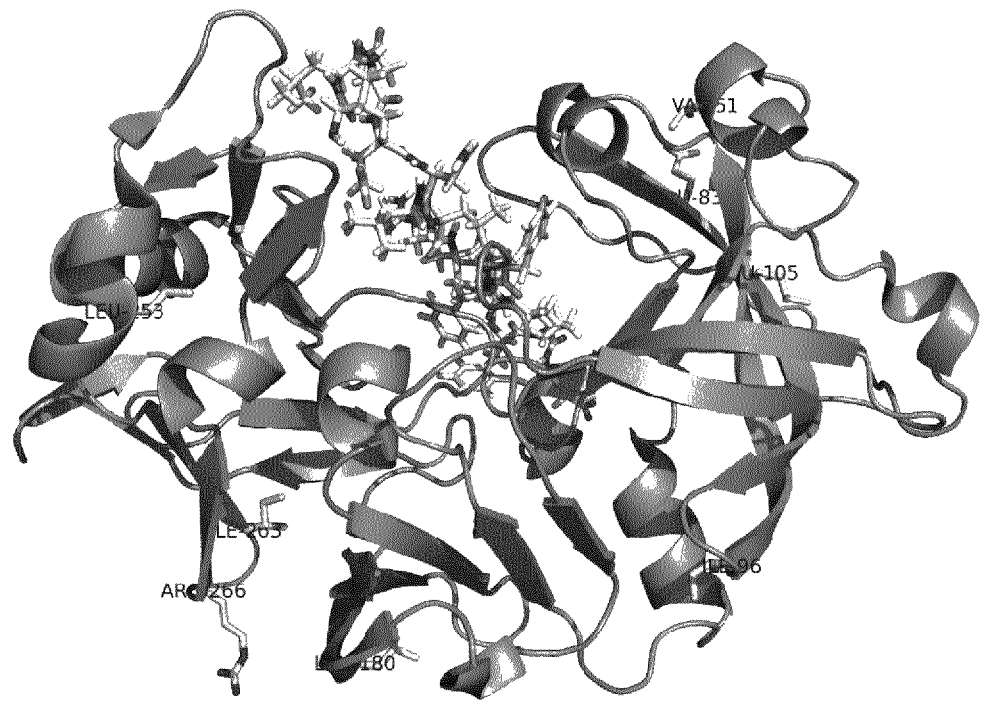

Specification includes a Sequence Listing.

(56) References Cited

OTHER PUBLICATIONS

Møller et al., "Comparison of the Hydrolysis of Bovine $_k$-Casein by Camel and Bovine Chymosin: A Kinetic and Specificity Study", Journal of Agricultural and Food Chemistry (May 2012) pp. 5454-5460.

Moynihan et al., "Effect of camel chymosin on the texture, functionality, and sensory properties of low-moisture, part-skim Mozzarella cheese", J. Dairy Sci. (2013) vol. 97, pp. 85-96.

Newman et al., "X-ray Analyses of Aspartic Proteinases IV Structure and Refinement at 2.2 Ø Resolutions of Bovine Chymosin", J. Mol. Biol. (1991) vol. 221, pp. 1295-1309.

Palmer et al., "Bovine Chymosin: A Computational Study of Recognition and Binding of Bovine $_k$-Casein", Biochemistry (Feb. 2010) vol. 49, pp. 2563-2573.

Schechter et al., "On the Size of the Active Site in Proteases", Biochemical and Biophysical Research Communications (1967) vol. 27, No. 2 pp. 157-162.

Sørensen et al., "Hot-Spot Mapping of the Interactions between Chymosin and Bovine $_k$-Casein", Journal of Agricultural and Food Chemistry (Jul. 2013) vol. 61, pp. 7949-7959.

Visser et al., "Peptide substrates for chymosin (rennin)" Biochem. J. (1987) vol. 244, pp. 553-558.

Chitpinityol et al., "Site-specific mutations of calf chymosin B which influence milk-clotting activity", Food Chemistry (1998) vol. 62, No. 2, pp. 133-139.

U.S. Appl. No. 61/642,095, filed May 3, 2012, Dekker et al.

Albert et al., "Protein Engineering Aspartic Proteinases: Site-Directed Mutagenesis, Biochemical Characterisation, and X-Ray Analysis of Chymosins with Substituted Single Amino Acid Substitutions and Loop Replacements," in Aspartic Proteinases, Chapter 23, pp. 169-178 (1998) (James, ed.).

Claverie-Martin et al., "Aspartic Proteases Used in Cheese Making," in Industrial Enzymes pp. 207-219 (2007) (J. Polaina and A.P. MacCabe, eds.).

Chen et al., "Functional Implications of Disulfide Bond, Cys206-Cys210, in Recombinant Prochymosin (Chymosin)," Biochemistry 2000, 39, 12140-12148 (Published online Sep. 2000).

Kappeler et al. "Compositional and Structural Analysis of Camel Milk Proteins with Emphasis on Protective Proteins," ETH Zurich Research Collection, Dissertation, ETH No. 12947, pp. 1-137 (1998).

Filippovich et al. "Radicals," pp. 38-43 (2005).

Beppu,et al., "Modification of Milk-clotting aspartic proteases, chymosin and mucor rennin," GBF Monographs, pp. 87-92 (Dec. 1989).

Brenden et al., "Introduction to Protein Structure," Garland Publishing., Inc. New York, p. 247, 1991.

Database UniProt [Online] Oct. 1, 2000 (Oct. 1, 2000),"SubName: Full=Prochymosin {ECO:0000313|EMBL:AAF27315.1};", retrieved from EBI accession No. Uniprot:Q9N1P5 Database accession No. Q9N1P5.

Database UniProt [Online] Feb. 5, 2008 (Feb. 5, 2008), "SubName: Full=Preprochymosin b {ECO:0000313|EMBL:ABX55935.1}; EC=3.4.23.4 {ECO:0000313|EMBL:ABX55935.1};", retrieved from EBI accession No. Uniprot:A9LY78 Database accession No. A9LY78; -& Juan Andres.

Database UniProt [Online] Nov. 1, 1990 (Nov. 1, 1990), "RecName: Full=Chymosin; EC=3.4.23.4; AltName: Full=Preprorennin; Flags: Precursor;", retrieved from EBI accession No. Uniprot:P18276 Database accession No. P18276 ; -& J. Pungercar et al: "Complete primary structure of lamb preprochymosin deduced from cDNA", Nucleic Acids Research, vol. 18, No. 15, Aug. 11, 1990 (Aug. 11, 1990), pp. 4602-4602, XP055314297, GB ISSN: 0305-1048, DOI: 10.1093/nar/18.15.4602.

Database UniProt [Online] Mar. 20, 2007 (Mar. 20, 2007), "SubName: Full=Preprochymosin {ECO:0000313|EMBL:ABN13683.1};", retrieved from EBI accession No. Uniprot:A3F4M4 Database accession No. A3F4M4.

Database Geneseq [Online] Jan. 2, 2014 (Jan. 2, 2014), "Bovine derived mature chymosin B variant H76Q.", retrieved from EBI accession No. GSP:BAY37837 Database accession No. BAY37837; -& WO 2013/164479 A2 (DSM IP Assets BV [NL]) Nov. 7, 2013 (Nov. 7, 2013).

Lindbad-Toh et al., E2R9E5_CANLF. UnitProtKB Database. 2014.

Houen, et al., "The Primary Structure and Enzymic Properties of Porcine Prochymosin and Chymosin," Int. J. Biochem. Cell Biol., vol. 28, No. 6, pp. 667-675 (1996).

Kageyama, "New World Monkey Pepsinogens A and C, and Prochymosins, Purification, Characterization of Enzymatic Properties, cDNA Cloning, and Molecular Evolution," Journal of Biochemistry, vol. 127, pp. 761-770 (Feb. 2000).

Kappeler et al., "Characterization of recombinant camel chymosin reveals superior properties for the coagulation of bovine and camel milk," Biochemical and Biophysical Research Communications, 342 (2006) 647-654.

Lavallie, "Production of Recombinant Proteins in *Escherichia coli,*" Current Protocols in Protein Science (1995) 5.1.1-5.1.8.

Lindblad-Toh et al., "Genome sequence, comparative analysis and haplotype structure of the domestic dog," Nature 438: 803-819 (2009).

Pitts et al.; "Expression and characterisation of chymosin pH optima mutants produced in *Trichoderma reesei*"; Journal of Biotechnology, 28(1): 69-83 (Mar. 1993).

Preprochymosin b, A9LY78,UniProt, May 16, 2012, [searched on Mar. 17, 2017]. URL: https://www.uniprot.org/A9LY78.txt?version=21.

Pungerčar et al., "Complete primary structure of lamb prepochymosin deduced from cDNA," Nucleic Acids Research, vol. 18, No. 15:4602 (Aug. 1990).

Sambrook et al., Molecular Cloning, 1989, Cold Spring Harbor Laboratory Press, pp. 8.46-8.52 and pp. 11.2-11.19.

Strop et al.; "Engineering Enzyme Subsite Specificity: Preparation, Kinetic Characterization, and X-ray Analysis at 2.0-Å Resolution of Val111Phe Site-Mutated Calf Chymosin"; Biochemistry, 29: 9863-9871 (Oct. 1990).

Suzuki et al.; "Alteration of catalytic properties of chymosin by site-directed mutagenesis"; Protein Engineering, 2(7): 563-569 (May 1989).

Suzuki et al.; "Site-directed mutagenesis reveals functional contribution of Thr218, Lys220 and Asp 304 in chymosin"; Protein Engineering, 4(1): 69-71 (Oct. 1990).

Vallejo et al., "Cloning and Expression of Buffalo Active Chymosin in Pichia pastoris," J. Agric. Food Chem., vol. 56, No. 22, pp. 10606-10610 (Nov. 2008).

Van Den Brink et al.; "Increased production of chymosin by glycosylation"; Journal of Biotechnology, 125(2): 304-310 (Sep. 2006)(published online Apr. 2006).

Williams et al.; "Mutagenesis, biochemical characterization and X-ray structural analysis of point mutants of bovine chymosin"; Protein Engineering; 10(9): 991-997 (Sep. 1997).

Zhang et al.; "Functional implications of disulfide bond, Cys45-Cys50, in recombinant prochymosin"; Biochimica et Biophysica Acta, 1343(2): 278-286 (Dec. 1997).

Møller, et al., "Camel and Bovine Chymosin Hydrolysis of Bovine αs1- and β-Caseins Studied by Comparative Peptide Mapping," Journ. of Agriculture and Food Chemistry, vol. 60, No. 45, pp. 11421-11432 (Oct. 2012).

V. V. Starovoitova et al. "Comparative Investigation of Functional Properties of Calf Chymosin and its Recombinant Forms," Biohimiya, 2006, tom 71, vyp. 3, s. 402-407 (in Russian).

* cited by examiner

VARIANTS OF CHYMOSIN WITH IMPROVED PROPERTIES

CROSS-REFERENCE TO RELATED APPLICATIONS

The present application is the U.S. National Stage of International Application PCT/EP2016/070468, filed Aug. 31, 2016, and claims priority to European Patent Application No. 15183205.2, filed Aug. 31, 2015.

FIELD OF THE INVENTION

The present invention relates to variants of chymosin with improved αS1-casein and C/P cleavage properties.

BACKGROUND OF THE INVENTION

Chymosin (EC 3.4.23.4) and pepsin (EC 3.4.23.1), the milk clotting enzymes of the mammalian stomach, are aspartic proteases belonging to a broad class of peptidases.

When produced in the gastric mucosal cells, chymosin and pepsin occur as enzymatically inactive pre-prochymosin and pre-pepsinogen, respectively. When chymosin is excreted, an N-terminal peptide fragment, the pre-fragment (signal peptide) is cleaved off to give prochymosin including a pro-fragment. Prochymosin is a substantially inactive form of the enzyme which, however, becomes activated under acidic conditions to the active chymosin by autocatalytic removal of the pro-fragment. This activation occurs in vivo in the gastric lumen under appropriate pH conditions or in vitro under acidic conditions.

The structural and functional characteristics of bovine, i.e. *Bos taurus*, pre-prochymosin, prochymosin and chymosin have been studied extensively. The pre-part of the bovine pre-prochymosin molecule comprises 16 aa residues and the pro-part of the corresponding prochymosin has a length of 42 aa residues. The active bovine chymosin comprises 323 aa.

Chymosin is produced naturally in mammalian species such as bovines, camels, caprines, buffaloes, sheep, pigs, humans, monkeys and rats.

Bovine and camel chymosin have for a number of years been commercially available to the dairy industry.

Enzymatic coagulation of milk by milk-clotting enzymes, such as chymosin and pepsin, is one of the most important processes in the manufacture of cheeses. Enzymatic milk coagulation is a two-phase process: a first phase where a proteolytic enzyme, chymosin or pepsin, attacks κ-casein, resulting in a metastable state of the casein micelle structure and a second phase, where the milk subsequently coagulates and forms a coagulum (reference 1). Besides facilitating coagulation of milk by cleaving κ-casein, chymosins cleave alphaS1-casein (αS1-casein), primarily between Phe23 and Phe24 (Moynihan et al. 2014), resulting in the formation of an αS1(1-23) peptide.

The formation of the αS1(1-23) peptide has been described to contribute to softening of the cheese texture (Creamer & Olsen, 1982). A correlation of both parameters has for example been found comparing chymosins from *Bos taurus* and *Camelus dromedarius*. While bovine chymosin cleaves αS1casein between Phe23 and Phe24 faster (Creamer & Olsen, 1982, Bansal et al. 2009) compared to camel chymosin, it yields softer cheeses with higher texture break-down, e.g. cheddar (Creamer & Olsen, 1982, Bansal et al. 2009) and mozzarella (Moynihan et al. 2014).

The access to cheese coagulants with a varying degree of αS1(1-23) peptide formation may enable the cheesemaker to impose different levels of softness to the cheese matrix. Chymosin variants with both increased or decreased αS1(1-23) peptide formation in cheese making are thus of high industrial interest. Coagulants with a fine-tuned αS1-casein proteolysis would facilitate the manufacturing of a wide variety of cheese types with optimal curd firmness.

The references listed immediately below may in the present context be seen as references describing mutants of chymosin:

WO02/36752A2 (Chr. Hansen) describes recombinant production of camel chymosin.

WO2013/174840A1 (Chr. Hansen) describes mutants/variants of bovine and camel chymosin.

WO2013/164479A2 (DSM) describes mutants of bovine chymosin.

Suzuki et al: Site directed mutagenesis reveals functional contribution of Thr218, Lys220 and Asp304 in chymosin, Protein Engineering, vol. 4, January 1990, pages 69-71;

Suzuki et al: Alteration of catalytic properties of chymosin by site-directed mutagenesis, Protein Engineering, vol. 2, May 1989, pages 563-569;

van den Brink et al: Increased production of chymosin by glycosylation, Journal of biotechnology, vol. 125, September 2006, pages 304-310;

Pitts et al: Expression and characterisation of chymosin pH optima mutants produced in *Trichoderma reesei*, Journal of biotechnology, vol. 28, March 1993, pages 69-83;

M. G. Williams et al: Mutagenesis, biochemical characterization and X-ray structural analysis of point mutants of bovine chymosin, Protein engineering design and selection, vol. 10, September 1997, pages 991-997;

Strop et al: Engineering enzyme subsite specificity: preparation, kinetic characterization, and x-ray analysis at 2.0 ANG resolution of Val111phe site mutated calf chymosin, Biochemistry, vol. 29, October 1990, pages 9863-9871;

Chitpinityol et al: Site-specific mutations of calf chymosin B which influence milk-clotting activity, Food Chemistry, vol. 62, June 1998, pages 133-139;

Zhang et al: Functional implications of disulfide bond, Cys45-Cys50, in recombinant prochymosin, Biochimica et biophysica acta, vol. 1343, December 1997, pages 278-286.

None of the prior art references mentioned above describe directly and unambiguously any of the chymosin variants with altered αS1-casein cleavage frequency and increased C/P value compared to the parent from which the variant is derived, as described below.

SUMMARY OF THE INVENTION

The problem to be solved by the present invention is to provide variants of chymosin which, when compared to the parent polypeptide, have either a lower or higher αS1-casein cleavage frequency and an increased C/P value.

By a dedicated effort and by applying a multidimensional research strategy, the present inventors have found single mutations as well as combinations of mutations that allow the design of isolated chymosin polypeptide variants characterized in that:

(a) the isolated chymosin polypeptide variant has a C/P value that is at least 200% of the C/P value of isolated camel chymosin characterized by the mature polypeptide of SEQ ID NO:2; and (b) the isolated chymosin polypeptide variant cleaves αS1-casein with a frequency of less than 80% of the frequency of αS1-casein cleavage of isolated camel chymosin characterized by the mature polypeptide of SEQ ID NO:2, wherein αS1-casein cleavage is determined by quantifying αS1-casein peptides obtained by incubating skim milk with the chymosin variant or the camel chymosin, wherein quantification is carried out by RP-HPLC coupled to an ESI-Q-TOF mass spectrometer.

Additionally the present inventors have found single mutations as well as combinations of mutations that allow the design of isolated chymosin polypeptide variants characterized in that:

(a) the isolated chymosin polypeptide variant has a C/P value that is at least 200% of the C/P value of isolated camel chymosin characterized by the mature polypeptide of SEQ ID NO:2; and (b) the isolated chymosin polypeptide variant cleaves αS1-casein with a frequency of at least 115% of the frequency of αS1-casein cleavage of isolated camel chymosin characterized by the mature polypeptide of SEQ ID NO:2, wherein αS1-casein cleavage is determined by quantifying αS1-casein peptides obtained by incubating skim milk with the chymosin variant or the camel chymosin, wherein quantification is carried out by RP-HPLC coupled to an ESI-Q-TOF mass spectrometer.

Furthermore, the present invention provides methods for making isolated chymosin polypeptide variants, the method comprising the following steps:

(a): making an alteration at one or more positions in the DNA sequence encoding the mature polypeptide of SEQ ID NO:2 (camel cymosin), wherein the alteration comprises a substitution, a deletion or an insertion in at least one amino acid position corresponding to Y11I, Y11V, L12M, K19T, V51L, R61S, H76Q, E83S, I96L, L105E, D144Q, Q162S, S164G, M165E, L166V, L180I, V203A, L221I, S226T, T239S, R242E, G251D, G251W, L253I, V260T, I263L, R266V, S273Y, Q288E, G289S, E294Q, Y307F, V309I, R316L and/or V317L, or alternatively V32L, I45V, N50K, G70D, G70N, D98V, N100Q, V136I, M142I, H146R, S154A, V155F, M157L, D158S, V198I, I200V, F223V, K231N, G244D, V248I, R254S, M256L, V259I, E262T, D267Q, D279E, T284S, N291Q N292H, L295K, and/or K321P.

(b): producing and isolating the altered polypeptide of step (a).

In a related aspect, the present invention also relates to a method for making an isolated chymosin polypeptide variant having an altered αS1-casein cleavage frequency compared to the parent polypeptide, the method comprising the steps:

(a): making an alteration at one or more positions in a parent polypeptide, wherein the alteration is comprising a substitution, a deletion or an insertion in at least one amino acid position corresponding to any of positions: Y11I, Y11V, L12M, K19T, V51L, R61S, H76Q, E83S, I96L, L105E, D144Q, Q162S, S164G, M165E, L166V, L180I, V203A, L222I, S226T, T239S, R242E, G251D, G251W, L253I, V260T, I263L, R266V, S273Y, Q288E, G289S, E294Q, Y307F, V309I, R316L, V317L, V32L, I45V, N50K, G70D, G70N, D98V, N100Q, V136I, M142I, H146R, S154A, V155F, M157L, D158S, V198I, I200V, F223V, K231N, G244D, V248I, R254S, M256L, V259I, E262T, D267Q, D279E, T284S, N291Q N292H, L295K, and/or K321P, (b): producing and isolating the altered polypeptide of step (a), and wherein:

(i): the amino acid position of the parent polypeptide is determined by an alignment of the parent polypeptide with the mature polypeptide of SEQ ID NO: 2 (camel chymosin); and (ii): the parent polypeptide has at least 65% sequence identity with the mature polypeptide of SEQ ID NO: 1 (bovine chymosin) and/or at least 65% sequence identity with the mature polypeptide of SEQ ID NO: 2 (camel chymosin).

Furthermore the present invention also relates to specific combinations of substitutions as outlined below in the embodiments of the invention.

The present disclosure also relates to food or feed products comprising the isolated chymosin polypeptide variants as well as the use of isolated chymosin polypeptide variants in a process for making cheese.

DETAILED DESCRIPTION OF THE INVENTION

Based on a comparative analysis of different variants—the present inventors have identified a number of amino acid positions that are herein important in the sense that by making a variant in one or more of these positions one may get an improved chymosin variant with either lower or higher αS1-casein cleavage frequency and increased C/P value.

Hence, as indicated above, the present invention provides isolated chymosin polypeptide variants characterized in that:

(a) the isolated chymosin polypeptide variant has a C/P value that is at least 200% of the C/P value of isolated camel chymosin characterized by the mature polypeptide of SEQ ID NO:2; and (b) the isolated chymosin polypeptide variant cleaves αS1-casein with a frequency of less than 80% or at least 115% of the frequency of αS1-casein cleavage of isolated camel chymosin characterized by the mature polypeptide of SEQ ID NO:2, wherein αS1-casein cleavage is determined by quantifying αS1-casein peptides obtained by incubating skim milk with the chymosin variant or the camel chymosin, wherein quantification is carried out by RP-HPLC coupled to an ESI-Q-TOF mass spectrometer.

More specifically an aspect of the present invention provides isolated chymosin polypeptide variants characterized in that:

(a) the isolated chymosin polypeptide variant has a C/P value that is at least 200% of the C/P value of isolated camel chymosin characterized by the mature polypeptide of SEQ ID NO:2; and (b) the isolated chymosin polypeptide variant cleaves αS1-casein with a frequency of less than 80% of the frequency of αS1-casein cleavage of isolated camel chymosin characterized by the mature polypeptide of SEQ ID NO:2, wherein αS1-casein cleavage is determined by quantifying αS1-casein peptides obtained by incubating skim milk with the chymosin variant or the camel chymosin, wherein quantification is carried out by RP-HPLC coupled to an ESI-Q-TOF mass spectrometer.

In a closely related aspect, the isolated chymosin polypeptide variant of present invention that cleaves αS1-casein with a frequency of less than 80% of the frequency of αS1-casein cleavage of isolated camel chymosin characterized by the mature polypeptide of SEQ ID NO:2, comprise one or more of the following substitutions, wherein the substitution is specified in relation to the amino acid sequence of the mature polypeptide of SEQ ID NO:2: Y11I, Y11V, L12M, K19T, V51L, R61S, H76Q, E83S, I96L, L105E, D144Q, Q162S, S164G, M165E, L166V, L180I, V203A, L221I, S226T, T239S, R242E, G251D, G251W, L253I, V260T, I263L, R266V, S273Y, Q288E, G289S, E294Q, Y307F, V309I, R316L and/or V317L.

The above specified mutations may form part of combinations of mutations to generate variants or mutants comprising multiple substitutions. In particular and as a related aspect, the isolated chymosin polypeptide variant having decreased αS1-casein cleavage frequency may comprise one or more of the combinations of the following substitutions and wherein each substitution is specified in relation to the amino acid sequence of the mature polypeptide of SEQ ID NO:2:

Y21S+H76Q+Y307F+V317L,
R61S+L166V+T239S,
V32L+E294Q+R316L+V317L,
S226T+G244D+I263L+G289S,
V203A+V248I+G251W+L253I+Y268F,
D59N+L222I+G251D+E83S+Q162S,
D59N+L222I+G251D+Y21S+L215V+L105E,
D59N+L222I+G251D+H76Q+L105E+V260T,
D59N+L222I+G251D+V203A+R266V+F223A,
L12M+D59N+H76Q+S154A+M165E+V203A+L222I+G251D+V309I,
L12M+V51L+H76Q+M165E+G251D,
L12M+V51L+D59N+H76Q+L166V+L222I+G251D,
L12M+D59N+H76Q+D144Q+M165E+V203A+L222I,
L12M+K19T+D59N+H76Q+S154A+M165E+V198I+L222I+G251D,
L12M+V51L+D59N+F66Y+H76Q+M165E+V203A+L222I+G251W,
V51L+D59N+H76Q+M165E+L180I+L222I+G251D+E262T,
L12M+D59N+H76Q+M165E+G251D+Q288E+V309I+K321P,
D59N+H76Q+I96L+L130I+S164G+L222I+R242E+G251D,
H76Q+I96L+S164G+L222I+R242E+G251D+S273Y,
K19T+D59N+H76Q+I96L+S164G+L166V+L222I+G251D+S273Y,
H76Q+S164G+L166V+L222I+R242E+G251D+S273Y,
Y21S+H76Q+S164G+L222I+R242E+G251D+S273Y,
D59N+H76Q+I96L+S132A+S164G+L222I+S226T+G251D+S273Y,
D59N+H76Q+I96L+S132A+S164G+L166V+L222I+G251D+S273Y,
K19T+D59N+H76Q+S164G+L222I+N249D+S273Y,
H76Q+S164G+L222I+N249D+G251D+S273Y+V309I,
H76Q+I96L+S164G+G251D+S273Y+V309I,
K19T+D59N+H76Q+S164G+R242E+N249D+G251D+S273Y,
Y21S+D59N+H76Q+S164G+L222I+S226T+G251D+S273Y+V309I
D59N+H76Q+I96L+S164G+L222I+S226T+N249D+G251D+S273Y,
H76Q+S164G+L166V+L222I+S226T+S273Y,
D59N+H76Q+L130I+S164G+L166V+L222I+G251D+S273Y+V309I,
D59N+H76Q+S164G+L222I+S226T+R242E,
K19T+D59N+I96L+S164G+L222I+G251D,
D59N+H76Q+I96L+S164G+L222I+S226T+G251D+S273Y+V309I,
D59N+H76Q+L130I+S164G+G251D+V309I,
D59N+H76Q+L130I+L166V+L222I+N249D+G251D+S273Y,
Y21S+D59N+H76Q+I96L+S164G+L222I+N249D+G251D+S273Y,
K19T+D59N+S164G+L166V+L222I+S226T+G251D+S273Y,
D59N+H76Q+L130I+S132A+S164G+L222I+R242E+G251D+S273Y,
K19T+Y21S+H76Q+S164G+L222I+G251D+S273Y,
D59N+H76Q+S164G+L222I+R242E+S273Y+V309I,
K19T+Y21S+D59N+H76Q+S132A+S164G+L222I+G251D+S273Y,
K19T+D59N+H76Q+L130I+S164G+L222I+S226T+G251D+S273Y,
D59N+H76Q+S164G+L166V+L222I+N249D+G251D+S273Y+V309I,
K19T+Y21S+D59N+H76Q+L130I+S164G+L222I+S273Y,
Y21S+D59N+S164G+L222I+R242E+G251D+S273Y+V309I,
K19T+D59N+H76Q+L166V+L222I+R242E+G251D+S273Y,
D59N+S132A+S164G+L222I+R242E+N249D+G251D+S273Y,
D59N+H76Q+I96L+L130I+S164G+L222I+N249D+G251D+S273Y,
Y21S+D59N+H76Q+S164G+L166V+N249D+G251D+S273Y,
H76Q+S132A+S164G+L222I+N249D+G251D,
D59N+H76Q+S132A+S164G+L166V+S273Y,
K19T+D59N+H76Q+S132A+L222I+G251D+S273Y+V309I,
H76Q+L130I+L222I+S226T+G251D+S273Y,
Y21S+D59N+H76Q+I96L+L222I+S273Y,
Y11I+K19T+D59N+E83S+I96L+S164G+L222I+N249D,
Y11I+K19T+I96L+S164G+L222V+R242E+G251D,
Y11V+K19T+I96L+S164G+L166V+L222I+R242E,
Y11V+E83S+I96L+S164G+L222I+R242E+G251D+L253I+I263L,
Y11V+I96L+S164G+L222I+R242E+N249D+L253I+I263L,
K19S+I96L+S164G+L166V+L222I+R242E,
K19T+I96L+S164G+L166V+L222I+R242E+N249D+I263L,
Y11V+K19T+D59N+I96L+S164N+L166I+L222I+G251D,
H76Q+I96L+S164G+L222I+R242E+G251D+S273Y,
Y11V+K19T+E83S+I96L+S164G+L166V+L222I+R242E+G251D,
Y11V+E83S+I96L+S164G+L222I+R242E+L253I+I263L,
Y11V+K19T+D59N+I96L+S164G+L166V+L222I+R242E+G251D+L253I,
K19T+D59N+I96V+S164G+L166V+L222I+R242E+I263L,
Y11V+D59N+I96L+S164G+L222I+G251D+L253V,
I96L+S164G+L166V+L222I+R242E+N249D+I263L,
K19S+D59N+I96L+S164G+L222I+R242E+N249E+G251D,
H76Q+I96L+S164G+L222I+R242E+G251D,
Y11I+K19T+D59N+S164G+L222I+G251D+I263V,

K19T+I96L+S164G+L166V+L222I+R242E+N249D+G251D+I263V,
K19T+E83S+I96L+S164G+L222I+R242E+G251D+L253I,
I96L+S164G+L222I+R242E+N249D+G251D+I263L,
K19T+D59N+I96L+S164G+L166V+L222I+R242D+G251D+L253I,
D59N+I96L+S164G+L222I+R242E+L253I+I263L,
K19T+I96L+S164G+L166V+L222I+N249D+I263L,
K19T+D59N+I96L+S164G+L166I+L222I+R242D+G251D+I263V,
K19T+D59N+I96L+S164G+L222V+R242E+N249D+L253I,
K19T+D59N+I96L+S164G+L166I+L222I+R242E+N249D,
K19T+E83S+I96L+S164G+L222I+R242E+N249D+G251D+L253I,
I96L+S164G+L222I+R242E+G251D+S273Y,
K19T+E83T+I96L+S164G+L222I+R242E+L253V,
K19T+I96L+S164G+R242E+L253I,
K19T+D59N+I96L+S164G+L222I+N249E+G251D+L253V+I263L,
K19T+D59N+I96L+S164G+L222V+N249E+G251D+I263V,
I96L+S164G+L222I+R242E+G251D,
K19T+I96L+S164N+L222I+R242E+I263L,
K19T+E83S+I96L+S164G+L166V+L222I+R242E+N249D+G251D+L253I,
K19T+D59N+E83T+S164G+L166V+L222I+R242D+G251D,
K19T+D59N+I96L+S164G+L222I+G251D,
D59N+I96L+L166V+L222I+R242E+G251D,
Y11I+K19T+D59N+I96V+L222I+R242D+G251D,
K19T+I96V+S164G+L222I+N249D+G251D+L253I,
H76Q+N100Q+N291Q,
R67Q+L130I+M157L+D158S+R242E+N291Q,
V32L+R67Q+L130I+M157L+K231N+M256L,
R67Q+V136I+M157L+L222I+V248I,
Y11V+R67Q+L130I+M157L+L222I+R242E,
R67Q+I96L+N100Q+L130I+M157L+N292H.
Y11I+D59N+I96L+S164G+L166V+L222V+R242E+G251D+L253I,
Y11I+D59N+I96L+S164G+L166V+L222V+R242E+G251D,
Y11I+D59N+I96L+S164G+L166V+L222V+R242E+N249E+G251D,
Y11V+K19T+D59N+I96L+S164G+L166V+L222V+R242E+N249E+G251D,
Y11I+I96L+S164G+L166V+L222V+R242E+N249E+G251D,
Y11V+K19T+I96L+L166V+L222V+R242E+G251D,
Y11V+K19T+D59N+I96L+S164G+L166I+L222V+R242E+N249E+G251D+L253I,
Y11I+K19T+D59N+I96L+S164G+L166V+L222V+R242E+N249E+G251D,
Y11I+K19T+D59N+I96L+S164G+L166V+L222I+R242E+N249E+G251D,
Y11V+K19T+D59N+I96L+S164G+L166V+L222V+R242E+N249E+L253I,
Y11V+K19T+D59N+I96L+L166V+L222V+R242E+N249E+G251D+L253I,
Y11V+K19T+D59N+I96L+S164G+L166V+L222I+R242E+N249E,
Y11V+K19T+D59N+I96L+S164G+L166V+L222V+R242E+G251D,
Y11I+K19T+D59N+I96L+S164G+L166V+R242E+G251D,

Y11I+K19T+D59N+I96L+S164G+L166I+L222I+R242E+G251D,
Y11V+K19T+I96L+S164G+L166V+L222V+R242E+N249E+G251D,
Y11I+K19T+D59N+I96L+S164G+L166I+L222V+R242E+N249E+G251D,
Y11V+D59N+I96L+S164G+L166I+L222I+R242E+G251D,
Y11V+K19T+D59N+I96L+S164G+L166I+L222V+R242E+N249E+G251D,
Y11I+K19T+D59N+I96L+S164G+L222I+R242E,
Y11I+K19T+I96L+S164G+L166V+R242E+N249E+G251D,
Y11I+I96L+S164G+L222I+R242E,
Y11I+K19T+D59N+I96L+S164G+L222I+R242E+N249E+G251D,
Y11V+D59N+I96L+S164G+L166I+L222V+R242E+G251D+L253I,
Y11I+K19T+D59N+I96L+L222V+R242E+N249E+G251D,
Y11V+K19T+D59N+I96L+S164G+L166I+L222I+R242E+N249E+G251D,
Y11V+K19T+D59N+I96L+S164G+L222I+R242E+N249E+G251D,
Y11I+D59N+I96L+S164G+L222I+R242E+G251D,
Y11V+K19T+D59N+I96L+S164G+L166I+R242E+N249E+G251D+L253I,
Y11I+D59N+I96L+S164G+L222V+R242E+N249E+G251D,
Y11I+K19T+S164G+L166I+L222V+R242E+N249E+G251D,
Y11V+K19T+D59N+S164G+L166V+L222I+R242E+N249E+G251D,
Y11V+K19T+D59N+I96L+S164G+L166V+R242E,
Y11I+K19T+D59N+I96L+S164G+L222V+R242E+N249E,
Y11V+K19T+D59N+I96L+S164G+L222V+R242E+G251D,
Y11V+K19T+D59N+I96L+S164G+R242E+G251D,
Y11V+K19T+D59N+I96L+S164G+L166I+L222V+R242E+G251D,
Y11I+I96L+L222V+R242E+N249E+G251D,
Y11I+K19T+D59N+S164G+L166I+L222V+R242E+G251D,
Y11V+K19T+D59N+I96L+S164G+L222V+R242E+N249E+G251D,
Y11V+K19T+D59N+I96L+L222V+R242E+G251D,
Y11V+K19T+D59N+S164G+L166I+L222I+R242E+G251D,
Y11V+K19T+D59N+L166V+L222I+R242E+N249E+G251D+L253I,
Y11V+K19T+I96L+L222V+R242E+N249E+G251D or
Y11I+K19T+L222V+R242E+N249E+G251D.

Accordingly, the present invention also comprise isolated chymosin polypeptide variants characterized in that:

(a) the isolated chymosin polypeptide variant has a C/P value that is at least 200% of the C/P value of isolated camel chymosin characterized by the mature polypeptide of SEQ ID NO:2; and (b) the isolated chymosin polypeptide variant cleaves αS1-casein with a frequency of at least 115% of the frequency of αS1-casein cleavage of isolated camel chymosin polypeptide characterized by the mature polypeptide of SEQ ID NO:2, wherein αS1-casein cleavage is determined by quantifying αS1-casein peptides obtained by incubating skim milk with the chymosin variant or the camel chymosin, wherein quantification is carried out by RP-HPLC coupled to an ESI-Q-TOF mass spectrometer.

In a closely related aspect, the chymosin polypeptide variant of present invention that cleaves αS1-casein with a frequency of at least 115% of the frequency of αS1-casein cleavage of isolated camel chymosin polypeptide characterized by the mature polypeptide of SEQ ID NO:2, comprises one or more of the following substitutions, wherein the substitution is specified in relation to the amino acid sequence of the mature polypeptide of SEQ ID NO:2: V32L, I45V, N50K, G70D, G70N, D98V, N100Q, V136I, M142I, H146R, S154A, V155F, M157L, D158S, V198I, I200V, F223V, K231N, G244D, V248I, R254S, M256L, V259I, E262T, D267Q, D279E, T284S, N291Q N292H, L295K, and/or K321P.

In another related aspect, the isolated chymosin polypeptide variant having increased αS1-casein cleavage frequency comprises one or more of the combinations of the following substitutions and wherein each substitution is specified in relation to the amino acid sequence of the mature polypeptide of SEQ ID NO:2:

G70D+S74F+D158S+R254S+S277N,
L130I+M142I+I200V+V259I+E294Q,
Y21S+R61S+H146R,
R61S+G163E+M256L+S277N,
D59N+S271P+T284S,
V248I+S226T+E294Q,
S74F+G244D+S271P,
V221K+V248I+S255Y,
V183I+G251W+M256L,
R61Q+V136I+Y268F+T284S+Y307F,
N50K+D158S+V203A+E294Q,
D98V+G251D+M256L+V259I,
V183I+V248I+G244D+T284S,
N50K+R61S+Y127F+G244D+G251D,
I96L+F223V+G244D+R254S+M256L,
H146R+D158S+S273Y,
S74F+V259I+Y268F,
G70N+D98V+V136I,
I96L+M142I+R145Q+H146R,
V32L+G163E+T186S+Q188E+L295K,
R61Q+V136I+Y268F+T284S+Y307F,
S132A+Q188E+F223V,
I200V+G251D+G289S,
N50K+D158S+V203A+E294Q,
F223V+G251W+S273Y+D279E,
D59N+L222I+G251D+V32L+L12M+T284S,
D59N+L222I+G251D+V155F+E262T+V32L,
D59N+L222I+G251W+S154A+V203A,
D59N+L222I+G251D+V32L+K321P+V260T,
D59N+L222I+G251D+V198I+V203A+K321P,
D59N+L222I+G251D+S273Y+T284S+D267Q
V32L+N100Q+N291Q,
N292H+N100Q+N291Q,
V221K+N100Q+N291Q,
I297A+N100Q+N291Q,
R67Q+N100Q+L130I+M157L+L222I+K231N,
R67Q+L130I+V248I+M256L+N292H,
V32L+R67Q+L130I+K231N+N292H,
L130I+M157L+V248I+M256L+N291Q,
V32L+R67Q+V136I+M157L+N291Q,
R67Q+L130I+K231N+V248I+N291Q,
V32L+R67Q+G70D+N100Q+M157L,
R67Q+N100Q+L130I+D158S+V248I,
R67Q+N100Q+L130I+M157L+K231N+N291Q,
R67Q+N100Q+L130I+M157L+V248I+N291Q and/or
N100Q+L130I+S132A+M157L+K231N.

The present invention further provides methods of making the isolated chymosin polypeptide variants, methods of making a food or feed product using the isolated chymosin polypeptide variants, food and feed products comprising these variants as well as the use of the variants for making food and feed products.

Additionally, the present invention relates to the use of chymosin polypeptide variants of present invention in processes for making cheese, such as e.g. pasta filata, Cheddar, Continental type cheese, soft cheese or white brine cheese.

Determining the Amino Acid Position of a Chymosin of Interest

The amino acid numbering as used herein to specify the variant is based on the mature peptide.

As known in the art—different natural wildtype chymosin polypeptide sequences obtained from different mammalian species (such as e.g. bovines, camels, sheep, pigs, or rats) are having a relatively high sequence similarity/identity. In the present context—a naturally obtained wildtype chymosin (such as bovine chymosin or camel chymosin) may herein be an example of a parent polypeptide—i.e. a parent polypeptide to which an alteration is made to produce a variant chymosin polypeptide of the present invention.

As outlined herein—as a reference sequence for determining the amino acid position of a parent chymosin polypeptide of interest (e.g. camel, sheep, bovine etc) is herein used the public known *Camelius dromedarius* mature chymosin sequence of SEQ ID NO: 2. It may herein alternatively be termed camel chymosin. The mature polypeptide sequence of SEQ ID NO:2 is exemplified herein as SEQ ID NO:4.

Alternatively, the amino acid sequence of another chymosin polypeptide may be aligned with the mature polypeptide disclosed in SEQ ID NO: 1, and based on the alignment, the amino acid position number corresponding to any amino acid residue in the mature polypeptide disclosed in SEQ ID NO: 1 is determined using the ClustalW algorithm or as described in working Example 1 herein.

Based on above well-known computer programs—it is routine work for the skilled person to determine the amino acid position of a herein relevant chymosin polypeptide of interest (e.g. camel, sheep, bovine etc.).

Determination of Milk Clotting Activity

Milk clotting activity may be determined using the REM-CAT method, which is the standard method developed by the International Dairy Federation (IDF method).

In this method, milk clotting activity is determined from the time needed for a visible flocculation of a standard milk substrate prepared from a low-heat, low fat milk powder with a calcium chloride solution of 0.5 g per liter (pH≈6.5). The clotting time of a rennet sample is compared to that of a reference standard having known milk-clotting activity and having the same enzyme composition by IDF Standard 110B as the sample.

Samples and reference standards are measured under identical chemical and physical conditions. Variant samples are adjusted to approximately 3 IMCU/ml using an 84 mM acetic acid buffer pH 5.5. Hereafter, 200 µl enzyme preparation was added to 10 ml preheated milk (32° C.) in a glass test tube placed in a water bath, capable of maintaining a constant temperature of 32° C.±1° C. under constant stirring. Alternatively, 20 µL enzyme preparation is added to 1 mL preheated milk as described above.

The total milk-clotting activity (strength) of a rennet is calculated in International Milk-Clotting Units (IMCU) per ml relative to a standard having the same enzyme composition as the sample according to the formula:

Strength in IMCU/ml=Sstandard×Tstandard× Dsample/Dstandard×Tsample

Sstandard: The milk-clotting activity of the international reference standard for rennet.

Tstandard: Clotting time in seconds obtained for the standard dilution.

Dsample: Dilution factor for the sample

Dstandard: Dilution factor for the standard

Tsample: Clotting time in seconds obtained for the diluted rennet sample from addition of enzyme to time of flocculation.

Alternatively, the pIMCU method may be used instead of the REMCAT method. As compared to REMCAT, flocculation time of chymosin variants in the pIMCU assay is determined by OD measurements in 96-well microtiter plates at 800 nm in a UV/VIS plate reader. A standard curve of various dilutions of a reference standard with known clotting strength is recorded on each plate. Samples are prepared by diluting enzyme in 84 mM acetate buffer, 0.1% triton X-100, pH 5.5. Reaction at 32° C. is started by adding 250 uL of a standard milk substrate containing 4% (w/w) low-heat, low fat milk powder and 7.5% (w/w) calcium chloride (pH≈6.5) to 25 uL enzyme sample. Milk clotting activity of chymosin variants in International Milk-Clotting Units (IMCU) per ml is then determined based on sample flocculation time relative to the standard curve.

Determination of Total Protein Content

Preferably, the total protein content is determined using the Pierce BCA Protein Assay Kit from Thermo Scientific following the instructions of the providers.

Calculation of Specific Clotting Activity

Specific clotting activity (IMCU/mg total protein) may be determined by dividing the clotting activity (IMCU/ml) by the total protein content (mg total protein per ml).

Nomenclature of Variants

In describing the variants of the present invention, the nomenclature described below is adapted for ease of reference. The accepted IUPAC single letter or three letter amino acid abbreviations are employed.

The specific variants discussed in this "nomenclature" section below may not be herein relevant variants of the present invention—i.e. this "nomenclature" section is just to describe the herein relevant used nomenclature as such. As indicated above, the amino acid numbering used to specify chymosin polypeptide variants of the present invention is based on the position of the amino acid in the mature chymosin polypeptide sequence.

Substitutions.

For an amino acid substitution, the following nomenclature is used: Original amino acid, position, substituted amino acid. Accordingly, a theoretical substitution of threonine with alanine at position 226 is designated as "Thr226Ala" or "T226A". Multiple mutations are separated by addition marks ("+"), e.g., "Gly205Arg+Ser411Phe" or "G205R+ S411F", representing substitutions at positions 205 and 411 of glycine (G) with arginine (R) and serine (S) with phenylalanine (F), respectively. A substitution e.g. designated "226A" refers to a substitution of a parent amino acid (e.g. T, Q, S or another parent amino acid) with alanine at position 226.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+ S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G - K - A |

Multiple Alterations.

Variants comprising multiple alterations are separated by addition marks ("+"), e.g., "Arg170Tyr+Gly195Glu" or "R170Y+G195E" representing a substitution of tyrosine and glutamic acid for arginine and glycine at positions 170 and 195, respectively.

Different Substitutions.

Where different substitutions can be introduced at a position, the different substitutions are separated by a comma, e.g., "Arg170Tyr,Glu" or "R170Y,E" represents a substitution of arginine with tyrosine or glutamic acid at position 170. Thus, "Tyr167Gly,Ala+Arg170Gly,Ala" or "Y167G,A+R170G,A" designates the following variants: "Tyr167Gly+Arg170Gly", "Tyr167Gly+Arg170Ala", "Tyr167Ala+Arg170Gly", and "Tyr167Ala+Arg170Ala".

Preferred Variants:

As outlined herein, the inventors of present invention have made a number of preferred chymosin polypeptide variants that cleave αS1-casein with different desired frequencies than the corresponding parent polypeptide while increasing the C/P value of the variant by at least a factor of 2 compared to the isolated camel chymosin characterized by the mature polypeptide of SEQ ID NO:2.

Preferred Variants with Reduced αS1-Casein Cleavage Activity

Preferred chymosin polypeptide variants of present invention comprise variants characterized in that (a) the isolated chymosin polypeptide variant has a C/P value that is at least 200% of the C/P value of isolated camel chymosin characterized by the mature polypeptide of SEQ ID NO:2; and (b) the isolated chymosin polypeptide variant cleaves αS1-casein with a frequency of less than 80% of the frequency of the αS1-casein cleavage of isolated camel chymosin characterized by the mature polypeptide of SEQ ID NO:2, wherein αS1-casein cleavage is determined by quantifying αS1-casein peptides obtained by incubating skim milk with the chymosin variant or the camel chymosin, wherein quantification is carried out by RP-HPLC coupled to an ESI-Q-TOF mass spectrometer.

In preferred aspects, the isolated chymosin polypeptide variants cleave αS1-casein with a frequency of less than 80%, less than 50%, less than 40%, less than 30% or less than 20% of the frequency of αS1-casein cleavage of isolated camel chymosin characterized by the mature polypeptide of SEQ ID NO:2. The isolated chymosin polypeptide variants of the present invention have a C/P value that is at least 200% of the C/P value of isolated camel chymosin polypeptide characterized by the mature polypeptide of SEQ ID NO:2, including a C/P value that is at least 200%, at least 300%, at least 500%, at least 900%, at least 1200% or at least 1400% of the C/P value of isolated camel chymosin polypeptide characterized by the mature polypeptide of SEQ ID NO:2.

The parent polypeptide may have at least 80%, such as at least e.g. 80%, 85%, 95%, 97%, 98%, 99% sequence identity with the mature polypeptide of SEQ ID NO:2 (camel chymosin) or the mature polypeptide of SEQ ID NO: 1 (bovine chymosin).

In a closely related aspect, the isolated chymosin polypeptide variant characterized in that (a) the isolated chymosin polypeptide variant has a C/P value that is at least 200% of the C/P value of isolated camel chymosin characterized by the mature polypeptide of SEQ ID NO:2; and (b) the isolated chymosin polypeptide variant cleaves αS1-casein with a frequency of less than 80% of the frequency of αS1-casein cleavage of isolated camel chymosin characterized by the mature polypeptide of SEQ ID NO:2, wherein αS1-casein cleavage is determined by quantifying αS1-casein peptides obtained by incubating skim milk with the chymosin variant or the camel chymosin, wherein quantification is carried out by RP-HPLC coupled to an ESI-Q-TOF mass spectrometer comprises one or more of the following substitutions, wherein the substitution is specified in relation to the amino acid sequence of the mature polypeptide of SEQ ID NO:2: Y11I, Y11V, L12M, K19T, V51L, R61S, H76Q, E83S, I96L, L105E, D144Q, Q162S, S164G, M165E, L166V, L180I, V203A, L221I, S226T, T239S, R242E, G251D, G251W, L253I, V260T, I263L, R266V, S273Y, Q288E, G289S, E294Q, Y307F, V309I, R316L and/or V317L.

Additionally the isolated chymosin polypeptide with reduced αS1-casein cleavage activity described immediately above may comprise one or more of the combinations of the following substitutions and wherein each substitution is specified in relation to the amino acid sequence of the mature polypeptide of SEQ ID NO:2:

Y21S+H76Q+Y307F+V317L,
R61S+L166V+T239S,
V32L+E294Q+R316L+V317L,
S226T+G244D+I263L+G289S,
V203A+V248I+G251W+L253I+Y268F,
D59N+L222I+G251D+E83S+Q162S,
D59N+L222I+G251D+Y21S+L215V+L105E,
D59N+L222I+G251D+H76Q+L105E+V260T,
D59N+L222I+G251D+V203A+R266V+F223A,
L12M+D59N+H76Q+S154A+M165E+V203A+L222I+G251D+V309I,
L12M+V51L+H76Q+M165E+G251D,
L12M+V51L+D59N+H76Q+L166V+L222I+G251D,
L12M+D59N+H76Q+D144Q+M165E+V203A+L222I,
L12M+K19T+D59N+H76Q+S154A+M165E+V198I+L222I+G251D,
L12M+V51L+D59N+F66Y+H76Q+M165E+V203A+L222I+G251W,
V51L+D59N+H76Q+M165E+L180I+L222I+G251D+E262T,
L12M+D59N+H76Q+M165E+G251D+Q288E+V309I+K321P,
D59N+H76Q+I96L+L130I+S164G+L222I+R242E+G251D,
H76Q+I96L+S164G+L222I+R242E+G251D+S273Y,
K19T+D59N+H76Q+I96L+S164G+L166V+L222I+G251D+S273Y,
H76Q+S164G+L166V+L222I+R242E+G251D+S273Y,
Y21S+H76Q+S164G+L222I+R242E+G251D+S273Y,
D59N+H76Q+I96L+S132A+S164G+L222I+S226T+G251D+S273Y,
D59N+H76Q+I96L+S132A+S164G+L166V+L222I+G251D+S273Y,
K19T+D59N+H76Q+S164G+L222I+N249D+S273Y,
H76Q+S164G+L222I+N249D+G251D+S273Y+V309I,
H76Q+I96L+S164G+G251D+S273Y+V309I,
K19T+D59N+H76Q+S164G+R242E+N249D+G251D+S273Y,
Y21S+D59N+H76Q+S164G+L222I+S226T+G251D+S273Y+V309I
D59N+H76Q+I96L+S164G+L222I+S226T+N249D+G251D+S273Y,
H76Q+S164G+L166V+L222I+S226T+S273Y,
D59N+H76Q+L130I+S164G+L166V+L222I+G251D+S273Y+V309I,
D59N+H76Q+S164G+L222I+S226T+R242E,
K19T+D59N+I96L+S164G+L222I+G251D,
D59N+H76Q+I96L+S164G+L222I+S226T+G251D+S273Y+V309I,
D59N+H76Q+L130I+S164G+G251D+V309I,
D59N+H76Q+L130I+L166V+L222I+N249D+G251D+S273Y,
Y21S+D59N+H76Q+I96L+S164G+L222I+N249D+G251D+S273Y,
K19T+D59N+S164G+L166V+L222I+S226T+G251D+S273Y,
D59N+H76Q+L130I+S132A+S164G+L222I+R242E+G251D+S273Y,
K19T+Y21S+H76Q+S164G+L222I+G251D+S273Y,
D59N+H76Q+S164G+L222I+R242E+S273Y+V309I,
K19T+Y21S+D59N+H76Q+S132A+S164G+L222I+G251D+S273Y,
K19T+D59N+H76Q+L130I+S164G+L222I+S226T+G251D+S273Y,
D59N+H76Q+S164G+L166V+L222I+N249D+G251D+S273Y+V309I,
K19T+Y21S+D59N+H76Q+L130I+S164G+L222I+S273Y,
Y21S+D59N+S164G+L222I+R242E+G251D+S273Y+V309I,
K19T+D59N+H76Q+L166V+L222I+R242E+G251D+S273Y,
D59N+S132A+S164G+L222I+R242E+N249D+G251D+S273Y,
D59N+H76Q+I96L+L130I+S164G+L222I+N249D+G251D+S273Y,
Y21S+D59N+H76Q+S164G+L166V+N249D+G251D+S273Y,
H76Q+S132A+S164G+L222I+N249D+G251D,
D59N+H76Q+S132A+S164G+L166V+S273Y,
K19T+D59N+H76Q+S132A+L222I+G251D+S273Y+V309I,
H76Q+L130I+L222I+S226T+G251D+S273Y,

Y21S+D59N+H76Q+I96L+L222I+S273Y,
Y11I+K19T+D59N+E83S+I96L+S164G+L222I+N249D,
Y11I+K19T+I96L+S164G+L222V+R242E+G251D,
Y11V+K19T+I96L+S164G+L166V+L222I+R242E,
Y11V+E83S+I96L+S164G+L222I+R242E+G251D+L253I+I263L,
Y11V+I96L+S164G+L222I+R242E+N249D+L253I+I263L,
K19S+I96L+S164G+L166V+L222I+R242E,
K19T+I96L+S164G+L166V+L222I+R242E+N249D+I263L,
Y11V+K19T+D59N+I96L+S164N+L166I+L222I+G251D,
H76Q+I96L+S164G+L222I+R242E+G251D+S273Y,
Y11V+K19T+E83S+I96L+S164G+L166V+L222I+R242E+G251D,
Y11V+E83S+I96L+S164G+L222I+R242E+L253I+I263L,
Y11V+K19T+D59N+I96L+S164G+L166V+L222I+R242E+G251D+L253I,
K19T+D59N+I96V+S164G+L166V+L222I+R242E+I263L,
Y11V+D59N+I96L+S164G+L222I+G251D+L253V,
I96L+S164G+L166V+L222I+R242E+N249D+I263L,
K19S+D59N+I96L+S164G+L222I+R242E+N249E+G251D,
H76Q+I96L+S164G+L222I+R242E+G251D,
Y11I+K19T+D59N+S164G+L222I+G251D+I263V,
K19T+I96L+S164G+L166V+L222I+R242E+N249D+G251D+I263V,
K19T+E83S+I96L+S164G+L222I+R242E+G251D+L253I,
I96L+S164G+L222I+R242E+N249D+G251D+I263L,
K19T+D59N+I96L+S164G+L166V+L222I+R242D+G251D+L253I,
D59N+I96L+S164G+L222I+R242E+L253I+I263L,
K19T+I96L+S164G+L166V+L222I+N249D+I263L,
K19T+D59N+I96L+S164G+L166I+L222I+R242D+G251D+I263V,
K19T+D59N+I96L+S164G+L222V+R242E+N249D+L253I,
K19T+D59N+I96L+S164G+L166I+L222I+R242E+N249D,
K19T+E83S+I96L+S164G+L222I+R242E+N249D+G251D+L253I,
I96L+S164G+L222I+R242E+G251D+S273Y,
K19T+E83T+I96L+S164G+L222I+R242E+L253V,
K19T+I96L+S164G+R242E+L253I,
K19T+D59N+I96L+S164G+L222I+N249E+G251D+L253V+I263L,
K19T+D59N+I96L+S164G+L222V+N249E+G251D+I263V,
I96L+S164G+L222I+R242E+G251D,
K19T+I96L+S164N+L222I+R242E+I263L,
K19T+E83S+I96L+S164G+L166V+L222I+R242E+N249D+G251D+L253I,
K19T+D59N+E83T+S164G+L166V+L222I+R242D+G251D,
K19T+D59N+I96L+S164G+L222I+G251D,
D59N+I96L+L166V+L222I+R242E+G251D,
Y11I+K19T+D59N+I96V+L222I+R242D+G251D,
K19T+I96V+S164G+L222I+N249D+G251D+L253I,
H76Q+N100Q+N291Q,
R67Q+L130I+M157L+D158S+R242E+N291Q,
V32L+R67Q+L130I+M157L+K231N+M256L,
R67Q+V136I+M157L+L222I+V248I,
Y11V+R67Q+L130I+M157L+L222I+R242E,
R67Q+I96L+N100Q+L130I+M157L+N292H.
Y11I+D59N+I96L+S164G+L166V+L222V+R242E+G251D+L253I,
Y11I+D59N+I96L+S164G+L166V+L222V+R242E+G251D,
Y11I+D59N+I96L+S164G+L166V+L222V+R242E+N249E+G251D,
Y11V+K19T+D59N+I96L+S164G+L166V+L222V+R242E+N249E+G251D,
Y11I+I96L+S164G+L166V+L222V+R242E+N249E+G251D,
Y11V+K19T+I96L+L166V+L222V+R242E+G251D,
Y11V+K19T+D59N+I96L+S164G+L166I+L222V+R242E+N249E+G251D+L253I,
Y11I+K19T+D59N+I96L+S164G+L166V+L222V+R242E+N249E+G251D,
Y11I+K19T+D59N+I96L+S164G+L166V+L222I+R242E+N249E+G251D,
Y11V+K19T+D59N+I96L+S164G+L166V+L222V+R242E+N249E+L253I,
Y11V+K19T+D59N+I96L+L166V+L222V+R242E+N249E+G251D+L253I,
Y11V+K19T+D59N+I96L+S164G+L166V+L222I+R242E+N249E,
Y11V+K19T+D59N+I96L+S164G+L166V+L222V+R242E+G251D,
Y11I+K19T+D59N+I96L+S164G+L166V+R242E+G251D,
Y11I+K19T+D59N+I96L+S164G+L166I+L222I+R242E+G251D,
Y11V+K19T+I96L+S164G+L166V+L222V+R242E+N249E+G251D,
Y11I+K19T+D59N+I96L+S164G+L166I+L222V+R242E+N249E+G251D,
Y11V+D59N+I96L+S164G+L166I+L222I+R242E+G251D,
Y11V+K19T+D59N+I96L+S164G+L166I+L222V+R242E+N249E+G251D,
Y11I+K19T+D59N+I96L+S164G+L222I+R242E,
Y11I+K19T+I96L+S164G+L166V+R242E+N249E+G251D,
Y11I+I96L+S164G+L222I+R242E,
Y11I+K19T+D59N+I96L+S164G+L222I+R242E+N249E+G251D,
Y11V+D59N+I96L+S164G+L166I+L222V+R242E+G251D+L253I,
Y11I+K19T+D59N+I96L+L222V+R242E+N249E+G251D,
Y11V+K19T+D59N+I96L+S164G+L166I+L222I+R242E+N249E+G251D,
Y11V+K19T+D59N+I96L+S164G+L222I+R242E+N249E+G251D,
Y11I+D59N+I96L+S164G+L222I+R242E+G251D,
Y11V+K19T+D59N+I96L+S164G+L166I+R242E+N249E+G251D+L253I,
Y11I+D59N+I96L+S164G+L222V+R242E+N249E+G251D,
Y11I+K19T+S164G+L166I+L222V+R242E+N249E+G251D,
Y11V+K19T+D59N+S164G+L166V+L222I+R242E+N249E+G251D,
Y11V+K19T+D59N+I96L+S164G+L166V+R242E,
Y11I+K19T+D59N+I96L+S164G+L222V+R242E+N249E,
Y11V+K19T+D59N+I96L+S164G+L222V+R242E+G251D,

Y11V+K19T+D59N+I96L+S164G+R242E+G251D,
Y11V+K19T+D59N+I96L+S164G+L166I+L222V+
R242E+G251D,
Y11I+I96L+L222V+R242E+N249E+G251D,
Y11I+K19T+D59N+S164G+L166I+L222V+R242E+
G251D,
Y11V+K19T+D59N+I96L+S164G+L222V+R242E+
N249E+G251D,
Y11V+K19T+D59N+I96L+L222V+R242E+G251D,
Y11V+K19T+D59N+S164G+L166I+L222I+R242E+
G251D,
Y11V+K19T+D59N+L166V+L222I+R242E+N249E+
G251D+L253I,
Y11V+K19T+I96L+L222V+R242E+N249E+G251D or
Y11I+K19T+L222V+R242E+N249E+G251D.

Preferred Variants with Increased αS1-Casein Cleavage Activity

Preferred isolated chymosin polypeptide variants of present invention comprise variants characterized in that (a) the isolated chymosin polypeptide variant has a C/P value that is at least 200% of the C/P value of isolated camel chymosin characterized by the mature polypeptide of SEQ ID NO:2; and (b) the isolated chymosin polypeptide variant cleaves αS1-casein with a frequency of more than 115% of the frequency of αS1-casein cleavage of isolated camel chymosin polypeptide characterized by the mature polypeptide of SEQ ID NO:2, wherein αS1-casein cleavage is determined by quantifying αS1-casein peptides obtained by incubating skim milk with the chymosin variant or the camel chymosin, wherein quantification is carried out by RP-HPLC coupled to an ESI-Q-TOF mass spectrometer.

In preferred aspects of the isolated chymosin polypeptide variants cleave αS1-casein with a frequency of at least 125%, at least 130%, at least 140%, at least 145% or at least 150% of the frequency of αS1-casein cleavage of isolated mature camel chymosin characterized by the mature polypeptide of SEQ ID NO:2. The isolated chymosin polypeptide variants having increased αS1-casein cleavage activity have a C/P value that is at least 200% of the C/P value of isolated camel chymosin polypeptide characterized by the mature polypeptide of SEQ ID NO:2, including C/P value that is at least 200%, at least 300%, at least 500%, at least 900%, at least 1200% or at least 1400% of the C/P value of isolated camel chymosin polypeptide characterized by the mature polypeptide of SEQ ID NO:2. The parent polypeptide may have at least 80%, such as at least e.g. 80%, 85%, 95%, 97%, 98%, 99% sequence identity with the mature polypeptide of SEQ ID NO:2 (camel chymosin) or the mature polypeptide of SEQ ID NO: 1 (bovine chymosin).

In a closely related aspect, the isolated chymosin polypeptide variant characterized in that (a) the isolated chymosin polypeptide variant has a C/P value that is at least 200% of the C/P value of isolated camel chymosin characterized by the mature polypeptide of SEQ ID NO:2; and (b) the isolated chymosin polypeptide variant cleaves αS1-casein with a frequency of more than 115% of the frequency of αS1-casein cleavage of isolated camel chymosin polypeptide characterized by the mature polypeptide of SEQ ID NO:2, wherein αS1-casein cleavage is determined by quantifying αS1-casein peptides obtained by incubating skim milk with the chymosin variant or the camel chymosin, wherein quantification is carried out by RP-HPLC coupled to an ESI-Q-TOF mass spectrometer comprises one or more of the following substitutions, wherein the substitution is specified in relation to the amino acid sequence of the mature polypeptide of SEQ ID NO:2: V32L, I45V, N50K, G70D, G70N, D98V, N100Q, V136I, M142I, H146R, S154A, V155F, M157L, D158S, V198I, I200V, F223V, K231N, G244D, V248I, R254S, M256L, V259I, E262T, D267Q, D279E, T284S, N291Q N292H, L295K, and/or K321P.

Additionally the isolated chymosin polypeptide with increased αS1-casein cleavage activity described immediately above may comprise one or more of the combinations of the following substitutions and wherein each substitution is specified in relation to the amino acid sequence of the mature polypeptide of SEQ ID NO:2:
G70D+S74F+D158S+R254S+S277N,
L130I+M142I+I200V+V259I+E294Q,
Y21S+R61S+H146R,
R61S+G163E+M256L+S277N,
D59N+S271P+T284S,
V248I+S226T+E294Q,
S74F+G244D+S271P,
V221K+V248I+S255Y,
V183I+G251W+M256L,
R61Q+V136I+Y268F+T284S+Y307F,
N50K+D158S+V203A+E294Q,
D98V+G251D+M256L+V259I,
V183I+V248I+G244D+T284S,
N50K+R61S+Y127F+G244D+G251D,
I96L+F223V+G244D+R254S+M256L,
H146R+D158S+S273Y,
S74F+V259I+Y268F,
G70N+D98V+V136I,
I96L+M142I+R145Q+H146R,
V32L+G163E+T186S+Q188E+L295K,
R61Q+V136I+Y268F+T284S+Y307F,
S132A+Q188E+F223V,
I200V+G251D+G289S,
N50K+D158S+V203A+E294Q,
F223V+G251W+S273Y+D279E,
D59N+L222I+G251D+V32L+L12M+T284S,
D59N+L222I+G251D+V155F+E262T+V32L,
D59N+L222I+G251W+S154A+V203A,
D59N+L222I+G251D+V32L+K321P+V260T,
D59N+L222I+G251D+V198I+V203A+K321P,
D59N+L222I+G251D+S273Y+T284S+D267Q
V32L+N100Q+N291Q,
N292H+N100Q+N291Q,
V221K+N100Q+N291Q,
I297A+N100Q+N291Q,
R67Q+N100Q+L130I+M157L+L222I+K231N,
R67Q+L130I+V248I+M256L+N292H,
V32L+R67Q+L130I+K231N+N292H,
L130I+M157L+V248I+M256L+N291Q,
V32L+R67Q+V136I+M157L+N291Q,
R67Q+L130I+K231N+V248I+N291Q,
V32L+R67Q+G70D+N100Q+M157L,
R67Q+N100Q+L130I+D158S+V248I,
R67Q+N100Q+L130I+M157L+K231N+N291Q,
R67Q+N100Q+L130I+M157L+V248I+N291Q and/or
N100Q+L130I+S132A+M157L+K231.

The isolated chymosin polypeptide variants of the present invention maintain high overall sequence identity to the natural chymosin polypeptide. For example, the polypeptide variants of the present invention preferably have at least 80% sequence identity with the mature polypeptide of SEQ ID NO:2, including at least 85%, 95%, 97%, 98% or 99% sequence identity with the mature polypeptide of SEQ ID NO:2 (camel chymosin).

As discussed above—based on e.g. the computer sequence alignment programs discussed herein—it is routine work for the skilled person to determine the herein relevant amino acid position of a herein relevant chymosin polypeptide of interest (e.g. camel, sheep, bovine etc).

For instance, a camel chymosin variant with e.g. 5-10 alterations (e.g. substitutions) as compared to wildtype camel chymosin polypeptide of SEQ ID NO: 2 will still be a parent polypeptide that has at least 65% sequence identity with the mature polypeptide of SEQ ID NO: 2 (camel).

Said in other words, a herein relevant isolated chymosin polypeptide variant may comprise alterations (e.g. substitutions) in other position than the positions claimed herein. As understood by the skilled person in the present context—herein relevant sequence identity percentages of e.g. mature sheep, C. bactrianus, camel, pig or rat chymosin with the mature polypeptide of SEQ ID NO: 1 (bovine chymosin—i.e. amino acid positions 59 to 381 of SEQ ID NO: 1) are relatively similar to above mentioned sequence identity percentages.

In a preferred embodiment—the parent polypeptide has at least 92% sequence identity with the mature polypeptide of SEQ ID NO: 2 (camel chymosin), more preferably the parent polypeptide has at least 95% sequence identity with the mature polypeptide of SEQ ID NO: 2 (camel chymosin) and even more preferably the parent polypeptide has at least 97% sequence identity with the mature polypeptide of SEQ ID NO: 2 (camel chymosin). It may be preferred that the parent polypeptide is the mature polypeptide of SEQ ID NO: 2 (Camel chymosin).

It may be preferred that the isolated camel chymosin variant comprises less than 30 amino acid alterations (e.g. substitutions) as compared to the mature polypeptide of SEQ ID NO: 2 (camel chymosin) or it may be preferred that the isolated camel chymosin variant comprises less than 20 amino acid alterations (e.g. substitutions) as compared to the mature polypeptide of SEQ ID NO: 2 (camel chymosin) or it may be preferred that the isolated camel chymosin variant comprises less than 10 amino acid alterations (e.g. substitutions) as compared to the mature polypeptide of SEQ ID NO: 2 (camel chymosin) or it may be preferred that the isolated camel chymosin variant comprises less than 5 amino acid alterations (e.g. substitutions) as compared to the mature polypeptide of SEQ ID NO: 2 (camel chymosin).

As understood by the skilled person in the present context—the term "the isolated variant polypeptide has less than 100% sequence identity with the mature polypeptide of SEQ ID NO: 2 (camel chymosin)" above relates to that the herein described isolated camel chymosin variant shall not have a polypeptide sequence that is 100% identical to the public known mature wildtype camel chymosin sequence of SEQ ID NO: 2.

It may be preferred that at least one alteration is a substitution—i.e. a herein relevant preferred embodiment relates to an isolated chymosin polypeptide variant, wherein the alteration is comprising a substitution in at least one amino acid position corresponding to any of positions claimed herein.

Preferably, the parent polypeptide has at least 80%, such as e.g. 85%, 90%, 95%, 97%, 98%, or 99% sequence identity with the mature polypeptide of SEQ ID NO: 1 (bovine chymosin) and/or SEQ ID NO: 2 (camel chymosin).

Just as an example—a herein suitable relevant parent polypeptide could e.g. be bovine chymosin A—as known in the art bovine chymosin A may only have one amino acid difference as compared to bovine chymosin B of SEQ ID NO: 1 herein.

As understood by the skilled person in the present context—a herein relevant parent polypeptide having chymosin activity may already e.g. be a variant of e.g. a corresponding wildtype chymosin.

For instance, a bovine chymosin variant with e.g. 5-10 alterations (e.g. substitutions) as compared to mature wildtype bovine chymosin polypeptide of SEQ ID NO: 1 will still be a parent polypeptide that has at least 95% sequence identity with the mature polypeptide of SEQ ID NO: 1 (Bovine chymosin).

Said in other words and in general—a herein relevant isolated chymosin polypeptide variant may comprise alterations (e.g. substitutions) in other positions than the positions claimed herein.

As understood by the skilled person in the present context—an isolated chymosin variant may comprise alterations (e.g. substitutions) in other amino acid positions than given above.

For instance, a bovine chymosin variant with e.g. 5-10 alterations (e.g. substitutions) as compared to wildtype bovine chymosin polypeptide of SEQ ID NO: 1 will still be a parent polypeptide that has at least 95% sequence identity with the mature polypeptide of SEQ ID NO: 1 (Bovine chymosin).

It may be preferred that the isolated bovine chymosin variant comprises less than 30 amino acid alterations (e.g. substitutions) as compared to the mature polypeptide of SEQ ID NO: 1 (bovine chymosin) or it may be preferred that the isolated bovine chymosin variant comprises less than 20 amino acid alterations (e.g. substitutions) as compared to the mature polypeptide of SEQ ID NO: 1 (bovine chymosin) or it may be preferred that the isolated bovine chymosin variant comprises less than 10 amino acid alterations (e.g. substitutions) as compared to the mature polypeptide of SEQ ID NO: 1 (bovine chymosin) or it may be preferred that the isolated bovine chymosin variant comprises less than 5 amino acid alterations (e.g. substitutions) as compared to the mature polypeptide of SEQ ID NO: 1 (bovine chymosin).

Said in other words—a mature parent chymosin polypeptide (e.g. sheep or pig) that has at least 65% sequence identity with the mature Bovine chymosin is believed to be sufficient structural identical to e.g. Bovine or Camel chymosin in order to be herein relevant—i.e. in the present context a mature parent chymosin polypeptide (e.g. from e.g. sheep or rat) that has at least 80% sequence identity with the mature polypeptide of SEQ ID NO: 2 (camel chymosin) may herein be seen as sufficient structural related to e.g. bovine or camel chymosin in order to be improved by making a variant in any of the amino acid positions as described herein.

The camel chymosin polypeptide of SEQ ID NO: 2 has 84% sequence identity with the bovine polypeptide of SEQ ID NO: 1 (i.e. the complete SEQ ID NO: 1 from position 1 to 381, which includes pre and pro sequence).

A Method for Making an Isolated Chymosin Polypeptide Variant

The present invention also relates to a method for making an isolated chymosin polypeptide variant characterized in that (a) the isolated chymosin polypeptide variant has a C/P value that is at least 200% of the C/P value of isolated camel chymosin characterized by the mature polypeptide of SEQ ID NO:2; and (b) the isolated chymosin polypeptide variant cleaves αS1-casein with a frequency of less than 80% of the frequency of αS1-casein cleavage of isolated camel chymosin characterized by the mature polypeptide of SEQ ID NO:2, wherein αS1-casein cleavage is determined by quantifying αS1-casein peptides obtained by incubating skim milk with the chymosin variant or the camel chymosin, wherein quantification is carried out by RP-HPLC coupled to an ESI-Q-TOF mass spectrometer, the method comprising the following steps:

(a): making an alteration at one or more positions in the DNA sequence encoding the mature polypeptide of SEQ ID NO:2, wherein the alteration comprises one or more of the following substitutions, wherein the substitution is specified in relation to the amino acid sequence of the mature polypeptide of SEQ ID NO:2: Y11I, Y11V, L12M, K19T, V51L, R61S, H76Q, E83S, I96L, L105E, D144Q, Q162S, S164G, M165E, L166V, L180I, V203A, L222I, S226T, R242E, G251W, L253I, V260T, I263L, R266V, S273Y, T239S, G251D, Q288E, G289S, E294Q, Y307F, V309I, R316L, V317L;

(b): producing and isolating the altered polypeptide of step (a).

In a related aspect, the present invention also relates to a method for making an isolated chymosin polypeptide variant characterized in that (a) the isolated chymosin polypeptide variant has a C/P value that is at least 200% of the C/P value of isolated camel chymosin characterized by the mature polypeptide of SEQ ID NO:2; and (b) the isolated chymosin polypeptide variant cleaves αS1-casein with a frequency of more than 115% of the frequency of αS1-casein cleavage of isolated camel chymosin polypeptide characterized by the mature polypeptide of SEQ ID NO:2, wherein αS1-casein cleavage is determined by quantifying αS1-casein peptides obtained by incubating skim milk with the chymosin variant or the camel chymosin, wherein quantification is carried out by RP-HPLC coupled to an ESI-Q-TOF mass spectrometer, the method comprising the following steps:

(a): making an alteration at one or more positions in the DNA sequence encoding the mature polypeptide of SEQ ID NO:2, wherein the alteration comprises one or more of the following substitutions, wherein the substitution is specified in relation to the amino acid sequence of the mature polypeptide of SEQ ID NO:2: V32L, I45V, N50K, G70D, G70N, D98V, N100Q, V136I, M142I, H146R, S154A, V155F, M157L, D158S, V198I, I200V, F223V, K231N, G244D, V248I, R254S, M256L, V259I, E262T, D267Q, D279E, T284S, N291Q N292H, L295K, and/or K321P;

(b): producing and isolating the altered polypeptide of step (a).

As discussed above—as known in the art, the skilled person may, based on his common general knowledge, routinely produce and purify chymosin and chymosin variants.

Said in other words, once the skilled person is in possession of a herein relevant parent polypeptide having chymosin activity of interest (e.g. from bovines, camels, sheep, pigs, or rats) and the herein disclosed teachings it is routine work for the skilled person to make a variant of such a parent chymosin of interest.

An example of a suitable method to produce and isolate a chymosin (variant or parent) may be by well-known e.g. fungal recombinant expression/production based technology as e.g. described in WO02/36752A2 (Chr. Hansen).

It is also routine work for the skilled person to make alteration at one or more positions in a parent polypeptide having chymosin activity, wherein the alteration is comprising a substitution, a deletion or an insertion in at least one amino acid position as disclosed herein. As known to the skilled person—this may e.g. be done by so-called site directed mutagenesis and recombinant expression/production based technology.

It is also routine work for the skilled person to determine if a herein relevant parent polypeptide (e.g. camel or bovine wildtype chymosin) and/or a herein relevant variant has chymosin activity or not.

As known in the art—chymosin specificity may be determined by the so-called C/P value, which is determined by dividing the specific clotting activity (C) with the proteolytic activity (P). As known in the art—a higher C/P value implies generally that the loss of protein during e.g. cheese manufacturing due to non-specific protein degradation is reduced, i.e. the yield of cheese is improved.

As also known in the art, αS1-casein cleavage and αS1-casein (including αS1(1-23)) formation may be determined using standard methods available to the person skilled in the art.

Additional methods are provided in the examples.

A Method for Making a Milk Based Product

As discussed above—an isolated chymosin polypeptide variant as described herein may be used according to the art—e.g. to make a milk based product of interest (such as e.g. a cheese product).

As discussed above—an aspect of the invention relates to a method for making a food or feed product comprising adding an effective amount of the isolated chymosin polypeptide variant as described herein to the food or feed ingredient(s) and carrying our further manufacturing steps to obtain the food or feed product.

Preferably, the food or feed product is a milk-based product and wherein the method comprises adding an effective amount of the isolated chymosin polypeptide variant as described herein to milk and carrying our further manufacturing steps to obtain the milk based product.

For example, the chymosin polypeptide variant of the present invention may be added to a milk-based product after fermentation of the milk. In one aspect the chymosin polypeptide variant of the present invention is added for coagulation of a fermented milk product as part of a method of producing cheese.

The milk may e.g. be soy milk, sheep milk, goat milk, buffalo milk, yak milk, *lama* milk, camel milk or cow milk.

The milk based product may e.g. be a fermented milk product such as a quark or a cheese.

Food and Feed Products

The present invention also provides food and feed products comprising a chymosin polypeptide variant of the present invention or a chymosin polypeptide variant obtainable according to a method of the present invention. The food and feed product is preferably a fermented food product, such as a fermented milk product, including cheese and quark.

In an Alternative, Yet Related Aspect, the Invention Relates to the Items Listed Below:

Item 1. A method for making an isolated chymosin polypeptide variant having an altered αS1-casein cleavage frequency compared to the parent polypeptide, the method comprising the steps:

(a): making an alteration at one or more positions in a parent polypeptide, wherein the alteration is comprising a substitution, a deletion or an insertion in at least one amino acid position corresponding to any of positions: Y11I, Y11V, L12M, K19T, V51L, R61S, H76Q, E83S, I96L, L105E, D144Q, Q162S, S164G, M165E, L166V, L180I, V203A, L222I, S226T, T239S, R242E, G251D, G251W, L253I, V260T, I263L, R266V, S273Y, Q288E, G289S, E294Q, Y307F, V309I, R316L, V317L, V32L, I45V, N50K, G70D, G70N, D98V, N100Q, V136I, M142I, H146R, S154A, V155F, M157L, D158S, V198I, I200V, F223V, K231N, G244D, V248I, R254S, M256L, V259I, E262T, D267Q, D279E, T284S, N291Q N292H, L295K, and/or K321P, (b): producing and isolating the altered polypeptide of step (a), and wherein:

(i): the amino acid position of the parent polypeptide is determined by an alignment of the parent polypeptide with the mature polypeptide of SEQ ID NO: 2 (camel chymosin); and (ii): the parent polypeptide has at least 65% sequence identity with the mature polypeptide of SEQ ID NO: 1 (bovine chymosin) and/or at least 65% sequence identity with the mature polypeptide of SEQ ID NO: 2 (camel chymosin).

Item 2. The method according to item 1, wherein the isolated chymosin polypeptide variant has:
- a chymosin activity giving a lower αS1-casein cleavage frequency as compared to the αS1-casein cleavage frequency of bovine chymosin comprising the mature polypeptide of SEQ ID NO: 1 and/or
- a chymosin activity giving a lower αS1-casein cleavage frequency as compared to the αS1-casein cleavage frequency of camel chymosin comprising the mature polypeptide of SEQ ID NO: 2.

Item 3. The method for making an isolated chymosin polypeptide variant of item 2, wherein the alteration is one or more of the substitutions: Y11I, Y11V, L12M, K19T, V51L, R61S, H76Q, E83S, I96L, L105E, D144Q, Q162S, S164G, M165E, L166V, L180I, V203A, L222I, S226T, T239S, R242E, G251D, G251W, L253I, V260T, I263L, R266V, S273Y, Q288E, Q289S, E294Q, Y307F, V309I, R316L and/or V317L.

Item 4. The method according to any of items 2 and 3 wherein the isolated chymosin polypeptide variant comprise an alteration in one or more of the combinations of positions comprising the positions corresponding to:

Y21S+H76Q+Y307F+V317L,
R61S+L166V+T239S,
V32L+E294Q+R316L+V317L,
S226T+G244D+I263L+G289S,
V203A+V248I+G251W+L253I+Y268F,
D59N+L222I+G251D+E83S+Q162S,
D59N+L222I+G251D+Y21S+L215V+L105E,
D59N+L222I+G251D+H76Q+L105E+V260T,
D59N+L222I+G251D+V203A+R266V+F223A,
L12M+D59N+H76Q+S154A+M165E+V203A+L222I+G251D+V309I,
L12M+V51L+H76Q+M165E+G251D,
L12M+V51L+D59N+H76Q+L166V+L222I+G251D,
L12M+D59N+H76Q+D144Q+M165E+V203A+L222I,
L12M+K19T+D59N+H76Q+S154A+M165E+V198I+L222I+G251D,
L12M+V51L+D59N+F66Y+H76Q+M165E+V203A+L222I+G251W,
V51L+D59N+H76Q+M165E+L180I+L222I+G251D+E262T,
L12M+D59N+H76Q+M165E+G251D+Q288E+V309I+K321P,
D59N+H76Q+I96L+L130I+S164G+L222I+R242E+G251D,
H76Q+I96L+S164G+L222I+R242E+G251D+S273Y,
K19T+D59N+H76Q+I96L+S164G+L166V+L222I+G251D+S273Y,
H76Q+S164G+L166V+L222I+R242E+G251D+S273Y,
Y21S+H76Q+S164G+L222I+R242E+G251D+S273Y,
D59N+H76Q+I96L+S132A+S164G+L222I+S226T+G251D+S273Y,
D59N+H76Q+I96L+S132A+S164G+L166V+L222I+G251D+S273Y,
K19T+D59N+H76Q+S164G+L222I+N249D+S273Y,
H76Q+S164G+L222I+N249D+G251D+S273Y+V309I,
H76Q+I96L+S164G+G251D+S273Y+V309I,
K19T+D59N+H76Q+S164G+R242E+N249D+G251D+S273Y,
Y21S+D59N+H76Q+S164G+L222I+S226T+G251D+S273Y+V309I,
D59N+H76Q+I96L+S164G+L222I+S226T+N249D+G251D+S273Y,
H76Q+S164G+L166V+L222I+S226T+S273Y,
D59N+H76Q+L130I+S164G+L166V+L222I+G251D+S273Y+V309I,
D59N+H76Q+S164G+L222I+S226T+R242E,
K19T+D59N+I96L+S164G+L222I+G251D,
D59N+H76Q+I96L+S164G+L222I+S226T+G251D+S273Y+V309I,
D59N+H76Q+L130I+S164G+G251D+V309I,
D59N+H76Q+L130I+L166V+L222I+N249D+G251D+S273Y,
Y21S+D59N+H76Q+I96L+S164G+L222I+N249D+G251D+S273Y,
K19T+D59N+S164G+L166V+L222I+S226T+G251D+S273Y,
D59N+H76Q+L130I+S132A+S164G+L222I+R242E+G251D+S273Y,
K19T+Y21S+H76Q+S164G+L222I+G251D+S273Y,
D59N+H76Q+S164G+L222I+R242E+S273Y+V309I,
K19T+Y21S+D59N+H76Q+S132A+S164G+L222I+G251D+S273Y,
K19T+D59N+H76Q+L130I+S164G+L222I+S226T+G251D+S273Y,
D59N+H76Q+S164G+L166V+L222I+N249D+G251D+S273Y+V309I,
K19T+Y21S+D59N+H76Q+L130I+S164G+L222I+S273Y,
Y21S+D59N+S164G+L222I+R242E+G251D+S273Y+V309I,
K19T+D59N+H76Q+L166V+L222I+R242E+G251D+S273Y,
D59N+S132A+S164G+L222I+R242E+N249D+G251D+S273Y,
D59N+H76Q+I96L+L130I+S164G+L222I+N249D+G251D+S273Y,
Y21S+D59N+H76Q+S164G+L166V+N249D+G251D+S273Y,
H76Q+S132A+S164G+L222I+N249D+G251D,
D59N+H76Q+S132A+S164G+L166V+S273Y,
K19T+D59N+H76Q+S132A+L222I+G251D+S273Y+V309I,
H76Q+L130I+L222I+S226T+G251D+S273Y,
Y21S+D59N+H76Q+I96L+L222I+S273Y,
Y11I+K19T+D59N+E83S+I96L+S164G+L222I+N249D,
Y11I+K19T+I96L+S164G+L222V+R242E+G251D,
Y11V+K19T+I96L+S164G+L166V+L222I+R242E,
Y11V+E83S+I96L+S164G+L222I+R242E+G251D+L253I+I263L,
Y11V+I96L+S164G+L222I+R242E+N249D+L253I+I263L,
K19S+I96L+S164G+L166V+L222I+R242E,
K19T+I96L+S164G+L166V+L222I+R242E+N249D+I263L,
Y11V+K19T+D59N+I96L+S164N+L166I+L222I+G251D,
H76Q+I96L+S164G+L222I+R242E+G251D+S273Y,

Y11V+K19T+E83S+I96L+S164G+L166V+L222I+R242E+G251D,
Y11V+E83S+I96L+S164G+L222I+R242E+L253I+I263L,
Y11V+K19T+D59N+I96L+S164G+L166V+L222I+R242E+G251D+L253I,
K19T+D59N+I96V+S164G+L166V+L222I+R242E+I263L,
Y11V+D59N+I96L+S164G+L222I+G251D+L253V,
I96L+S164G+L166V+L222I+R242E+N249D+I263L,
K19S+D59N+I96L+S164G+L222I+R242E+N249E+G251D,
H76Q+I96L+S164G+L222I+R242E+G251D,
Y11I+K19T+D59N+S164G+L222I+G251D+I263V,
K19T+I96L+S164G+L166V+L222I+R242E+N249D+G251D+I263V,
K19T+E83S+I96L+S164G+L222I+R242E+G251D+L253I,
I96L+S164G+L222I+R242E+N249D+G251D+I263L,
K19T+D59N+I96L+S164G+L166V+L222I+R242D+G251D+L253I,
D59N+I96L+S164G+L222I+R242E+L253I+I263L,
K19T+I96L+S164G+L166V+L222I+N249D+I263L,
K19T+D59N+I96L+S164G+L166I+L222I+R242D+G251D+I263V,
K19T+D59N+I96L+S164G+L222V+R242E+N249D+L253I,
K19T+D59N+I96L+S164G+L166I+L222I+R242E+N249D,
K19T+E83S+I96L+S164G+L222I+R242E+N249D+G251D+L253I,
I96L+S164G+L222I+R242E+G251D+S273Y,
K19T+E83T+I96L+S164G+L222I+R242E+L253V,
K19T+I96L+S164G+R242E+L253I,
K19T+D59N+I96L+S164G+L222I+N249E+G251D+L253V+I263L,
K19T+D59N+I96L+S164G+L222V+N249E+G251D+I263V,
I96L+S164G+L222I+R242E+G251D,
K19T+I96L+S164N+L222I+R242E+I263L,
K19T+E83S+I96L+S164G+L166V+L222I+R242E+N249D+G251D+L253I,
K19T+D59N+E83T+S164G+L166V+L222I+R242D+G251D,
K19T+D59N+I96L+S164G+L222I+G251D,
D59N+I96L+L166V+L222I+R242E+G251D,
Y11I+K19T+D59N+I96V+L222I+R242D+G251D,
K19T+I96V+S164G+L222I+N249D+G251D+L253I,
R67Q+L130I+M157L+D158S+R242E+N291Q,
V32L+R67Q+L130I+M157L+K231N+M256L,
R67Q+V136I+M157L+L222I+V248I,
Y11V+R67Q+L130I+M157L+L222I+R242E,
R67Q+I96L+N100Q+L130I+M157L+N292H,
H76Q+N100Q+N291Q,
Y11I+D59N+I96L+S164G+L166V+L222V+R242E+G251D+L253I,
Y11I+D59N+I96L+S164G+L166V+L222V+R242E+G251D,
Y11I+D59N+I96L+S164G+L166V+L222V+R242E+N249E+G251D,
Y11V+K19T+D59N+I96L+S164G+L166V+L222V+R242E+N249E+G251D,
Y11I+I96L+S164G+L166V+L222V+R242E+N249E+G251D,
Y11V+K19T+I96L+L166V+L222V+R242E+G251D,
Y11V+K19T+D59N+I96L+S164G+L166I+L222V+R242E+N249E+G251D+L253I,
Y11I+K19T+D59N+I96L+S164G+L166V+L222V+R242E+N249E+G251D,
Y11I+K19T+D59N+I96L+S164G+L166V+L222I+R242E+N249E+G251D,
Y11V+K19T+D59N+I96L+S164G+L166V+L222V+R242E+N249E+L253I,
Y11V+K19T+D59N+I96L+L166V+L222V+R242E+N249E+G251D+L253I,
Y11V+K19T+D59N+I96L+S164G+L166V+L222I+R242E+N249E,
Y11V+K19T+D59N+I96L+S164G+L166V+L222V+R242E+G251D,
Y11I+K19T+D59N+I96L+S164G+L166V+R242E+G251D,
Y11I+K19T+D59N+I96L+S164G+L166I+L222I+R242E+G251D,
Y11V+K19T+I96L+S164G+L166V+L222V+R242E+N249E+G251D,
Y11I+K19T+D59N+I96L+S164G+L166I+L222V+R242E+N249E+G251D,
Y11V+D59N+I96L+S164G+L166I+L222I+R242E+G251D,
Y11V+K19T+D59N+I96L+S164G+L166I+L222V+R242E+N249E+G251D,
Y11I+K19T+D59N+I96L+S164G+L222I+R242E,
Y11I+K19T+I96L+S164G+L166V+R242E+N249E+G251D,
Y11I+I96L+S164G+L222I+R242E,
Y11I+K19T+D59N+I96L+S164G+L222I+R242E+N249E+G251D,
Y11V+D59N+I96L+S164G+L166I+L222V+R242E+G251D+L253I,
Y11I+K19T+D59N+I96L+L222V+R242E+N249E+G251D,
Y11V+K19T+D59N+I96L+S164G+L166I+L222I+R242E+N249E+G251D,
Y11V+K19T+D59N+I96L+S164G+L222I+R242E+N249E+G251D,
Y11I+D59N+I96L+S164G+L222I+R242E+G251D,
Y11V+K19T+D59N+I96L+S164G+L166I+R242E+N249E+G251D+L253I,
Y11I+D59N+I96L+S164G+L222V+R242E+N249E+G251D,
Y11I+K19T+S164G+L166I+L222V+R242E+N249E+G251D,
Y11V+K19T+D59N+S164G+L166V+L222I+R242E+N249E+G251D,
Y11V+K19T+D59N+I96L+S164G+L166V+R242E,
Y11I+K19T+D59N+I96L+S164G+L222V+R242E+N249E,
Y11V+K19T+D59N+I96L+S164G+L222V+R242E+G251D,
Y11V+K19T+D59N+I96L+S164G+R242E+G251D,
Y11V+K19T+D59N+I96L+S164G+L166I+L222V+R242E+G251D,
Y11I+I96L+L222V+R242E+N249E+G251D,
Y11I+K19T+D59N+S164G+L166I+L222V+R242E+G251D,
Y11V+K19T+D59N+I96L+S164G+L222V+R242E+N249E+G251D,
Y11V+K19T+D59N+I96L+L222V+R242E+G251D,
Y11V+K19T+D59N+S164G+L166I+L222I+R242E+G251D,
Y11V+K19T+D59N+L166V+L222I+R242E+N249E+G251D+L253I,
Y11V+K19T+I96L+L222V+R242E+N249E+G251D or
Y11I+K19T+L222V+R242E+N249E+G251D.

Item 5. The method according to item 1, wherein the isolated chymosin polypeptide variant has:
- a chymosin activity giving a higher αS1-casein cleavage frequency as compared to the αS1-casein cleavage frequency of bovine chymosin comprising the mature polypeptide of SEQ ID NO: 1 and/or
- a chymosin activity giving a higher αS1-casein cleavage frequency as compared to the αS1-casein cleavage frequency of camel chymosin comprising the mature polypeptide of SEQ ID NO: 2.

Item 6. The method for making an isolated chymosin polypeptide variant of item 5, wherein the alteration is one or more of the substitutions: V32L, I45V, N50K, G70D, G70N, D98V, N100Q, V136I, M142I, H146R, S154A, V155F, M157L, D158S, V198I, I200V, F223V, K231N, G244D, V248I, R254S, M256L, V259I, E262T, D267Q, D279E, T284S, N291Q N292H, L295K, and/or K321P.

Item 7. The method according to any of items 5 and 6 wherein the isolated chymosin polypeptide variant comprise an alteration in one or more of the combinations of positions comprising the positions corresponding to:
G70D+S74F+D158S+R254S+S277N,
L130I+M142I+I200V+V259I+E294Q,
Y21S+R61S+H146R,
R61S+G163E+M256L+S277N,
D59N+S271P+T284S,
V248I+S226T+E294Q,
S74F+G244D+S271P,
V221K+V248I+S255Y,
V183I+G251W+M256L,
R61Q+V136I+Y268F+T284S+Y307F,
N50K+D158S+V203A+E294Q,
D98V+G251D+M256L+V259I,
V183I+V248I+G244D+T284S,
N50K+R61S+Y127F+G244D+G251D,
I96L+F223V+G244D+R254S+M256L,
H146R+D158S+S273Y,
S74F+V259I+Y268F,
G70N+D98V+V136I,
I96L+M142I+R145Q+H146R,
V32L+G163E+T186S+Q188E+L295K,
R61Q+V136I+Y268F+T284S+Y307F,
S132A+Q188E+F223V,
I200V+G251D+G289S,
N50K+D158S+V203A+E294Q,
F223V+G251W+S273Y+D279E,
D59N+L222I+G251D+V32L+L12M+T284S,
D59N+L222I+G251D+V155F+E262T+V32L,
D59N+L222I+G251W+S154A+V203A,
D59N+L222I+G251D+V32L+K321P+V260T,
D59N+L222I+G251D+V198I+V203A+K321P,
D59N+L222I+G251D+S273Y+T284S+D267Q,
V32L+N100Q+N291Q,
N292H+N100Q+N291Q,
V221K+N100Q+N291Q,
I297A+N100Q+N291Q,
R67Q+N100Q+L130I+M157L+L222I+K231N,
R67Q+L130I+V248I+M256L+N292H,
V32L+R67Q+L130I+K231N+N292H,
L130I+M157L+V248I+M256L+N291Q,
V32L+R67Q+V136I+M157L+N291Q,
R67Q+L130I+K231N+V248I+N291Q,
V32L+R67Q+G70D+N100Q+M157L,
R67Q+N100Q+L130I+D158S+V248I,
R67Q+N100Q+L130I+M157L+K231N+N291Q,
R67Q+N100Q+L130I+M157L+V248I+N291Q and/or
N100Q+L130I+S132A+M157L+K231.

Item 8. The method for making an isolated chymosin polypeptide variant of any of items 1 to 7, wherein the parent polypeptide has at least 95% sequence identity with the mature polypeptide of SEQ ID NO: 2 (Camel chymosin).

Item 9. An isolated chymosin polypeptide variant comprising an alteration in one or more positions compared to a parent polypeptide having chymosin activity, wherein the alteration is comprising a substitution in at least one amino acid position corresponding to any of positions Y11I, Y11V, L12M, K19T, V51L, R61S, H76Q, E83S, I96L, L105E, D144Q, Q162S, S164G, M165E, L166V, L180I, V203A, L222I, S226T, T239S, R242E, G251D, G251W, L253I, V260T, I263L, R266V, S273Y, Q288E, G289S, E294Q, Y307F, V309I, R316L and/or V317L wherein (i): the amino acid position of the parent polypeptide is determined by an alignment of the parent polypeptide with the mature polypeptide of SEQ ID NO: 2 (camel chymosin) and (ii): the parent polypeptide has at least 65% sequence identity with the mature polypeptide of SEQ ID NO: 2 (camel chymosin);

wherein the isolated chymosin polypeptide variant cleaves αS1-casein with a lower frequency than the corresponding parent polypeptide.

Item 10. The isolated chymosin polypeptide variant of item 9, wherein the parent polypeptide has at least 80%, such as at least e.g. 80%, 85%, 95%, 97%, 98%, 99% sequence identity with the mature polypeptide of SEQ ID NO:2 (camel chymosin).

Item 11. An isolated chymosin polypeptide variant according to any of items 9 to 10, wherein the isolated chymosin polypeptide variant comprise an alteration in one or more of the combinations of positions comprising the positions corresponding to:
Y21S+H76Q+Y307F+V317L,
R61S+L166V+T239S,
V32L+E294Q+R316L+V317L,
S226T+G244D+I263L+G289S,
V203A+V248I+G251W+L253I+Y268F,
D59N+L222I+G251D+E83S+Q162S,
D59N+L222I+G251D+Y21S+L215V+L105E,
D59N+L222I+G251D+H76Q+L105E+V260T,
D59N+L222I+G251D+V203A+R266V+F223A,
L12M+D59N+H76Q+S154A+M165E+V203A+L222I+G251D+V309I,
L12M+V51L+H76Q+M165E+G251D,
L12M+V51L+D59N+H76Q+L166V+L222I+G251D,
L12M+D59N+H76Q+D144Q+M165E+V203A+L222I,
L12M+K19T+D59N+H76Q+S154A+M165E+V198I+L222I+G251D,
L12M+V51L+D59N+F66Y+H76Q+M165E+V203A+L222I+G251W,
V51L+D59N+H76Q+M165E+L180I+L222I+G251D+E262T,
L12M+D59N+H76Q+M165E+G251D+Q288E+V309I+K321P,
D59N+H76Q+I96L+L130I+S164G+L222I+R242E+G251D,
H76Q+I96L+S164G+L222I+R242E+G251D+S273Y,
K19T+D59N+H76Q+I96L+S164G+L166V+L222I+G251D+S273Y,
H76Q+S164G+L166V+L222I+R242E+G251D+S273Y,
Y21S+H76Q+S164G+L222I+R242E+G251D+S273Y,
D59N+H76Q+I96L+S132A+S164G+L222I+S226T+G251D+S273Y,
D59N+H76Q+I96L+S132A+S164G+L166V+L222I+G251D+S273Y, K19T+D59N+H76Q+S164G+L222I+N249D+S273Y,
H76Q+S164G+L222I+N249D+G251D+S273Y+V309I,
H76Q+I96L+S164G+G251D+S273Y+V309I,
K19T+D59N+H76Q+S164G+R242E+N249D+G251D+S273Y,
Y21S+D59N+H76Q+S164G+L222I+S226T+G251D+S273Y+V309I
D59N+H76Q+I96L+S164G+L222I+S226T+N249D+G251D+S273Y,
H76Q+S164G+L166V+L222I+S226T+S273Y,
D59N+H76Q+L130I+S164G+L166V+L222I+G251D+S273Y+V309I,
D59N+H76Q+S164G+L222I+S226T+R242E,
K19T+D59N+I96L+S164G+L222I+G251D,
D59N+H76Q+I96L+S164G+L222I+S226T+G251D+S273Y+V309I,
D59N+H76Q+L130I+S164G+G251D+V309I,
D59N+H76Q+L130I+L166V+L222I+N249D+G251D+S273Y,
Y21S+D59N+H76Q+I96L+S164G+L222I+N249D+G251D+S273Y,
K19T+D59N+S164G+L166V+L222I+S226T+G251D+S273Y,
D59N+H76Q+L130I+S132A+S164G+L222I+R242E+G251D+S273Y,
K19T+Y21S+H76Q+S164G+L222I+G251D+S273Y,
D59N+H76Q+S164G+L222I+R242E+S273Y+V309I,
K19T+Y21S+D59N+H76Q+S132A+S164G+L222I+G251D+S273Y,
K19T+D59N+H76Q+L130I+S164G+L222I+S226T+G251D+S273Y,
D59N+H76Q+S164G+L166V+L222I+N249D+G251D+S273Y+V309I,
K19T+Y21S+D59N+H76Q+L130I+S164G+L222I+S273Y,
Y21S+D59N+S164G+L222I+R242E+G251D+S273Y+V309I,
K19T+D59N+H76Q+L166V+L222I+R242E+G251D+S273Y,
D59N+S132A+S164G+L222I+R242E+N249D+G251D+S273Y,
D59N+H76Q+I96L+L130I+S164G+L222I+N249D+G251D+S273Y,
Y21S+D59N+H76Q+S164G+L166V+N249D+G251D+S273Y,
H76Q+S132A+S164G+L222I+N249D+G251D,
D59N+H76Q+S132A+S164G+L166V+S273Y,
K19T+D59N+H76Q+S132A+L222I+G251D+S273Y+V309I,
H76Q+L130I+L222I+S226T+G251D+S273Y,
Y21S+D59N+H76Q+I96L+L222I+S273Y,
Y11I+K19T+D59N+E83S+I96L+S164G+L222I+N249D,
Y11I+K19T+I96L+S164G+L222V+R242E+G251D,
Y11V+K19T+I96L+S164G+L166V+L222I+R242E,
Y11V+E83S+I96L+S164G+L222I+R242E+G251D+L253I+I263L,
Y11V+I96L+S164G+L222I+R242E+N249D+L253I+I263L,
K19S+I96L+S164G+L166V+L222I+R242E,
K19T+I96L+S164G+L166V+L222I+R242E+N249D+I263L,
Y11V+K19T+D59N+I96L+S164N+L166I+L222I+G251D,
H76Q+I96L+S164G+L222I+R242E+G251D+S273Y,
Y11V+K19T+E83S+I96L+S164G+L166V+L222I+R242E+G251D, Y11V+E83S+I96L+S164G+L222I+R242E+L253I+I263L,
Y11V+K19T+D59N+I96L+S164G+L166V+L222I+R242E+G251D+L253I,
K19T+D59N+I96V+S164G+L166V+L222I+R242E+I263L,
Y11V+D59N+I96L+S164G+L222I+G251D+L253V,
I96L+S164G+L166V+L222I+R242E+N249D+I263L,
K19S+D59N+I96L+S164G+L222I+R242E+N249E+G251D,
H76Q+I96L+S164G+L222I+R242E+G251D,
Y11I+K19T+D59N+S164G+L222I+G251D+I263V,
K19T+I96L+S164G+L166V+L222I+R242E+N249D+G251D+I263V,
K19T+E83S+I96L+S164G+L222I+R242E+G251D+L253I,
I96L+S164G+L222I+R242E+N249D+G251D+I263L,
K19T+D59N+I96L+S164G+L166V+L222I+R242D+G251D+L253I,
D59N+I96L+S164G+L222I+R242E+L253I+I263L,
K19T+I96L+S164G+L166V+L222I+N249D+I263L,
K19T+D59N+I96L+S164G+L166I+L222I+R242D+G251D+I263V,
K19T+D59N+I96L+S164G+L222V+R242E+N249D+L253I,
K19T+D59N+I96L+S164G+L166I+L222I+R242E+N249D,
K19T+E83S+I96L+S164G+L222I+R242E+N249D+G251D+L253I,
I96L+S164G+L222I+R242E+G251D+S273Y,
K19T+E83T+I96L+S164G+L222I+R242E+L253V,
K19T+I96L+S164G+R242E+L253I,
K19T+D59N+I96L+S164G+L222I+N249E+G251D+L253V+I263L,
K19T+D59N+I96L+S164G+L222V+N249E+G251D+I263V,
I96L+S164G+L222I+R242E+G251D,
K19T+I96L+S164N+L222I+R242E+I263L,
K19T+E83S+I96L+S164G+L166V+L222I+R242E+N249D+G251D+L253I,
K19T+D59N+E83T+S164G+L166V+L222I+R242D+G251D,
K19T+D59N+I96L+S164G+L222I+G251D,
D59N+I96L+L166V+L222I+R242E+G251D,
Y11I+K19T+D59N+I96V+L222I+R242D+G251D,
K19T+I96V+S164G+L222I+N249D+G251D+L253I,
H76Q+N100Q+N291Q,
R67Q+L130I+M157L+D158S+R242E+N291Q,
V32L+R67Q+L130I+M157L+K231N+M256L,
R67Q+V136I+M157L+L222I+V248I,
Y11V+R67Q+L130I+M157L+L222I+R242E,
R67Q+I96L+N100Q+L130I+M157L+N292H.
Y11I+D59N+I96L+S164G+L166V+L222V+R242E+G251D+L253I,
Y11I+D59N+I96L+S164G+L166V+L222V+R242E+G251D,
Y11I+D59N+I96L+S164G+L166V+L222V+R242E+N249E+G251D,
Y11V+K19T+D59N+I96L+S164G+L166V+L222V+R242E+N249E+G251D,
Y11I+I96L+S164G+L166V+L222V+R242E+N249E+G251D,
Y11V+K19T+I96L+L166V+L222V+R242E+G251D,
Y11V+K19T+D59N+I96L+S164G+L166I+L222V+R242E+N249E+G251D+L253I,
Y11I+K19T+D59N+I96L+S164G+L166V+L222V+R242E+N249E+G251D, Y11I+K19T+D59N+I96L+S164G+L166V+L222I+R242E+N249E+G251D,
Y11V+K19T+D59N+I96L+S164G+L166V+L222V+R242E+N249E+L253I,
Y11V+K19T+D59N+I96L+L166V+L222V+R242E+N249E+G251D+L253I,
Y11V+K19T+D59N+I96L+S164G+L166V+L222I+R242E+N249E,
Y11V+K19T+D59N+I96L+S164G+L166V+L222V+R242E+G251D,
Y11I+K19T+D59N+I96L+S164G+L166V+R242E+G251D,
Y11I+K19T+D59N+I96L+S164G+L166I+L222I+R242E+G251D,
Y11V+K19T+I96L+S164G+L166V+L222V+R242E+N249E+G251D,
Y11I+K19T+D59N+I96L+S164G+L166I+L222V+R242E+N249E+G251D,
Y11V+D59N+I96L+S164G+L166I+L222I+R242E+G251D,
Y11V+K19T+D59N+I96L+S164G+L166I+L222V+R242E+N249E+G251D,
Y11I+K19T+D59N+I96L+S164G+L222I+R242E,
Y11I+K19T+I96L+S164G+L166V+R242E+N249E+G251D,
Y11I+I96L+S164G+L222I+R242E,
Y11I+K19T+D59N+I96L+S164G+L222I+R242E+N249E+G251D,
Y11V+D59N+I96L+S164G+L166I+L222V+R242E+G251D+L253I,
Y11I+K19T+D59N+I96L+L222V+R242E+N249E+G251D,
Y11V+K19T+D59N+I96L+S164G+L166I+L222I+R242E+N249E+G251D,
Y11V+K19T+D59N+I96L+S164G+L222I+R242E+N249E+G251D,
Y11I+D59N+I96L+S164G+L222I+R242E+G251D,
Y11V+K19T+D59N+I96L+S164G+L166I+R242E+N249E+G251D+L253I,
Y11I+D59N+I96L+S164G+L222V+R242E+N249E+G251D,
Y11I+K19T+S164G+L166I+L222V+R242E+N249E+G251D,
Y11V+K19T+D59N+S164G+L166V+L222I+R242E+N249E+G251D,
Y11V+K19T+D59N+I96L+S164G+L166V+R242E,
Y11I+K19T+D59N+I96L+S164G+L222V+R242E+N249E,
Y11V+K19T+D59N+I96L+S164G+L222V+R242E+G251D,
Y11V+K19T+D59N+I96L+S164G+R242E+G251D,
Y11V+K19T+D59N+I96L+S164G+L166I+L222V+R242E+G251D,
Y11I+I96L+L222V+R242E+N249E+G251D,
Y11I+K19T+D59N+S164G+L166I+L222V+R242E+G251D,
Y11V+K19T+D59N+I96L+S164G+L222V+R242E+N249E+G251D,
Y11V+K19T+D59N+I96L+L222V+R242E+G251D,
Y11V+K19T+D59N+S164G+L166I+L222I+R242E+G251D,
Y11V+K19T+D59N+L166V+L222I+R242E+N249E+G251D+L253I,
Y11V+K19T+I96L+L222V+R242E+N249E+G251D or
Y11I+K19T+L222V+R242E+N249E+G251D.

Item 12. An isolated chymosin polypeptide variant comprising an alteration in one or more positions compared to a parent polypeptide having chymosin activity, wherein the alteration is comprising a substitution in at least one amino acid position corresponding to any of positions V32L, I45V, N50K, G70D, G70N, D98V, N100Q, V136I, M142I, H146R, S154A, V155F, M157L, D158S, V198I, I200V, F223V, K231N, G244D, V248I, R254S, M256L, V259I, E262T, D267Q, D279E, T284S, N291Q N292H, L295K, and/or K321P wherein (i): the amino acid position of the parent polypeptide is determined by an alignment of the parent polypeptide with the mature polypeptide of SEQ ID NO: 2 (camel chymosin) and (ii): the parent polypeptide has at least 65% sequence identity with the mature polypeptide of SEQ ID NO: 2 (camel chymosin);

wherein the isolated chymosin polypeptide variant cleaves αS1-casein with a higher frequency than the corresponding parent polypeptide.

Item 13. The isolated chymosin polypeptide variant of item 12, wherein the parent polypeptide has at least 80%, such as at least e.g. 80%, 85%, 95%, 97%, 98%, 99% sequence identity with the mature polypeptide of SEQ ID NO:2 (camel chymosin).

Item 14. An isolated chymosin polypeptide variant according to any of items 12 to 13, wherein the isolated chymosin polypeptide variant comprise an alteration in one or more of the combinations of positions comprising the positions corresponding to:
G70D+S74F+D158S+R254S+S277N,
L130I+M142I+I200V+V259I+E294Q,
Y21S+R61S+H146R,
R61S+G163E+M256L+S277N,
D59N+S271P+T284S,
V248I+S226T+E294Q,
S74F+G244D+S271P,
V221K+V248I+S255Y,
V183I+G251W+M256L,
R61Q+V136I+Y268F+T284S+Y307F,
N50K+D158S+V203A+E294Q,
D98V+G251D+M256L+V259I,
V183I+V248I+G244D+T284S,
N50K+R61S+Y127F+G244D+G251D,
I96L+F223V+G244D+R254S+M256L,
H146R+D158S+S273Y,
S74F+V259I+Y268F,
G70N+D98V+V136I,
I96L+M142I+R145Q+H146R,
V32L+G163E+T186S+Q188E+L295K,
R61Q+V136I+Y268F+T284S+Y307F,
S132A+Q188E+F223V,
I200V+G251D+G289S,
N50K+D158S+V203A+E294Q,
F223V+G251W+S273Y+D279E,
D59N+L222I+G251D+V32L+L12M+T284S,
D59N+L222I+G251D+V155F+E262T+V32L,
D59N+L222I+G251W+S154A+V203A,
D59N+L222I+G251D+V32L+K321P+V260T,
D59N+L222I+G251D+V198I+V203A+K321P,
D59N+L222I+G251D+S273Y+T284S+D267Q,
V32L+N100Q+N291Q,
N292H+N100Q+N291Q,
V221K+N100Q+N291Q,
I297A+N100Q+N291Q,
R67Q+N100Q+L130I+M142I+L222I+K231N,
R67Q+L130I+V248I+M256L+N292H,
V32L+R67Q+L130I+K231N+N292H,
L130I+M157L+V248I+M256L+N291Q,
V32L+R67Q+V136I+M157L+N291Q,
R67Q+L130I+K231N+V248I+N291Q, V32L+R67Q+G70D+N100Q+M157L,
R67Q+N100Q+L130I+D158S+V248I,
R67Q+N100Q+L130I+M157L+K231N+N291Q,
R67Q+N100Q+L130I+M157L+V248I+N291Q and/or
N100Q+L130I+S132A+M157L+K231.

Item 15. A method for making a food or feed product comprising adding an effective amount of the isolated chymosin polypeptide variant according to any of items 9 to 14 to the food or feed ingredient(s) and carrying our further manufacturing steps to obtain the food or feed product.

Item 16. A method according to claim 15, wherein the food or feed product is a milk-based product.

Item 17. Use of a chymosin polypeptide variant according to any of item 9 to 12 in a process for making cheese.

Item 18. Use of a chymosin polypeptide variant according to any of items 9 to 14 in a process for making Pasta filata, Cheddar, and Continental type cheeses.

Item 19. Use of a chymosin polypeptide variant according to any of items 9 to 14 in a process for making Soft Cheese or White Brine Cheese.

A further related aspect of present invention concerns a method for making a food or feed product comprising adding an effective amount of the isolated chymosin polypeptide variant as described herein to the food or feed ingredient(s) and carrying our further manufacturing steps to obtain the food or feed product, in particular wherein the food or feed product is a milk-based product.

Also the use of a chymosin polypeptide variant as described herein in a process for making cheese is comprised by present invention. More specifically, the use of a chymosin polypeptide variant having a lower αS1-casein cleavage frequency than its corresponding parent peptide in a process for making Pasta filata, Cheddar, and Continental type cheeses and/or the use of a chymosin polypeptide variant having a higher αS1-casein cleavage frequency than its corresponding parent peptide in a process for making Soft Cheese, White Brine and long ripening Gouda cheese.

Definitions

All definitions of herein relevant terms are in accordance of what would be understood by the skilled person in relation to the herein relevant technical context.

The term "αS1-cleavage" or "cleavage of αS1-casein" means any enzymatic cleavage of αS1-casein. Such as e.g. cleavage between Phe23 and Phe24, resulting in the formation of αS1(1-23) peptide.

In one aspect αS1-cleavage is determined by quantifying the αS1-cleavage peptide 1-23 obtained by incubating skim milk with the chymosin variant or the camel chymosin, wherein quantification is carried out by RP-HPLC coupled to an ESI-Q-TOF mass spectrometer. Full details of a preferred method of determining αS1-casein cleavage are described in the Examples.

The term "chymosin" relates to an enzyme of the EC 3.4.23.4 class. Chymosin has a high specificity and predominantly clots milk by cleavage of a single 104-Ser-Phe-|-MetAla-107 bond in κ-chain of casein. As a side-activity, chymosin also cleaves α-casein primarily between Phe23 and Phe24 (references 2,3). The resulting peptide αS1(1-23) will be further degraded by proteases from microbial cultures added to the ripening cheese (reference 4). An alternative name of chymosin used in the art is rennin.

The term "chymosin activity" relates to chymosin activity of a chymosin enzyme as understood by the skilled person in the present context.

The skilled person knows how to determine herein relevant chymosin activity.

The term "specific clotting activity" describes the milk clotting activity of a chymosin polypeptide and can be determined according to assays well known in the art. A preferred method for determining the specific clotting activity in terms of IMCU/mg of protein is the standard method developed by the International Dairy Federation (IDF method), which comprises steps, wherein milk clotting activity is determined from the time needed for a visible flocculation of a milk substrate and the clotting time of a sample is compared to that of a reference standard having known milk-clotting activity and the same enzyme composition by IDF Standard 110B as the sample. Samples and reference standards are measured under identical chemical and physical conditions. Full details of a the IDF method are described in the Examples.

As known in the art—the herein relevant so-called C/P value is determined by dividing the specific clotting activity (C) with the proteolytic activity (P).

As known in the art—a higher C/P value implies generally that the loss of protein during e.g. cheese manufacturing due to non-specific protein degradation is reduced, i.e. the yield of cheese is improved. Differences in C/P values may be defined in terms of percentages. As example, a C/P value of 20 will correspond to 50% of a C/P value of 40.

The term "isolated variant" means a variant that is modified by the act of man. In one aspect, the variant is at least 1% pure, e.g., at least 5% pure, at least 10% pure, at least 20% pure, at least 40% pure, at least 60% pure, at least 80% pure, and at least 90% pure, as determined by SDS PAGE.

The amino acid numbering as used herein to specify chymosin polypeptide variants of the present invention is done on the mature peptide numbering. In the sequence listing provided with the present application:

SEQ ID NO:1 represents the complete polypeptide sequence of bovine pre-prochmyosin;

SEQ ID NO:2 represents the complete polypeptide sequence of camel pre-prochmyosin;

SEQ ID NO:3 represents the polypeptide sequence of mature bovine chymosin;

SEQ ID NO:4 represents the polypeptide sequence of mature camel chymosin.

In other words, SEQ ID NOs:3 and 4 correspond to amino acids 59 to 381 of SEQ ID NOs:1 and 2, respectively. All of the specific substitutions identified herein are identified in relation to the position of the mature chymosin sequence, i.e. in relation to the amino acid numbering of SEQ ID NOs:3 or 4. Insofar as the position is identified in relation to the amino acid numbering of SEQ ID NOs:1 or 2 one has to add 58 residues to identify the position in SEQ ID NOs:1 or 2.

The term "mature polypeptide" means a peptide in its final form following translation and any post-translational modifications, such as N-terminal processing, C-terminal truncation, glycosylation, phosphorylation, etc. In the present context may a herein relevant mature chymosin polypeptide be seen as the active chymosin polypeptide sequence—i.e. without the pre-part and/or pro-part sequences. Herein relevant examples of a mature polypeptide are e.g. the mature polypeptide of SEQ ID NO: 1 (bovine chymosin), which is from amino acid position 59 to amino acid position 381 of SEQ ID NO: 1 or the mature polypeptide of SEQ ID NO: 2 (camel chymosin), which is from amino acid position 59 to amino acid position 381 of SEQ ID NO: 2.

The term "parent" or "parent polypeptide having chymosin activity" means a polypeptide to which an alteration is made to produce the enzyme variants of the present invention. The parent may be a naturally occurring (wild-type) polypeptide or a variant thereof.

The term "Sequence Identity" relates to the relatedness between two amino acid sequences or between two nucleotide sequences.

For purposes of the present invention, the degree of sequence identity between two amino acid sequences may be determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
  Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
  Alignment−Total Number of Gaps in Alignment).

The term "variant" means a peptide having chymosin activity comprising an alteration, i.e., a substitution, insertion, and/or deletion, at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

The amino acid may be natural or unnatural amino acids—for instance, substitution with e.g. a particularly D-isomers (or D-forms) of e.g. D-alanine could theoretically be possible.

The term "wild-type" peptide refers to a nucleotide sequence or peptide sequence as it occurs in nature, i.e. nucleotide sequence or peptide sequence which hasn't been subject to targeted mutations by the act of man.

DRAWINGS

FIG. 1:
3D structure of camel chymosin (PDB: 4AA9) with a model of bound αS1-casein shown in blue. αS1-casein is placed in the chymosin substrate binding cleft with the scissile bond between residues 23 and 24. Camel chymosin residues R266, V51, E83, I263, L253, L105, I96, and L180 are highlighted in green.

Figure 2:
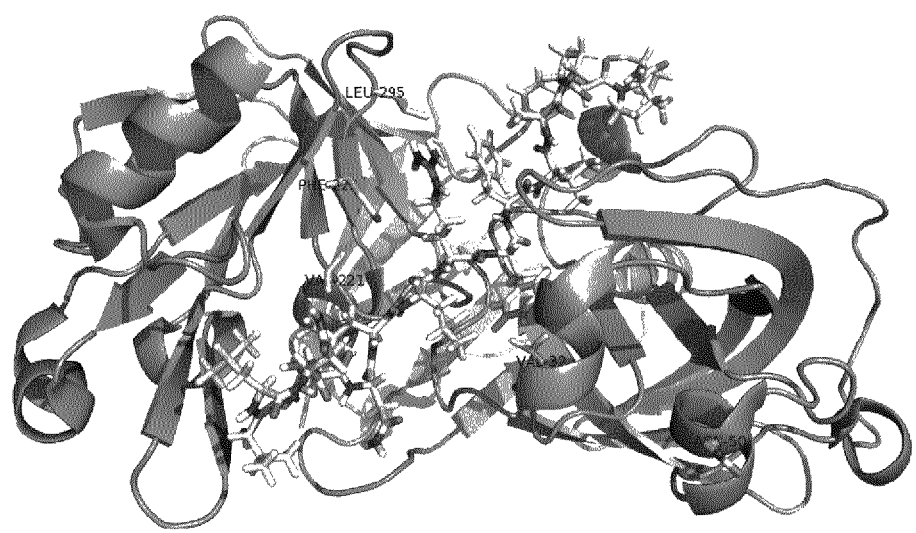

FIG. 2:
3D structure of camel chymosin (PDB: 4AA9) with a model of bound αS1-casein shown in blue. αS1-casein is placed in the chymosin substrate binding cleft with the scissile bond between residues 23 and 24. Camel chymosin residues V32, H76, F119, L130, S132, Y190, V221, R242, S273, G289, N292, L295, and I297 are highlighted in green.

Figure 3:
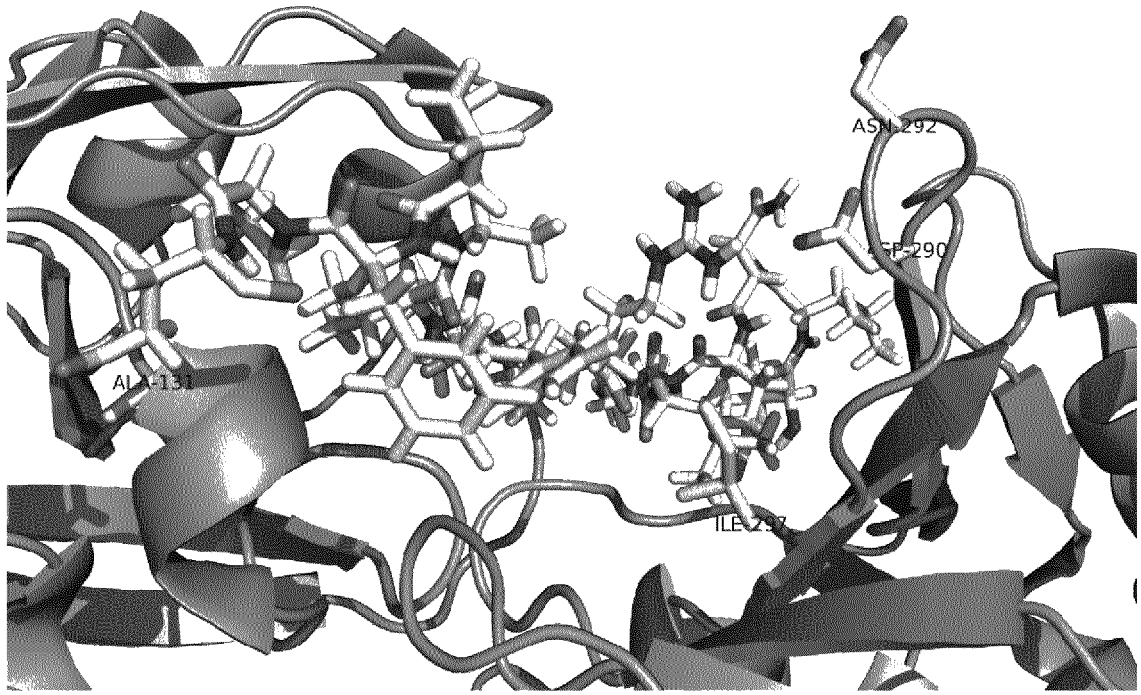

FIG. 3:
3D structure of camel chymosin (detail, PDB: 4AA9). Residues Y11, L12, and D13 of the protein N-terminus as well as the potential Y11 interaction partner D290 are highlighted in purple.

EXAMPLES

Example 1: Alignment and Numbering of Chymosin Protein Sequences and Variant Sequences Chymosin protein sequences were aligned using the ClustalW algorithm as provided by the EBI (EBI, tools, multiple sequence alignment, CLUSTALW", http://www.ebi.ac.uk/Tools/msa/clustalw2/) and as described in Larkin M A, Blackshields G, Brown N P, Chenna R, McGettigan P A, McWilliam H, Valentin F, Wallace I M, Wilm A, Lopez R, Thompson J D, Gibson T J, Higgins D G (2007). Bioinformatics 23(21), 2947-2948.

ClustalW2 settings for multiple sequence alignments were Protein weight Matrix=BLOSUM, GAP open=10, GAP EXTENSION=0.05, GAP DISTANCES=8, No End Gaps, ITERATION=none, NUMITER=1, CLUSTERING=NJ As a reference sequence the bovine chymosin B prepro-chymosin was used (Genbank accession number P00794—disclosed herein as SEQ ID NO: 1), where the N-terminal Methionin has number 1 (MRCL . . . ) and the C-terminal Isoleucin (in the protein sequence . . . LAKAI) has number 381.

Example 2: Design of Chymosin Variants

Chymosin variants were designed using different strategies.

When there is referred to camel chymosin there is referred to camel chymosin comprising the mature polypeptide of SEQ ID NO: 2 herein.

Camel chymosin of SEQ ID NO: 2 may be seen as a herein relevant parent polypeptide having chymosin activity used to make camel chymosin variants thereof.

When there is referred to bovine chymosin there is referred to bovine chymosin comprising the polypeptide of SEQ ID NO: 1 herein.

Bovine chymosin of SEQ ID NO: 1 may be seen as a relevant parent polypeptide having chymosin activity used to make bovine chymosin variants thereof.

Variants 1 to 269 and 367 to 461 of camel chymosin were designed based on an alignment of a large set of public known aspartic protease sequences having an identity of 25% or more compared to bovine chymosin B.

Variations were generally introduced in regions with a high level of amino acid variation between species, while conserved regions were not changed. Amino acid substitutions were chosen based on phylogenetic, structural and experimental information to identify changes with high probability to show beneficial effects on alpha casein cleavage. Multiple variations were introduced in each variant construct, ensuring that each single mutation was present in multiple variant constructs to minimize the effect of covariation between various substitutions. Machine learning and statistical analysis of experimental data were used to determine the relative contributions of the amino acid substitutions to measured coagulant performance of the chymosin variants (references 14, 15).

Variants 270 to 366 were designed based on detailed structural analysis of bovine chymosin (PDB code: 4AA8) and camel chymosin (PDB code: 4AA9). Variations were chosen based on the chemical nature of the respective amino acid side chains and their expected impact on either casein substrate binding or general enzyme properties. Most of the amino acid substitutions in variants 270 to 346 were made in sequence positions either within or in close structural proximity to the substrate binding cleft, or in secondary structural elements that get into contact with the bound casein substrate. Furthermore, changes were made in positions on the protein surface that alter the charge profile of these regions (reference 5) and are therefore expected to have an impact on enzyme performance. Variants 347 to 366 were made based on the different structural conformation of the N-terminal sequence in bovine and camel chymosin. Amino acid substitutions were made in positions within the substrate binding cleft that interact with the N-terminus in camel chymosin.

Example 3: Preparation of Chymosin Variant Enzyme Material

All chymosin variants were synthesized as synthetic genes and cloned into a fungal expression vector such as e.g. pGAMpR-C (described in WO02/36752A2)

The vectors were transformed into *E. coli* and plasmid DNA was purified using standard molecular biology protocols, known to the person skilled in the art.

The variant plasmids were individually transformed into an *Aspergillus niger* or Aspergillus *nidulans* strain and protein was produced essentially as described in WO02/36752A2 and purified using standard chromatography techniques.

As known in the art—the skilled person may, based on his common general knowledge, produce and purify chymosin and chymosin variants—such as herein described bovine and camel chymosin variants.

Example 4: Determination of Specific Chymosin Activity

4.1 Determination of Milk Clotting Activity

Milk clotting activity was determined using the REMCAT method, which is the standard method developed by the International Dairy Federation (IDF method) Milk clotting activity is determined from the time needed for a visible flocculation of a standard milk substrate prepared from a low-heat, low fat milk powder with a calcium chloride solution of 0.5 g per liter (pH≈6.5). The clotting time of a rennet sample is compared to that of a reference standard having known milk-clotting activity and having the same enzyme composition by IDF Standard 110B as the sample. Samples and reference standards were measured under identical chemical and physical conditions. Variant samples were adjusted to approximately 3 IMCU/ml using an 84 mM acetic acid buffer pH 5.5. Hereafter, 200 µl enzyme preparation was added to 10 ml preheated milk (32° C.) in a glass test tube placed in a water bath, capable of maintaining a constant temperature of 32° C.±1° C. under constant stirring. Alternatively, 20 µL enzyme preparation was added to 1 mL preheated milk as described above.

The total milk-clotting activity (strength) of a rennet was calculated in International Milk-Clotting Units (IMCU) per ml relative to a standard having the same enzyme composition as the sample according to the formula:

$$\text{Strength in IMCU}/ml = S\text{standard} \times T\text{standard} \times D\text{sample}/D\text{standard} \times T\text{sample}$$

Sstandard: The milk-clotting activity of the international reference standard for rennet.

Tstandard: Clotting time in seconds obtained for the standard dilution.

Dsample: Dilution factor for the sample

Dstandard: Dilution factor for the standard

Tsample: Clotting time in seconds obtained for the diluted rennet sample from addition of enzyme to time of flocculation For clotting activity determination of multi-substitution libraries 1, 3, 4 and 6, as well as variants 270 through 366, the pIMCU method was used instead of the REMCAT method. As compared to REMCAT, flocculation time of chymosin variants in the pIMCU assay was determined by OD measurements in 96-well microtiter plates at 800 nm in a UV/VIS plate reader. A standard curve of various dilutions of a reference standard with known clotting strength was recorded on each plate. Samples were prepared by diluting enzyme in 84 mM acetate buffer, 0.1% triton X-100, pH 5.5. Reaction at 32° C. was started by adding 250 uL of a standard milk substrate containing 4% (w/w) low-heat, low fat milk powder and 7.5% (w/w) calcium chloride (pH≈6.5) to 25 uL enzyme sample. Milk clotting activity of chymosin variants in International Milk-Clotting Units (IMCU) per ml was determined based on sample flocculation time relative to the standard curve.

4.2 Determination of Total Protein Content

Total protein content was determined using the Pierce BCA Protein Assay Kit from Thermo Scientific following the instructions of the providers.

4.3 Calculation of Specific Clotting Activity

Specific clotting activity (IMCU/mg total protein) was determined by dividing the clotting activity (IMCU/ml) by the total protein content (mg total protein per ml).

Example 5 Determination of αS1-Casein Cleavage

Determination of αS1-Casein Hydrolysis Activity

Chymosin mediated proteolysis of milk proteins was characterized by determining profiles of water soluble peptides extracted at pH 4.6. A culture free cheese model made in 96 well plates was used for the study. In brief, 750 µl skim milk from Øllngegård, Denmark added glucono-delta-lactone (GDL) and calcium chloride was aliquoted into the wells of a 96 deep well plate. After 10 min from addition of GDL to the milk, variants of chymosin were added to individual wells of the plate to a final activity of 0.05 IMCU/ml. The formed coagulum was cut after 30 min from addition of rennet by thoroughly stirring the coagulum with a pipette tip; a new tip was used for each well. Subsequently, the plate was left for another 60 min before curd and whey was separated by centrifugation of the plate for 10 min at 2500 g. The milk was kept at 30° C. during renneting, cutting and syneresis. Finally, whey was decanted from the plate and the pellet of rennet curd left in the plate was stored for 4 days at room temperature. Peptides were extracted by adding 500 µl of 0.5 M tri-sodium citrate to each well and gentle shaking the plate for 24 hours at 37° C. The now fully dissolved rennet curd was then precipitated by adding hydrochloric acid to a final pH of 4.4-4.5. The plate was spun down in a centrifuge and the supernatant recovered for further analysis of pH 4.5 soluble peptides.

Profiles of pH 4.5 soluble peptides were determined using RP-HPLC coupled to an ESI-Q-TOF mass spectrometer. The analysis was performed by using a liquid chromatography system (Agilent 1290 infinity, Agilent Technologies A/S, Santa Clara, Calif., USA) coupled to a mass spectrometer (G6540A Q-TOF, Agilent Technologies A/S, Santa Clara, Calif., USA). The column in the LC system was Ascentis Express Peptide ES-C18m, 2.7 µm, 100×2.1 mm (Supelco, Sigma-Aldrich, St. Louis, USA). The mobile phase consisted of eluent A (0.1% formic acid in water) and eluent B (Acetonitrile: 0.1% formic acid in water, 9:1). After equilibration of the column with 2% B, a sample volume of 10 µL was injected. The peptides were separated by gradient elution generated by increasing eluent B from 2% to 50% over 15 column volumes. The flow rate was 0.44 mL/min. Peptides were detected by continuously measuring the UV absorbance at 214 nm. By running MS scans from 100 to 2000 m/z the mass spectra were collected. MS/MS analysis was performed on the two most intense ions from each scan. A MIX sample consisting of equal volume of all samples analyzed was prepared and this sample was analyzed for each 12 samples. MS data were converted from the Agilent .d format to .mzml files using MSConvert ver. 3.0.6618. All further data analysis was done using R 3.1.3. Peptides were identified from MS/MS spectra using R package 'MSGFplus' version 1.05. Search database for peptide identification were limited to the bovine milk proteins: αs1-casein, αs1-casein, β-casein, κ-casein, β-lactoglobulin, α-lactalbumin, lactoperoixdase and lactoferrin. Serine phosphorylation and methionine oxidation were included as variable modifications. R package 'xcms' v. 1.42.0 was used for detecting and grouping peaks across samples in a sampleset according to Smith et al. (2006). Massifquant method was used for peak detection and grouping of peaks was based on the density method. Identity was assigned to grouped peaks resulting in quantitative tables of approximately 200 identified peptides including αS1-casein (1-23).

Statistical Analysis of the Positional and Mutational Effects on αS1-Casein Cleavage A statistical machine-learning approach and PCA-based analysis was used to determine the effects of all single mutations present in the variants of multi-substitution libraries 1-3, 4, 5, 6 and 7 on cleavage of αS1-casein between amino acids Phe23 and Phe24.

Results

Multi-Substitution Library 1

Variants of camel chymosin, each having multiple substitutions compared to wild type, were generated and analyzed as described above. All variants have an amino acid sequence identical to camel chymosin (SEQ ID NO:2), except for the variations mentioned in the table. Both bovine and camel chymosin were included as references.

Clotting activities were determined using the pIMCU method.

TABLE 1

Cleavage of αS1-casein between amino acids Phe23 and Phe24 (yielding the N-terminal peptide αS1N) by camel chymosin variants 1-95. Numbers are given in % cleavage of wild type camel chymosin (CHY-MAX M).

| variant | mutations | | | | | αS1N |
|---|---|---|---|---|---|---|
| CHY-MAX | | | | | | 138 |
| CHY-MAX M | | | | | | 100 |
| 1 | I96L | G163E | V221M | | | 88 |
| 2 | Y127F | R145Q | Q188E | | | 97 |
| 3 | Y21S | L166V | L253I | | | 89 |
| 4 | N50K | T186S | Y307F | | | 113 |
| 5 | G70N | S277N | R316L | | | 104 |
| 6 | I200V | Y268F | S271P | R316L | | 113 |
| 7 | M157L | T186S | I200V | S273Y | | 146 |
| 8 | D98V | G251D | M256L | V259I | | 125 |
| 9 | R67Q | H76Q | S132A | V248I | S271P | 119 |
| 10 | Y21S | D98V | V221K | T239S | R316L | 146 |
| 11 | V136I | T186S | V221K | I263L | S277N | 139 |
| 12 | N50K | L222I | S255Y | | | 135 |
| 14 | R67Q | V221M | M256L | | | 117 |
| 15 | G70D | L166V | V317L | | | 171 |
| 16 | R67Q | L130I | M157L | | | 140 |
| 17 | Y21S | R61S | H146R | | | 121 |
| 18 | V136I | V221M | L222I | S226T | | 101 |
| 19 | S132A | R254S | V259I | Y307F | | 107 |
| 20 | Y21S | H76Q | Y307F | V317L | | 78 |
| 21 | D158S | L166V | V248I | F223V | G251D | 132 |
| 22 | G70D | S74F | D158S | R254S | S277N | 120 |
| 23 | N50K | D59N | M157L | M256L | G289S | 152 |
| 24 | M142I | V221K | T284S | | | 153 |
| 25 | R61S | R67Q | K231N | | | 114 |
| 26 | V32L | I96L | S277N | | | 133 |
| 27 | V183I | G251W | M256L | | | 124 |
| 28 | M157L | T239S | D279E | | | 132 |
| 29 | V248I | S226T | E294Q | | | 122 |
| 30 | S74F | L166V | T186S | V203A | | 89 |
| 31 | D98V | G251D | M256L | S277N | | 120 |
| 32 | R67Q | Y127F | V221K | G251W | | 130 |
| 33 | L130I | M142I | I200V | V259I | E294Q | 120 |
| 34 | G70D | I96L | I200V | D267M | D279E | 108 |
| 35 | G70N | K231N | S273Y | T284S | G289S | 133 |
| 36 | V32L | G70N | M142I | | | 164 |
| 37 | V203A | S273Y | L295K | | | 103 |
| 38 | S74F | G244D | S271P | | | 122 |
| 39 | L130I | G163E | Y307F | | | 112 |
| 40 | R61S | L166V | T239S | | | 79 |
| 41 | R254S | D279E | L295K | | | 159 |
| 42 | L130I | T239S | S277N | L295K | | 128 |
| 43 | G70D | V183I | Q188E | G289S | | 106 |
| 44 | R61S | G163E | M256L | S277N | | 121 |
| 46 | D98V | H146R | V203A | I263L | S271P | 96 |
| 47 | S132A | V221M | S255Y | S273Y | V317L | 81 |
| 48 | H76Q | L222I | G251W | | | 94 |
| 49 | V221K | V248I | S255Y | | | 122 |
| 50 | H76Q | K231N | G244D | | | 110 |
| 51 | Y127F | S132A | D158S | | | 104 |
| 52 | D59N | S271P | T284S | | | 121 |
| 53 | G70D | T186S | L253I | | | 94 |
| 54 | R61Q | V221K | K231N | D267M | | 134 |
| 55 | V221M | V248I | L253I | L295K | | 115 |
| 56 | V183I | V248I | G244D | T284S | | 126 |
| 57 | D59N | Y127F | L166V | V183I | S255Y | 82 |
| 58 | N50K | R61S | Y127F | G244D | G251D | 147 |
| 59 | I96L | F223V | G244D | R254S | M256L | 153 |
| 60 | V32L | R61Q | H146R | | | 119 |
| 61 | H146R | D158S | S273Y | | | 148 |
| 62 | R61Q | M142I | G289S | | | 105 |
| 63 | S74F | V259I | Y268F | | | 146 |
| 64 | G70N | D98V | V136I | | | 143 |
| 65 | D59N | V203A | R254S | | | 106 |
| 66 | T239S | I263L | D267M | T284S | | 100 |
| 67 | I96L | M142I | R145Q | H146R | | 130 |
| 68 | V32L | E294Q | R316L | V317L | | 78 |
| 69 | V32L | G163E | T186S | Q188E | L295K | 131 |
| 70 | R61Q | V136I | Y268F | T284S | Y307F | 124 |
| 71 | S132A | Q188E | F223V | | | 126 |
| 72 | H76Q | I96L | D158S | | | 82 |
| 73 | V136I | R145Q | G251D | | | 98 |
| 74 | R61Q | D98V | V317L | | | 98 |
| 75 | Y21S | D59N | I263L | | | 88 |
| 76 | I200V | G251D | G289S | | | 128 |
| 77 | D98V | M157L | V183I | | | 102 |

TABLE 1-continued

Cleavage of αS1-casein between amino acids Phe23 and Phe24 (yielding the N-terminal peptide αS1N) by camel chymosin variants 1-95. Numbers are given in % cleavage of wild type camel chymosin (CHY-MAX M).

| variant | mutations | | | | | αS1N |
|---|---|---|---|---|---|---|
| 78 | S226T | G244D | I263L | G289S | | 72 |
| 79 | Q188E | G251D | S271P | D279E | | 97 |
| 80 | N50K | D158S | V203A | E294Q | | 124 |
| 81 | V203A | V248I | G251W | L253I | Y268F | 64 |
| 82 | R61S | V183I | L222I | L253I | D267M | 89 |
| 84 | G70D | L130I | Y268F | | | 87 |
| 85 | Y127F | D267M | E294Q | | | 84 |
| 88 | F223V | V248I | I263L | | | 107 |
| 89 | G70N | R254S | S255Y | Y268F | | 93 |
| 90 | D59N | V248I | L222I | V248I | | 98 |
| 91 | F223V | G251W | S273Y | D279E | | 128 |
| 92 | R67Q | G70N | H146R | Q188E | S226T | 100 |
| 93 | S74F | H76Q | M142I | M157L | G163E | 104 |
| 94 | R61Q | S226T | T239S | V248I | G251W | 93 |
| 95 | V32L | L130I | R145Q | L222I | D279E | 119 |

In Table 1 are shown camel chymosin variants with data on cleavage of αS1-casein between Phe23 and Phe24. Since all enzyme variants were used at a normalized concentration of 0.05 IMCU/mL in the experiments, decreased αS1-casein cleavage indicates increased specificity of the respective variant for cleavage of κ-casein between Phe105 and Met106 over cleavage of αS1-casein between Phe23 and Phe24, rather than decreased general enzymatic activity. Vice versa, increased αS1-casein cleavage indicates decreased specificity of the respective variant for cleavage of κ-casein between Phe105 and Met106 over cleavage of αS1-casein between Phe23 and Phe24, rather than increased general enzymatic activity.

Multi-Substitution Library 2

Another set of camel chymosin variants, each having multiple substitutions compared to wild type, were generated and analyzed as described. All variants have an amino acid sequence identical to camel chymosin, except for the variations mentioned in the table. Both bovine and camel chymosin were included as references. Clotting activities were determined using the REMCAT method.

TABLE 2

Cleavage of αS1-casein between amino acids Phe23 and Phe24 (yielding the N-terminal peptide αS1N) by camel chymosin variants 96-143. Numbers are given in % cleavage of wild type camel chymosin (CHY-MAX M).

| variant | mutations | | | | | αS1N |
|---|---|---|---|---|---|---|
| CHY-MAX | | | | | | 161 |
| CHY-MAX M | | | | | | 100 |
| 96 | D59N | L222I | G251D | E83S | Q162S | 76 |
| 97 | D59N | L222I | G251W | F17Y | Y21S | 116 |
| 98 | D59N | L222I | G251D | H76Q | S164G | 81 |
| 99 | D59N | L222I | G251D | K62Q | M165E | 102 |
| 100 | D59N | L222I | G251D | Q162S | V155F | 106 |
| 101 | D59N | L222I | G251D | H76Q | V155F | 112 |
| 102 | D59N | L222I | G251D | S273Y | L166V | 81 |
| 103 | D59N | L222I | G251D | Y268F | V198I | 113 |
| 104 | D59N | L222I | G251D | S273Y | F66Y | 109 |
| 105 | D59N | L222I | G251D | M165E | L166V | 101 |
| 106 | D59N | L222I | G251D | H76Q | M165E | 118 |
| 107 | D59N | L222I | G251D | F17Y | S273Y | 106 |
| 108 | D59N | L222I | G251D | L166V | I45V | 85 |
| 109 | D59N | L222I | G251W | L180I | T284S | 114 |
| 110 | D59N | L222I | G251D | V32L | L12M | T284S | 162 |
| 111 | D59N | L222I | G251D | Y21S | L166V | 86 |
| 112 | D59N | L222I | G251D | V155F | E262T | V32L | 144 |
| 113 | D59N | L222I | G251D | L105E | S164G | 80 |
| 114 | D59N | L222I | G251W | S154A | V203A | 123 |
| 115 | D59N | L222I | G251D | Q162S | L166V | 92 |
| 116 | D59N | L222I | G251W | K19T | R266I | 107 |
| 117 | D59N | L222I | G251W | I303L | I45V | 110 |
| 119 | D59N | L222I | G251D | Y21S | L215V | L105E | 79 |
| 120 | D59N | L222I | G251D | I96L | T177S | K321P | 90 |
| 121 | D59N | L222I | G251D | F17Y | T284S | V203A | 116 |
| 122 | D59N | L222I | G251D | V32L | K321P | V260T | 125 |
| 123 | D59N | L222I | G251D | V198I | V32L | E83S | 117 |
| 124 | D59N | L222I | G251D | I96L | V203A | V309I | 81 |
| 125 | D59N | L222I | G251D | Y268F | L215V | V32L | 119 |
| 126 | D59N | L222I | G251D | H76Q | L105E | V260T | 60 |
| 127 | D59N | L222I | G251D | Y21S | H76Q | Y268F | 97 |
| 128 | D59N | L222I | G251D | Y21S | I45V | F223A | 111 |
| 129 | D59N | L222I | G251D | V198I | V203A | K321P | 122 |
| 130 | D59N | L222I | G251D | S164G | R266V | I96L | 80 |
| 131 | D59N | L222I | G251D | H181N | F66Y | V32L | 114 |
| 132 | D59N | L222I | G251D | H181N | R266I | D267Q | 97 |
| 133 | D59N | L222I | G251W | K62Q | V309I | | 99 |
| 134 | D59N | L222I | G251D | Y268F | L12M | D267Q | 116 |
| 135 | D59N | L222I | G251D | L166V | E262T | T177S | 90 |
| 136 | D59N | L222I | G251D | S273Y | T284S | D267Q | 122 |
| 137 | D59N | L222I | G251D | F66Y | Q288E | I96L | 85 |
| 138 | D59N | L222I | G251D | V203A | R266V | F223A | 63 |
| 139 | D59N | L222I | G251D | I303L | S154A | V260T | 96 |
| 140 | D59N | L222I | G251D | Y21S | T284S | I96L | 82 |
| 141 | D59N | L222I | G251D | Y21S | T284S | I96L | 82 |

TABLE 2-continued

Cleavage of αS1-casein between amino acids Phe23 and Phe24 (yielding the N-terminal peptide αS1N) by camel chymosin variants 96-143. Numbers are given in % cleavage of wild type camel chymosin (CHY-MAX M).

| variant | mutations | | | | | | αS1N |
|---|---|---|---|---|---|---|---|
| 142 | D59N | L222I | G251D | Q288E | K19T | T177S | 91 |
| 143 | D59N | L222I | G251D | K62Q | Y268F | K19T | 96 |

In Table 2 are shown camel chymosin variants with data on cleavage of αS1-casein between Phe23 and Phe24. Since all enzyme variants were used at a normalized concentration of 0.05 IMCU/mL in the experiments, decreased αS1-casein cleavage indicates increased specificity of the respective variant for cleavage of κ-casein between Phe105 and Met106 over cleavage of αS1-casein between Phe23 and Phe24, rather than decreased general enzymatic activity. Vice versa, increased αS1-casein cleavage indicates decreased specificity of the respective variant for cleavage of κ-casein between Phe105 and Met106 over cleavage of αS1-casein between Phe23 and Phe24, rather than increased general enzymatic activity.

Multi-Substitution Library 3

A third set of camel chymosin variants, each having multiple substitutions compared to wild type, were generated and analyzed as described. All variants have an amino acid sequence identical to camel chymosin, except for the variations mentioned in the table. Both bovine and camel chymosin were included as references. Clotting activities were determined using the pIMCU method.

In Table 3 are shown camel chymosin variants with data on cleavage of αS1-casein between Phe23 and Phe24. Since all enzyme variants were used at a normalized concentration of 0.05 IMCU/mL in the experiments, decreased αS1-casein cleavage indicates increased specificity of the respective variant for cleavage of κ-casein between Phe105 and Met106 over cleavage of αS1-casein between Phe23 and Phe24, rather than decreased general enzymatic activity. Vice versa, increased αS1-casein cleavage indicates decreased specificity of the respective variant for cleavage of κ-casein between Phe105 and Met106 over cleavage of αS1-casein between Phe23 and Phe24, rather than increased general enzymatic activity.

Mutational Analysis of Multi-Substitution Libraries 1-3

A statistical analysis of the positional and mutational effects on αS1-casein cleavage αS1-casein cleavage was performed based on the proteolytic data of libraries 1-3. The most beneficial mutations for reduced αS1-casein cleavage are shown in table 4.

TABLE 3

Cleavage of αS1-casein between amino acids Phe23 and Phe24 (yielding the N-terminal peptide αS1N) by camel chymosin variants 144-179. Numbers are given in % cleavage of wild type camel chymosin (CHY-MAX M).

| variant | mutations | | | | | | | | | αS1N |
|---|---|---|---|---|---|---|---|---|---|---|
| CHY-MAX | | | | | | | | | | 161 |
| CHY-MAX M | | | | | | | | | | 100 |
| 144 | L12M | Y21S | D59N | H76Q | M165E | V198I | L222I | G251D | Q288E | 83 |
| 146 | L12M | Y21S | D59N | H76Q | M165E | L222I | G251W | S273Y | | 80 |
| 147 | L12M | D59N | H76Q | M165E | V198I | L222I | G251D | S273Y | K321P | 84 |
| 148 | L12M | D59N | H76Q | S154A | M165E | V203A | L222I | G251D | V309I | 79 |
| 149 | L12M | D59N | H76Q | D98V | L222I | | | | | 86 |
| 150 | L12M | K19T | V32L | D59N | H76Q | D144Q | M165E | L222I | G251D | 90 |
| 151 | L12M | Y21S | D59N | H76Q | M165E | V203A | L222I | G251D | E262T | 84 |
| 152 | L12M | V51L | H76Q | M165E | G251D | | | | | 68 |
| 153 | L12M | D59N | F66Y | H76Q | M165E | L180I | L222I | G251D | V309I | 84 |
| 154 | L12M | D59N | H76Q | S154A | M165E | L222I | G251W | Q288E | | 88 |
| 155 | L12M | D59N | H76Q | D98V | M165E | L222I | G251D | E262T | Q288E | 81 |
| 156 | L12M | V51L | D59N | H76Q | L166V | L222I | G251D | | | 58 |
| 157 | L12M | D59N | H76Q | D144Q | M165E | V203A | L222I | | | 79 |
| 158 | L12M | D59N | D144Q | M165E | L166V | L222I | G251D | | | 86 |
| 159 | L12M | K19T | D59N | H76Q | S154A | M165E | V198I | L222I | G251D | 71 |
| 160 | L12M | H76Q | D98V | M165E | L222I | G251W | | | | 94 |
| 161 | L12M | V32L | D59N | H76Q | M165E | L180I | V198I | L222I | G251D | 113 |
| 162 | L12M | D59N | H76Q | S154A | M165E | S273Y | | | | 80 |
| 164 | L12M | V51L | D59N | F66Y | H76Q | M165E | V203A | L222I | G251W | 65 |
| 165 | L12M | V32L | H76Q | M165E | L222I | E262T | | | | 106 |
| 166 | L12M | N50D | D59N | H76Q | M165E | G251W | E262T | | | 91 |
| 168 | V51L | D59N | H76Q | M165E | L180I | L222I | G251D | E262T | | 68 |
| 169 | L12M | D59N | H76Q | M165E | G251D | Q288E | V309I | K321P | | 59 |
| 172 | L12M | N50D | D59N | V203A | L222I | G251D | | | | 96 |
| 173 | L12M | D59N | H76Q | L180I | L222I | G251W | K321P | | | 88 |
| 174 | L12M | Y21S | D59N | M165E | L222I | K321P | | | | 99 |
| 176 | D59N | H76Q | M165E | L166V | V198I | L222I | | | | 95 |
| 178 | L12M | K19T | N50D | D59N | H76Q | M165E | L222I | Q288E | | 98 |
| 179 | L12M | Y21S | N50D | D59N | F66Y | H76Q | D144Q | M165E | L222I | G251D | 97 |

TABLE 4

Mutational contributions (mean) to reduced αS1-casein cleavage and standard deviations (sd) based on statistical analysis.

| mutation | mean | sd |
|---|---|---|
| R266V | 1.78E−01 | 5.51E−02 |
| V51L | 1.60E−01 | 2.97E−02 |
| E83S | 1.46E−01 | 4.67E−02 |
| I263L | 1.33E−01 | 2.76E−02 |
| L253I | 1.24E−01 | 3.64E−02 |
| L105E | 1.23E−01 | 3.15E−02 |
| I96L | 1.12E−01 | 3.58E−02 |
| L180I | 1.00E−01 | 5.44E−02 |
| H76Q | 8.19E−02 | 1.81E−02 |
| V309I | 7.79E−02 | 3.92E−02 |
| S226T | 7.74E−02 | 3.48E−02 |
| S273Y | 7.48E−02 | 2.77E−02 |
| E294Q | 7.13E−02 | 3.93E−02 |
| R316L | 6.77E−02 | 4.10E−02 |
| S255Y | 5.91E−02 | 2.50E−02 |
| V203A | 5.09E−02 | 2.13E−02 |
| Y307F | 4.99E−02 | 2.20E−02 |
| Q188E | 4.97E−02 | 2.05E−02 |
| V260T | 4.91E−02 | 2.97E−02 |

Based on the obtained results it is concluded that mutations shown in table 4 reveal an inhibiting effect on the cleavage of αS1-casein between Phe23 and Phe24. Since the mutations shown in table 4 cause less generation of αS1(1-23), they represent preferred mutations in chymosin variants for cheese manufacturing processes that require less softening of the cheese curd during ripening. Industrially relevant examples include Pasta filata, Cheddar, and Continental type cheeses with improved curd firmness for optimized slicing and shredding processes.

The 8 mutations with the strongest inhibiting effect on αS1-casein cleavage between Phe23 and Phe24 (R266V, V51L, E83S, I263L, L253I, L105E, I96L, L180I) are located distant from the substrate binding cleft of camel chymosin (FIG. 1). An indirect influence of these mutations on αS1-casein cleavage can therefore be concluded.

The most beneficial mutations for increased αS1-casein cleavage are shown in table 5.

TABLE 5

Mutational contributions (mean) to increased αS1-casein cleavage and standard deviations (sd) based on statistical analysis.

| mutation | mean | sd |
|---|---|---|
| V221K | 1.38E−01 | 2.30E−02 |
| N50K | 1.29E−01 | 2.90E−02 |
| F223V | 1.16E−01 | 2.51E−02 |
| V32L | 1.05E−01 | 2.07E−02 |
| L295K | 9.47E−02 | 2.40E−02 |
| I200V | 9.28E−02 | 2.70E−02 |
| T284S | 8.48E−02 | 2.27E−02 |
| M256L | 8.30E−02 | 1.86E−02 |
| H146R | 7.32E−02 | 3.11E−02 |
| V155F | 7.27E−02 | 2.96E−02 |
| V198I | 7.24E−02 | 2.46E−02 |
| M157L | 7.08E−02 | 2.38E−02 |
| F17Y | 6.58E−02 | 1.80E−02 |
| D158S | 6.04E−02 | 2.95E−02 |
| M142I | 5.86E−02 | 2.60E−02 |
| V136I | 5.83E−02 | 2.44E−02 |
| D267Q | 5.74E−02 | 2.36E−02 |
| F66Y | 4.89E−02 | 2.95E−02 |
| N50D | 4.72E−02 | 1.84E−02 |
| K231N | 4.71E−02 | 1.81E−02 |
| V259I | 4.71E−02 | 2.88E−02 |
| G244D | 4.52E−02 | 3.03E−02 |

Based on the obtained results it is concluded that mutations shown in table 5 cause higher cleavage of αS1-casein between Phe23 and Phe24. Since the mutations shown in table 5 cause higher generation of αS1(1-23), they represent preferred mutations in chymosin variants for cheese manufacturing processes that require more softening of the cheese curd during ripening. Industrially relevant examples include Soft Cheese and White Brine cheese.

Four out of the five mutations with highest impact on increased αS1-casein cleavage between Phe23 and Phe24 are located in the binding cleft of camel chymosin (V221K, F223V, V32L, L295K; FIG. 2) and might thus have a direct influence on αS1-casein binding during cheese ripening. Three of these mutations (V221K, F223V, V32L) introduce the amino acids of bovine chymosin (CHY-MAX) in the respective positions, which shows increased cleavage of αS1-casein between Phe23 and Phe24 compared to camel chymosin (CHY-MAX M; Tabs 1-3).

Multi-Substitution Library 4

Another set of camel chymosin variants, each having multiple substitutions compared to wild type, were generated and analyzed as described above. All variants have an amino acid sequence identical to camel chymosin (SEQ ID NO:2), except for the variations mentioned in the table. Camel chymosin (CHY-MAX M) is included as reference.

Clotting activities were determined using the pIMCU method.

TABLE 6

Cleavage of αS1-casein between amino acids Phe23 and Phe24 (yielding the N-terminal peptide αS1N) by camel chymosin variants 179-222. Numbers are given in % cleavage of wild type camel chymosin (CHY-MAX M).

| variant | mutations | | | | | | | | αS1N |
|---|---|---|---|---|---|---|---|---|---|
| CHY-MAX M | | | | | | | | | 100 |
| 180 | H76Q | S132A | S164G | L222I | N249D | G251D | | | 74 |
| 181 | Y21S | D59N | H76Q | S164G | L166V | N249D | G251D | S273Y | 73 |
| 182 | D59N | H76Q | S164G | L222I | R242E | S273Y | V309I | | 67 |
| 183 | D59N | H76Q | L130I | L166V | L222I | N249D | G251D | S273Y | 63 |
| 184 | Y21S | D59N | S164G | L222I | R242E | G251D | S273Y | V309I | 70 |
| 185 | K19T | Y21S | D59N | H76Q | S132A | S164G | L222I | G251D | S273Y | 67 |
| 186 | D59N | H76Q | I96L | L130I | S164G | L222I | R242E | G251D | 35 |
| 187 | H76Q | S164G | L166V | L222I | S226T | S273Y | | | 57 |
| 188 | K19T | D59N | I96L | S164G | L222I | G251D | | | 60 |

TABLE 6-continued

Cleavage of αS1-casein between amino acids Phe23 and Phe24 (yielding the N-terminal peptide αS1N) by camel chymosin variants 179-222. Numbers are given in % cleavage of wild type camel chymosin (CHY-MAX M).

| variant | mutations | | | | | | | | αS1N |
|---|---|---|---|---|---|---|---|---|---|
| 189 | Y21S | H76Q | S164G | L222I | R242E | G251D | S273Y | | 49 |
| 190 | H76Q | I96L | S164G | L222I | R242E | G251D | S273Y | | 36 |
| 191 | H76Q | S164G | L222I | N249D | G251D | S273Y | V309I | | 53 |
| 192 | K19T | D59N | H76Q | S164G | L222I | N249D | S273Y | | 51 |
| 193 | Y21S | D59N | H76Q | S164G | L222I | S226T | G251D | S273Y | 54 |
| 194 | H76Q | S164G | L166V | L222I | R242E | G251D | S273Y | | 44 |
| 195 | D59N | H76Q | I96L | S164G | L222I | S226T | N249D | G251D | S273Y 55 |
| 196 | D59N | H76Q | L130I | S164G | L166V | L222I | G251D | S273Y | V309I 57 |
| 197 | D59N | S132A | S164G | L222I | R242E | N249D | G251D | S273Y | 72 |
| 198 | H76Q | I96L | S164G | G251D | S273Y | V309I | | | 53 |
| 199 | D59N | H76Q | L130I | S164G | G251D | V309I | | | 61 |
| 200 | K19T | D59N | S164G | L166V | L222I | S226T | G251D | S273Y | 65 |
| 201 | D59N | H76Q | I96L | S132A | S164G | L222I | S226T | G251D | S273Y 50 |
| 202 | K19T | D59N | H76Q | I96L | S164G | L166V | L222I | G251D | S273Y 39 |
| 203 | K19T | D59N | H76Q | L130I | S164G | L222I | S226T | G251D | S273Y 68 |
| 204 | K19T | D59N | H76Q | S132A | L222I | G251D | S273Y | V309I | 78 |
| 205 | H76Q | L130I | L222I | S226T | G251D | S273Y | | | 78 |
| 206 | K19T | Y21S | D59N | H76Q | L130I | S164G | L222I | S273Y | 69 |
| 207 | Y21S | D59N | H76Q | I96L | S164G | L222I | N249D | G251D | S273Y 63 |
| 208 | K19T | D59N | H76Q | S164G | R242E | N249D | G251D | S273Y | 53 |
| 209 | D59N | H76Q | S164G | L222I | S226T | R242E | | | 58 |
| 210 | D59N | H76Q | I96L | S132A | S164G | L166V | L222I | G251D | S273Y 50 |
| 211 | D59N | H76Q | S132A | S164G | L166V | S273Y | | | 75 |
| 212 | Y21S | D59N | S164G | L222I | S226T | N249D | G251D | S273Y | 84 |
| 213 | D59N | H76Q | L130I | S132A | S164G | L222I | R242E | G251D | S273Y 65 |
| 214 | D59N | H76Q | S164G | L166V | L222I | N249D | G251D | S273Y | V309I 68 |
| 215 | D59N | H76Q | I96L | S164G | L222I | S226T | G251D | S273Y | V309I 60 |
| 216 | K19T | D59N | H76Q | L166V | L222I | R242E | G251D | S273Y | 70 |
| 217 | Y21S | D59N | H76Q | I96L | L222I | S273Y | | | 78 |
| 218 | D59N | H76Q | I96L | L130I | S164G | L222I | N249D | G251D | S273Y 72 |
| 219 | L130I | S164G | L222I | S273Y | | | | | 82 |
| 220 | K19T | Y21S | H76Q | S164G | L222I | G251D | S273Y | | 66 |
| 221 | Y21S | D59N | H76Q | L130I | S132A | S164G | L222I | G251D | S273Y 80 |
| 222 | D59N | H76Q | S226T | R242E | G251D | S273Y | | | 89 |

In table 6 are shown camel chymosin variants with data on cleavage of αS1-casein between Phe23 and Phe24. All variants reveal between 11% and 65% reduced proteolytic activity compared to wild type camel chymosin.

Mutational Analysis of Multi-Substitution Library 4

A statistical analysis of the positional and mutational effects on αS1-casein cleavage was performed based on the proteolytic data of library 4 variants. The most beneficial mutations for increased or decreased αS1-casein cleavage are shown in table 7.

TABLE 7

Mutational contributions (mean) to altered αS1-casein cleavage and standard deviations (sd) based on statistical analysis. Positive mean values represent decreased αS1-casein cleavage. Negative mean values represent increased αS1-casein cleavage.

| mutation | mean | sd |
|---|---|---|
| S164G | 5.65E−01 | 5.10E−02 |
| H76Q | 4.33E−01 | 2.63E−02 |
| I96L | 4.21E−01 | 4.03E−02 |
| R242E | 3.50E−01 | 3.99E−02 |
| L166V | 2.32E−01 | 3.82E−02 |
| L222I | 2.00E−01 | 4.90E−02 |
| K19T | 1.94E−01 | 2.99E−02 |
| Y21S | −1.13E−01 | 2.99E−02 |
| D59N | −1.34E−01 | 3.41E−02 |
| S132A | −1.75E−01 | 3.18E−02 |

Based on the results shown in table 7 it is concluded that mutations K19T, H76Q, I96L, S164G, L166V, L222I, and R242E lead to decreased cleavage of αS1-casein between Phe23 and Phe24. Since these mutations cause less generation of αS1(1-23), they represent preferred mutations in chymosin variants for cheese manufacturing processes that require less softening of the cheese curd during ripening. Mutations Y21S, D59N, and S132A lead to increased cleavage of αS1-casein between Phe23 and Phe24. Since these mutations cause higher generation of αS1(1-23), they represent preferred mutations in chymosin variants for cheese manufacturing processes that require more softening of the cheese curd during ripening.

Multi-Substitution Library 5

Another set of camel chymosin variants, each having multiple substitutions compared to wild type, were generated and analyzed as described above. All variants have an amino acid sequence identical to camel chymosin (SEQ ID NO:2), except for the variations mentioned in the table. Camel chymosin (CHY-MAX M) is included as reference.

Clotting activities were determined using the REMCAT method.

In table 8 are shown camel chymosin variants with data on cleavage of αS1-casein between Phe23 and Phe24. Out of 47 library variants, 44 reveal between 11% and 60% reduced proteolytic activity compared to wild type camel chymosin.

Mutational Analysis of Multi-Substitution Library 5

A statistical analysis of the positional and mutational effects on αS1-casein cleavage was performed based on the proteolytic data of library 5 variants. The most beneficial mutations for increased or decreased αS1-casein cleavage are shown in table 9.

TABLE 8

Cleavage of αS1-casein between amino acids Phe23 and Phe24 (yielding the N-terminal peptide αS1N) by camel chymosin variants 223-269. Numbers are given in % cleavage of wild type camel chymosin (CHY-MAX M).

| variant | mutations | | | | | | | | | αS1N |
|---|---|---|---|---|---|---|---|---|---|---|
| CHY-MAX M | | | | | | | | | | 100 |
| 223 | K19T | D59N | I96L | S164G | L222I | G251D | | | | 77 |
| 224 | Y11I | K19T | D59N | I96V | L222I | R242D | G251D | | | 78 |
| 225 | K19S | D59N | I96V | S164G | G251D | | | | | 86 |
| 226 | K19S | I96L | S164G | L166V | L222I | R242E | | | | 43 |
| 227 | K19T | D59N | I96L | S164G | L166V | L222I | R242D | G251D | L253I | 59 |
| 228 | D59N | I96L | S164G | L222I | R242E | L253I | I263L | | | 59 |
| 229 | K19T | D59N | E83T | I96L | L222I | G251D | I263L | | | 93 |
| 230 | Y11I | K19T | D59N | S164G | L222I | G251D | I263V | | | 56 |
| 231 | K19T | D59N | I96L | S164G | L166I | G251D | L253V | | | 83 |
| 232 | K19T | I96V | S164G | L222I | N249D | G251D | L253I | | | 79 |
| 233 | K19T | I96L | L222I | R242E | L253I | | | | | 89 |
| 234 | K19T | E83S | I96L | S164G | L222I | R242E | G251D | L253I | | 58 |
| 235 | D59N | E83T | I96L | S164N | L222V | G251D | | | | 101 |
| 236 | K19S | D59N | I96L | S164G | L222I | R242E | N249E | G251D | | 54 |
| 237 | K19T | I96L | S164G | L166V | L222I | N249D | I263L | | | 63 |
| 238 | D59N | I96L | L166V | L222I | R242E | G251D | | | | 77 |
| 239 | K19T | D59N | E83T | S164G | L166V | L222I | R242E | G251D | | 76 |
| 240 | Y11I | K19T | D59N | E83S | I96L | S164G | L222I | N249D | | 37 |
| 241 | K19T | E83T | I96L | S164G | L222I | R242E | L253V | | | 68 |
| 242 | K19T | D59N | I96L | S164G | L166I | L222I | R242E | N249D | | 66 |
| 243 | Y11V | K19T | D59N | I96L | S164G | L166V | L222I | R242E | G251D | L253I | 47 |
| 244 | K19T | I96L | S164N | L222I | R242E | I263L | | | | 73 |
| 245 | Y11V | D59N | I96L | S164G | L222I | G251D | L253V | | | 51 |
| 246 | K19T | D59N | I96V | S164G | L166V | L222I | R242E | I263L | | 47 |
| 247 | Y11V | K19T | D59N | S164N | L166I | L222I | G251D | | | 45 |
| 248 | K19T | I96L | S164G | L166V | L222I | R242E | N249D | G251D | I263V | 57 |
| 249 | K19T | I96L | S164G | R242E | L253I | | | | | 69 |
| 250 | K19S | D59N | E83S | I96L | S164N | L222I | G251D | | | 93 |
| 251 | K19T | D59N | I96L | S164G | L222V | N249E | G251D | I263V | | 72 |
| 252 | K19T | D59N | I96L | S164G | L222I | N249E | G251D | L253V | I263L | 71 |
| 253 | Y11I | K19T | I96L | S164G | L222V | R242E | G251D | | | 39 |
| 254 | I96L | S164G | L222I | R242E | N249D | G251D | I263L | | | 58 |
| 255 | K19T | D59N | I96L | S164G | L166I | L222I | R242D | G251D | I263V | 65 |
| 256 | K19T | D59N | I96L | S164G | L222V | R242E | N249D | L253I | | 65 |
| 257 | H76Q | I96L | S164G | L222I | R242E | G251D | S273Y | | | 45 |
| 258 | K19T | E83S | I96L | S164G | L222I | R242E | N249D | G251D | L253I | 67 |
| 259 | I96L | S164G | L166V | L222I | R242E | N249D | I263L | | | 51 |
| 260 | Y11V | K19T | E83S | I96L | S164G | L166V | L222I | R242E | G251D | 46 |
| 261 | Y11V | K19T | I96L | S164G | L166V | L222I | R242E | | | 39 |
| 262 | Y11V | E83S | I96L | S164G | L222I | R242E | G251D | L253I | I263L | 40 |
| 263 | Y11V | I96L | S164G | L222I | R242E | N249D | L253I | I263L | | 41 |
| 264 | K19T | I96L | S164G | L166V | L222I | R242E | N249D | I263L | | 43 |
| 265 | Y11V | E83S | I96L | S164G | L222I | R242E | L253I | I263L | | 46 |
| 266 | K19T | E83S | I96L | S164G | L166V | L222I | R242E | N249D | G251D | L253I | 74 |
| 267 | I96L | S164G | L222I | R242E | G251D | S273Y | | | | 67 |
| 268 | H76Q | I96L | S164G | L222I | R242E | G251D | | | | 54 |
| 269 | I96L | S164G | L222I | R242E | G251D | | | | | 72 |

TABLE 9

Mutational contributions (mean) to altered αS1-casein cleavage and standard deviations (sd) based on statistical analysis. Positive mean values represent decreased αS1-casein cleavage. Negative mean values represent increased αS1-casein cleavage.

| mutation | mean | sd |
|---|---|---|
| Y11I | 7.41E−01 | 9.83E−02 |
| Y11V | 6.79E−01 | 4.09E−02 |
| S164G | 4.73E−01 | 3.77E−02 |
| H76Q | 3.59E−01 | 6.78E−02 |
| L222V | 2.34E−01 | 5.61E−02 |
| I96L | 1.79E−01 | 5.29E−02 |
| K19S | 1.73E−01 | 8.05E−02 |
| L222I | 1.71E−01 | 3.20E−02 |
| I263L | 1.54E−01 | 4.94E−02 |
| L166V | 1.54E−01 | 3.65E−02 |
| S273Y | 1.17E−01 | 7.37E−02 |
| R242E | 1.11E−01 | 5.68E−02 |
| S164N | 9.78E−02 | 6.20E−02 |
| G251D | −1.64E−01 | 4.79E−02 |
| L253V | −2.11E−01 | 3.87E−02 |

Based on the results shown in table 9 it is concluded that mutations Y11I, Y11V, K19S, H76Q, I96L, S164G, S164N, L166V, L222I, L222V, R242E, I263L, and S273Y lead to decreased cleavage of αS1-casein between Phe23 and Phe24. Since these mutations cause less generation of αS1(1-23), they represent preferred mutations in chymosin variants for cheese manufacturing processes that require less softening of the cheese curd during ripening. Mutations L253V and G251 D lead to increased cleavage of αS1-casein between Phe23 and Phe24. Since these mutations cause higher generation of αS1(1-23), they represent preferred mutations in chymosin variants for cheese manufacturing processes that require more softening of the cheese curd during ripening.

Structure-Based Variations in Camel Chymosin

Variants of camel chymosin (SEQ ID NO:2) were made with amino acid changes in positions determined by protein structural analysis (Tab. 10). Mutations N100Q and N291Q were introduced into both N-glycosylation sites of these variants and the reference camel chymosin (CamUGly) to yield non-glycosylated, homogeneous protein samples.

Clotting activities were determined using the pIMCU method.

TABLE 10

Cleavage of αS1-casein between amino acids Phe23 and Phe24 (yielding the N-terminal peptide αS1N) by camel chymosin variants 270-308. Numbers are given in % cleavage of wild type camel chymosin (CamUGly).

| variant | mutations | | αS1N |
|---|---|---|---|
| CamUGly | N100Q | N291Q | 100 |
| 270 | V32L | N100Q | N291Q | 120 |
| 271 | V221K | N100Q | N291Q | 130 |
| 272 | D290E | N100Q | N291Q | 100 |
| 273 | V136I | N100Q | N291Q | 105 |
| 274 | E240Q | N100Q | N291Q | 97 |
| 275 | R242Q | N100Q | N291Q | 86 |
| 276 | G289S | N100Q | N291Q | 81 |
| 277 | N292H | N100Q | N291Q | 127 |
| 278 | L295K | N100Q | N291Q | 113 |
| 279 | V136E | N100Q | N291Q | 100 |
| 280 | D290L | N100Q | N291Q | 106 |
| 281 | F119Y | N100Q | N291Q | 83 |
| 282 | Q280E | N100Q | N291Q | 94 |
| 283 | F282E | N100Q | N291Q | 99 |
| 284 | N249D | N100Q | N291Q | 98 |
| 285 | R254S | N100Q | N291Q | 95 |
| 286 | R242E | N100Q | N291Q | 86 |
| 287 | N252D | N100Q | N291Q | 93 |
| 288 | V203R | N100Q | N291Q | 107 |
| 289 | N249R | N100Q | N291Q | 95 |
| 290 | H56K | N100Q | N291Q | 106 |
| 291 | S74D | N100Q | N291Q | 93 |
| 292 | A131D | N100Q | N291Q | 101 |
| 293 | Y190A | N100Q | N291Q | 87 |
| 294 | I297A | N100Q | N291Q | 149 |
| 295 | H76Q | N100Q | N291Q | 73 |
| 296 | S273Y | N100Q | N291Q | 89 |
| 297 | K19T | N100Q | N291Q | 89 |
| 299 | L222I | N100Q | N291Q | 92 |
| 300 | V309I | N100Q | N291Q | 96 |
| 302 | Y21S | N100Q | N291Q | 108 |
| 303 | L130I | N100Q | N291Q | 110 |
| 304 | S132A | N100Q | N291Q | 112 |
| 305 | S226T | N100Q | N291Q | 94 |
| 306 | G251D | N100Q | N291Q | 105 |
| 307 | Y243E | N100Q | N291Q | 98 |
| 308 | S273D | N100Q | N291Q | 99 |

Based on the results shown in table 10 it is concluded that mutations K19T, H76Q, F119Y, Y190A, R242E, R242Q, S273Y, and G289S decreased cleavage of αS1-casein between Phe23 and Phe24 by more than 10%. Since these mutations cause less generation of αS1(1-23), they represent preferred mutations in chymosin variants for cheese manufacturing processes that require less softening of the cheese curd during ripening. V32L, L130I, S132A, V221K, N292H, L295K, and I297A increased cleavage of αS1-casein between Phe23 and Phe24 by at least 10%. Since these mutations cause higher generation of αS1(1-23), they represent preferred mutations in chymosin variants for cheese manufacturing processes that require more softening of the cheese curd during ripening. A similar effect of mutations H76Q, S273Y, R242E and V32L, S132A, V221K, L295K on decreased and increased αS1-casein cleavage, respectively, was determined by mutational analysis of multi-substitution libraries 1-6 (tables 5, 7, 9).

Fourteen out of 15 variants from table 10 that showed more than 10% decreased or increased cleavage of αS1-casein between Phe23 and Phe24 bear mutations (H76Q, F119Y, Y190A, R242E, R242Q, S273Y, G289S, V32L, L130I, S132A, V221K, N292H, L295K, I297A) within or in structural proximity to the substrate binding cleft (FIG. 2), suggesting a direct impact of these mutations on β-casein binding.

Structure-Based Variations in Bovine Chymosin

Variants of bovine chymosin (SEQ ID NO:1) were made with amino acid changes in positions determined by protein structural analysis (Tab. 11). Mutations N252Q and N291Q were introduced into both N-glycosylation sites of these variants and the reference bovine chymosin (BovUGly) to yield non-glycosylated, homogeneous protein samples.

Clotting activities were determined using the pIMCU method.

TABLE 11

Cleavage of αS1-casein between amino acids Phe23 and Phe24 (yielding the N-terminal peptide αS1N) by bovine chymosin variants 326-346. Numbers are given in % cleavage of wild type bovine chymosin (BovUGly).

| variant | mutations | | | αS1N |
|---|---|---|---|---|
| BovUGly | | N252Q | N291Q | 100 |
| 326 | E290D | N252Q | N291Q | 95 |
| 327 | A117S | N252Q | N291Q | 87 |
| 328 | I136V | N252Q | N291Q | 95 |
| 330 | Q278K | N252Q | N291Q | 97 |
| 332 | H292N | N252Q | N291Q | 90 |
| 334 | K295L | N252Q | N291Q | 94 |
| 338 | Q56H | N252Q | N291Q | 103 |
| 339 | L32I | N252Q | N291Q | 93 |
| 340 | K71E | N252Q | N291Q | 67 |
| 341 | P72T | N252Q | N291Q | 103 |
| 342 | Q83T | N252Q | N291Q | 110 |
| 343 | V113F | N252Q | N291Q | 72 |
| 344 | E133S | N252Q | N291Q | 114 |
| 345 | Y134G | N252Q | N291Q | 102 |
| 346 | K71A | N252Q | N291Q | 96 |

Mutations K71E, V113F, and A117 decreased cleavage of αS1-casein between Phe23 and Phe24 by more than 10% as shown in table 11. Since these mutations cause less generation of αS1(1-23), they represent preferred mutations in chymosin variants for cheese manufacturing processes that require less softening of the cheese curd during ripening. Mutations Q83T and E133S increased cleavage of αS1-casein between Phe23 and Phe24 by at least 10%. Since these mutations cause higher generation of αS1(1-23), they represent preferred mutations in chymosin variants for cheese manufacturing processes that require more softening of the cheese curd during ripening.

Variations of the Camel Chymosin N-Terminus

Variants of camel chymosin (SEQ ID NO:2) were made with amino acid changes in positions determined by protein structural analysis of the molecular interactions of the N-terminal sequence Y11-D13 within the substrate binding cleft (Tab. 12). Mutations N100Q and N291Q were introduced into both N-glycosylation sites of these variants and the reference camel chymosin (CamUGly) to yield non-glycosylated, homogeneous protein samples.

Clotting activities were determined using the pIMCU method.

TABLE 12

Cleavage of αS1-casein between amino acids Phe23 and Phe24 (yielding the N-terminal peptide αS1N) by camel chymosin variants 347-366. Numbers are given in % cleavage of wild type camel chymosin (CamUGly).

| variant | mutations | | | αS1N |
|---|---|---|---|---|
| CamUGly | | | N100Q N291Q | 100 |
| 347 | Y11H | | N100Q N291Q | 96 |
| 348 | Y11K | | N100Q N291Q | 100 |
| 349 | Y11R | | N100Q N291Q | 97 |
| 350 | Y11H | D290E | N100Q N291Q | 94 |
| 351 | Y11R | D290E | N100Q N291Q | 81 |
| 352 | Y11F | | N100Q N291Q | 100 |
| 353 | Y11I | | N100Q N291Q | 89 |
| 354 | Y11L | | N100Q N291Q | 89 |
| 355 | Y11V | | N100Q N291Q | 95 |
| 356 | L12F | | N100Q N291Q | 102 |
| 357 | L12I | | N100Q N291Q | 104 |
| 358 | L12M | | N100Q N291Q | 123 |
| 359 | D13N | | N100Q N291Q | 119 |
| 360 | D13Q | | N100Q N291Q | 109 |
| 361 | D13S | | N100Q N291Q | 114 |
| 362 | D13T | | N100Q N291Q | 119 |
| 363 | D13F | | N100Q N291Q | 106 |
| 364 | D13L | | N100Q N291Q | 109 |
| 365 | D13V | | N100Q N291Q | 120 |
| 366 | D13Y | | N100Q N291Q | 107 |

Analysis of the camel chymosin structure guided variations in the N-terminal sequence Y11-D13 as well as in position D290, a potential interaction partner of Y11 (FIG. 3). Since casein substrates compete with the N-terminal chymosin sequence for binding within the binding cleft, amino acid substitutions that change interactions between binding cleft and the motif Y11-D13 are expected to impact enzymatic activity toward various casein substrates and, thus, cleavage of αS1-casein. Mutations Y11I and Y11V, as well as the combination of Y11R and D290E decreased cleavage of αS1-casein between Phe23 and Phe24 by more than 10% as shown in table 12. Since these mutations cause less generation of αS1(1-23), they represent preferred mutations in chymosin variants for cheese manufacturing processes that require less softening of the cheese curd during ripening. Since neither Y11R (variant 349, table 12) nor D290E (variant 272, table 10) show significant impact on cleavage of αS1-casein alone, the altered proteolytic activity of variant 351 is most likely caused by synergistic effects of both mutations.

Mutations L12M, D13N, D13S, D13T and D13V increased cleavage of αS1-casein between Phe23 and Phe24 by at least 10%. Since these mutations cause higher generation of αS1(1-23), they represent preferred mutations in chymosin variants for cheese manufacturing processes that require more softening of the cheese curd during ripening.

Multi-Substitution Library 6

Another set of camel chymosin variants, each having multiple substitutions compared to wild type, were generated and analyzed as described above. All variants have an amino acid sequence identical to camel chymosin (SEQ ID NO:2), except for the variations mentioned in the table. Camel chymosin (CHY-MAX M) is included as reference.

Clotting activities were determined using the pIMCU method.

TABLE 13

Cleavage of αS1-casein between amino acids Phe23 and Phe24 (yielding the N-terminal peptide αS1N) by camel chymosin variants 367-416. Numbers are given in % cleavage of wild type camel chymosin (CHY-MAX M).

| variant | mutations | | | | | | αS1N |
|---|---|---|---|---|---|---|---|
| CHY-MAX M | | | | | | | 100 |
| 367 | R67Q | N100Q | L130I | M157L | V248I | N291Q | 145 |
| 368 | N100Q | L130I | S132A | M157L | K231N | | 148 |
| 369 | R67Q | I96L | L130I | M157L | L222I | M256L | 106 |
| 370 | R67Q | L130I | S132A | M157L | R242E | V248I | 98 |
| 371 | R67Q | N100Q | M157L | R242E | M256L | | 99 |
| 372 | R67Q | G70D | M157L | R242E | V248I | | 84 |
| 373 | V32L | R67Q | M157L | L222I | R242E | | 97 |
| 374 | Y11V | R67Q | M157L | V248I | M256L | | 88 |
| 375 | R67Q | V136I | M157L | L222I | V248I | | 64 |
| 376 | L130I | M157L | V248I | M256L | N291Q | | 127 |
| 377 | R67Q | I96L | L130I | M157L | K231N | R242E | 92 |
| 378 | V32L | R67Q | L130I | M157L | L222I | K231N | 113 |
| 379 | L130I | V136I | M157L | L222I | N292H | | 111 |
| 380 | R67Q | G70D | M157L | L222I | N291Q | | 106 |
| 381 | V32L | R67Q | L130I | K231N | N292H | | 125 |
| 382 | Y11V | R67Q | N100Q | L130I | V136I | M157L | 107 |
| 383 | R67Q | L130I | L222I | R242E | M256L | | 87 |
| 384 | R67Q | M157L | L222I | V248I | N292H | | 96 |
| 385 | V32L | R67Q | M157L | M256L | N291Q | | 117 |
| 386 | R67Q | L130I | S132A | M157L | L222I | N292H | 97 |
| 387 | R67Q | N100Q | L130I | M157L | K231N | N291Q | 139 |
| 388 | R67Q | L130I | K231N | V248I | N291Q | | 131 |
| 389 | Y11V | R67Q | L130I | M157L | L222I | K231N | 82 |
| 390 | I45V | L130I | M157L | K231N | R242E | | 91 |
| 391 | V32L | R67Q | V136I | M157L | N291Q | | 128 |
| 392 | R67Q | N100Q | L130I | D158S | V248I | | 134 |
| 393 | I45V | R67Q | L130I | M157L | L222I | K231N | 106 |
| 394 | V32L | R67Q | L130I | S132A | M157L | V248I | 117 |
| 395 | Y11V | R67Q | L130I | M157L | N291Q | N292H | 91 |
| 396 | R67Q | N100Q | L130I | M157L | L222I | K231N | 120 |
| 397 | I45V | R67Q | G70D | L130I | S132A | | 98 |
| 398 | I45V | R67Q | L130I | V248I | N292H | | 108 |
| 399 | Y11V | R67Q | L130I | M157L | L222I | R242E | 73 |
| 400 | R67Q | N100Q | D158S | L130I | M157L | L222I | 116 |
| 401 | R67Q | L130I | V136I | M157L | K231N | V248I | 109 |
| 402 | I45V | R67Q | L130I | L222I | N291Q | | 118 |
| 403 | R67Q | G70D | L130I | M157L | K231N | M256L | 107 |
| 404 | V32L | R67Q | L130I | M157L | D158S | V248I | 112 |
| 405 | L130I | M157L | D158S | R242E | N291Q | | 62 |
| 406 | R67Q | L130I | M157L | D158S | K231N | N292H | 103 |
| 407 | R67Q | L130I | V248I | M256L | N292H | | 120 |
| 408 | V32L | R67Q | I96L | L130I | M157L | V248I | 108 |
| 409 | R67Q | I96L | N100Q | L130I | M157L | N292H | 73 |
| 410 | V32L | R67Q | G70D | N100Q | M157L | | 132 |
| 411 | V32L | R67Q | L130I | M157L | K231N | M256L | 63 |
| 412 | R67Q | I96L | M157L | L222I | K231N | | 105 |
| 413 | R67Q | M157L | L222I | K231N | V248I | | 108 |
| 414 | R67Q | L130I | M157L | R242E | M256L | N292H | 95 |
| 415 | R67Q | L222I | K231N | V248I | | | 106 |
| 416 | R67Q | S132A | L222I | K231N | R242E | V248I | 88 |

In table 13 are shown camel chymosin variants with data on cleavage of αS1-casein between Phe23 and Phe24. Out of 50 library variants, 10 reveal between 12% and 48% reduced proteolytic activity compared to wild type camel chymosin. Another 18 variants reveal between 11% and 48% increased proteolytic activity compared to wild type camel chymosin.

Mutational Analysis of Multi-Substitution Library 6

A statistical analysis of the positional and mutational effects on αS1-casein cleavage was performed based on the proteolytic data of library 6 variants. The most beneficial mutations for increased or decreased αS1-casein cleavage are shown in table 14.

TABLE 14

Mutational contributions (mean) to altered αS1-casein cleavage and standard deviations (sd) based on statistical analysis. Positive mean values represent decreased αS1-casein cleavage. Negative mean values represent increased αS1-casein cleavage.

| mutation | mean | sd |
|---|---|---|
| Y11V | 5.14E−01 | 2.20E−02 |
| R242E | 3.82E−01 | 1.98E−02 |
| G70D | 8.96E−02 | 2.13E−02 |
| R67Q | 7.87E−02 | 2.85E−02 |
| L222I | 7.48E−02 | 1.56E−02 |
| M256L | −3.63E−02 | 1.73E−02 |
| V248I | −4.27E−02 | 1.94E−02 |

TABLE 14-continued

Mutational contributions (mean) to altered αS1-casein cleavage and standard deviations (sd) based on statistical analysis. Positive mean values represent decreased αS1-casein cleavage. Negative mean values represent increased αS1-casein cleavage.

| mutation | mean | sd |
|---|---|---|
| K231N | −5.17E−02 | 1.67E−02 |
| V136I | −8.22E−02 | 2.13E−02 |
| L130I | −9.71E−02 | 1.78E−02 |
| V32L | −1.75E−01 | 2.07E−02 |
| N291Q | −1.99E−01 | 1.65E−02 |
| N100Q | −3.72E−01 | 1.79E−02 |

Based on the results shown in table 14 it is concluded that mutations Y11V, R242E, G70D, R67Q, and L222I lead to decreased cleavage of αS1-casein between Phe23 and Phe24. Since these mutations cause less generation of αS1 (1-23), they represent preferred mutations in chymosin variants for cheese manufacturing processes that require less softening of the cheese curd during ripening. Mutations N100Q, N291Q, V32L, L130I, V136I, K231N, V248I, and M256L lead to increased cleavage of αS1-casein between Phe23 and Phe24. Since these mutations cause higher generation of αS1(1-23), they represent preferred mutations in chymosin variants for cheese manufacturing processes that require more softening of the cheese curd during ripening.

Multi-Substitution Library 7

Another set of camel chymosin variants, each having multiple substitutions compared to wild type, were generated and analyzed as described above. All variants have an amino acid sequence identical to camel chymosin (SEQ ID NO: 2), except for the variations mentioned in the table. Camel chymosin (CHY-MAX M) is included as reference.

Clotting activities were determined using the REMCAT method.

TABLE 15

Cleavage of αS1-casein between amino acids Phe23 and Phe24 (yielding the N-terminal peptide αS1N) by camel chymosin variants 417-461, as well as specific clotting activities (C), general proteolytic activities (P) and C/P values. Numbers are given in % cleavage of wild type camel chymosin (CHY-MAX M).

| variant | mutations | | | | | | | | | | αS1N | Clotting (C) | Proteolytic (P) | C/P |
|---|---|---|---|---|---|---|---|---|---|---|---|---|---|---|
| CHY-MAX M | | | | | | | | | | | 100 | 100 | 100 | 100 |
| 417 | Y11V | K19T | D59N | | S164G | L166V | L222I | R242E | N249E | G251D | 45 | 132 | 20 | 651 |
| 418 | Y11V | K19T | D59N | I96L | S164G | L166V | L222I | R242E | N249E | G251D | 42 | 114 | 21 | 556 |
| 419 | Y11I | K19T | D59N | I96L | S164G | L166V | L222I | R242E | N249E | G251D | 32 | 108 | 20 | 554 |
| 420 | Y11I | K19T | D59N | I96L | S164G | L166I | L222I | R242E | | G251D | 38 | 98 | 11 | 898 |
| 421 | Y11V | K19T | D59N | I96L | | L166V | L222V | R242E | N249E | G251D L253I | 35 | 132 | 84 | 156 |
| 422 | Y11V | K19T | D59N | I96L | S164G | L166V | | R242E | | | 45 | 105 | 13 | 802 |
| 423 | Y11V | K19T | D59N | I96L | S164G | | L222V | R242E | | G251D | 46 | 89 | 8 | 1131 |
| 424 | Y11V | K19T | D59N | I96L | S164G | L166I | | R242E | N249E | G251D L253I | 43 | 93 | 8 | 1111 |
| 425 | Y11V | K19T | D59N | I96L | S164G | L166V | L222V | R242E | N249E | G251D | 26 | 105 | 18 | 572 |
| 426 | Y11V | K19T | D59N | I96L | S164G | L166I | L222V | R242E | N249E | G251D L253I | 30 | 93 | 18 | 512 |
| 427 | Y11V | K19T | D59N | | | L166V | L222I | R242E | N249E | G251D L253I | 54 | 137 | 42 | 323 |
| 428 | Y11V | K19T | D59N | I96L | S164G | L166V | L222I | R242E | N249E | | 36 | 120 | 15 | 803 |
| 429 | Y11V | K19T | D59N | | S164G | L166I | L222I | R242E | | G251D | 53 | 107 | 17 | 630 |
| 430 | Y11V | K19T | D59N | I96L | S164G | | | R242E | | G251D | 48 | 89 | 11 | 801 |
| 431 | Y11V | | D59N | I96L | S164G | L166I | L222V | R242E | | G251D L253I | 41 | 79 | 28 | 283 |
| 432 | Y11V | | D59N | I96L | S164G | L166I | L222I | R242E | | G251D | 39 | 102 | 24 | 432 |
| 433 | Y11I | | D59N | I96L | S164G | L166V | L222V | R242E | | G251D L253I | 18 | 97 | 25 | 392 |
| 434 | Y11V | K19T | D59N | I96L | S164G | | L222I | R242E | N249E | G251D | 42 | 99 | 33 | 301 |
| 435 | Y11V | K19T | D59N | I96L | S164G | L166I | L222V | R242E | | G251D | 49 | 88 | 17 | 514 |
| 436 | Y11V | K19T | D59N | I96L | S164G | L166V | L222V | R242E | N249E | L253I | 33 | 95 | 10 | 949 |
| 437 | Y11V | K19T | D59N | I96L | S164G | L166I | L222V | R242E | N249E | G251D | 39 | 114 | 22 | 520 |
| 438 | Y11I | K19T | | I96L | S164G | L166V | | R242E | N249E | G251D | 40 | 93 | 7 | 1262 |
| 439 | Y11V | K19T | D59N | I96L | S164G | L166V | L222V | R242E | | G251D | 36 | 108 | 26 | 423 |
| 440 | Y11V | K19T | D59N | I96L | S164G | | L222V | R242E | N249E | G251D | 52 | 105 | 9 | 1196 |
| 441 | Y11I | K19T | | | | | L222V | R242E | N249E | G251D | 67 | 122 | 26 | 469 |
| 442 | Y11I | K19T | | I96L | | | L222V | R242E | N249E | G251D | 60 | 105 | 21 | 503 |
| 443 | Y11I | K19T | D59N | I96L | S164G | L166V | L222V | R242E | N249E | G251D | 31 | 105 | 18 | 595 |
| 444 | Y11V | K19T | | I96L | S164G | L166V | L222V | R242E | N249E | G251D | 38 | 96 | 8 | 1242 |
| 445 | Y11I | K19T | D59N | I96L | S164G | L166I | L222V | R242E | N249E | G251D | 38 | 82 | 12 | 707 |
| 446 | Y11I | | | I96L | S164G | L166V | L222V | R242E | N249E | G251D | 28 | 95 | 16 | 579 |
| 447 | Y11I | K19T | D59N | I96L | S164G | | L222V | R242E | N249E | | 45 | 90 | 11 | 790 |
| 448 | Y11I | K19T | D59N | | I96L | | L222V | R242E | N249E | G251D | 41 | 153 | 40 | 381 |
| 449 | Y11I | K19T | D59N | I96L | S164G | | L222I | R242E | | | 39 | 89 | 16 | 564 |
| 450 | Y11I | K19T | D59N | I96L | S164G | L166V | | R242E | | G251D | 36 | 88 | 5 | 1686 |
| 451 | Y11I | K19T | D59N | | S164G | L166I | L222V | R242E | | G251D | 51 | 93 | 21 | 440 |
| 452 | Y11I | | | I96L | | | L222V | R242E | N249E | G251D | 49 | 122 | 22 | 566 |
| 453 | Y11I | | | I96L | S164G | | L222I | R242E | | | 40 | 74 | 5 | 1375 |
| 454 | Y11V | K19T | | I96L | | L166V | L222V | R242E | | G251D | 29 | 119 | 52 | 228 |
| 455 | Y11I | | D59N | I96L | S164G | | L222I | R242E | | G251D | 42 | 105 | 9 | 1139 |
| 456 | Y11I | | D59N | I96L | S164G | | L222V | R242E | | G251D | 43 | 95 | 15 | 615 |
| 457 | Y11I | K19T | D59N | I96L | S164G | | L222I | R242E | N249E | G251D | 40 | 101 | 7 | 1419 |
| 458 | Y11I | | D59N | I96L | S164G | L166V | L222V | R242E | | G251D | 25 | 89 | 16 | 572 |
| 459 | Y11V | K19T | D59N | I96L | | | L222V | R242E | | G251D | 52 | 143 | 62 | 230 |
| 460 | Y11I | K19T | | | S164G | L166I | L222I | R242E | N249E | G251D | 44 | 80 | 13 | 625 |
| 461 | Y11I | | D59N | I96L | S164G | L166V | L222V | R242E | N249E | G251D | 25 | 96 | 35 | 273 |

In table 15 are shown camel chymosin variants with data on cleavage of αS1-casein between Phe23 and Phe24, as well as specific clotting activities (C), general proteolytic activities (P) and C/P values. All variants reveal between 33% and 82% reduced αS1-casein cleavage.

Mutational Analysis of Multi-Substitution Library 7

A statistical analysis of the positional and mutational effects on αS1-casein cleavage was performed based on the proteolytic data of library 7 variants. The most beneficial mutations for decreased αS1-casein cleavage are shown in table 16.

TABLE 16

Mutational contributions (mean) to altered αS1-casein cleavage and standard deviations (sd) based on statistical analysis. Positive mean values represent decreased αS1-casein cleavage.

| mutation | mean | sd |
| --- | --- | --- |
| I96L | 2.61E-01 | 1.79E-02 |
| L166V | 2.25E-01 | 1.45E-02 |
| R242E | 2.03E-01 | 5.96E-02 |
| Y11I | 1.51E-01 | 3.31E-02 |
| L222I | 1.43E-01 | 2.15E-02 |
| L222V | 1.39E-01 | 1.62E-02 |
| S164G | 1.18E-01 | 2.22E-02 |
| L166I | 9.00E-02 | 1.76E-02 |
| L253I | 5.86E-02 | 1.90E-02 |
| Y11V | 5.28E-02 | 2.75E-02 |

Based on the results shown in table 16 it is concluded that mutations I96L, L166V, R242E, Y11I, L222I, L222V, S164G, L166I, L253I, and Y11V lead to decreased cleavage of αS1-casein between Phe23 and Phe24. Since these mutations cause less generation of αS1(1-23), they represent preferred mutations in chymosin variants for cheese manufacturing processes that require less softening of the cheese curd during ripening.

REFERENCES

1. A. Kumar, S. Grover, J. Sharma, V. K. Batish, Crit. Rev. Biotechnol. 2010, 30, 243-258.
2. M. W. Bursting, K. B. Qvist, M. Rasmussen, J. Vindeløv, F. K. Vogensen, Y. Ardö, Dairy Sci. 2012, 92, 593-612.
3. K. Kastberg Møller, F. P. Rattray, Y. Ardö, J. Agric. Food Chem. 2012, 60, 11421-11432.
4. P. L. H. McSweeney, Int. J. Dairy Technol. 2004, 57, 127-144.
5. J. Langholm Jensen, A. Mølgaard, J.-C. Navarro Poulsen, M. K. Harboe, J. B. Simonsen, A. M. Lorentzen, K. Hjernø, J. M. van den Brink, K. B. Qvist, S. Larsen, Acta Cryst. 2013, D69, 901-913.
6. S. Chitpinityol, D. Goode, M. J. C. Crabbe, Food Chem. 1998, 62, 133-139.
7. G. L. Gilliland, E. L. Winborne, J. Nachman, A. Wlodawer, Proteins 1990, 8, 82-101.
8. D. S. Palmer, A. U. Christensen, J. Sørensen, L. Celik, K. Bruun Qvist, B. Schiøtt, Biochemistry 2010, 49, 2563-2573.
9. J. Sørensen, D. S. Palmer, B. Schiøtt, J. Agric. Food Chem. 2013, 61, 7949-7959.
10. I. Schechter, A. Berger, Biochem. Biophys. Res. Commun. 1967, 425, 497-502.
11. L. K. Creamer, N. F. Olsen, J. Food Sci. 1982, 47:631-636
12. N. Bansal, M. A. Drake, P. Piraino, M. L. Broe, M. Harboe, P. F. Fox, P. L. H. McSweeney, Int. Dairy J. 2009, 19:510-517.
13. A. C. Moynihan, S. Govindasamy-Lucey, J. J. Jaeggi, M. E. Johnson, J. A. Lucey, P. L. H. McSweeney, J. Dairy Sci. 2014, 97:85-96.
14 J. Ehren, S. Govindarajan, B. Moron, J. Minshull, C. Khosla, Prot. Eng. Des. Sel. 2008, 21, 699-707.
15. S. Govindarajan, B. Mannervik, J. A. Silverman, K. Wright, D. Regitsky, U. Hegazy, T. J. Purcell, M. Welch, J. Minshull, C. Gustafsson, ACS Synth. Biol. 2015, 4, 221-227.
16. M. Newman, M. Safro, C. Frazao, G. Khan, A. Zdanov, I. J. Tickle, T. L. Blundell, N. Andreeva, J. Mol. Biol. 1991, 221, 1295-1309.
17. E. Gustchina, L. Rumsh, L. Ginodman, P. Majer, N. Andreeva, FEBS Lett. 1996, 379, 60-62.
18. S. Visser, C. J. Slangen, P. J. van Rooijen, Biochem. J. 1987, 244, 553-558.

The invention claimed is:

1. An isolated chymosin polypeptide variant having an alteration in its amino acid sequence relative to a parent polypeptide having chymosin activity, wherein the alteration comprises a substitution at amino acid position S164 of the parent polypeptide, wherein:
   (a) the amino acid position of the parent polypeptide is determined by alignment of the parent polypeptide with the polypeptide of SEQ ID NO: 4,
   (b) the parent polypeptide of the variant has at least 80% sequence identity SEQ ID NO: 4;
   (c) the isolated chymosin polypeptide variant has a ratio of clotting activity to proteolytic activity (C/P value) that is at least 200% of the C/P value of isolated camel chymosin having the amino acid sequence of SEQ ID NO:4;
   (d) the isolated chymosin polypeptide variant cleaves αS1-casein with a frequency of less than 80% of the frequency of αS1-casein cleavage by isolated camel chymosin having the amino acid sequence of SEQ ID NO: 4, as determined by quantifying αS1-casein peptides obtained by incubating skim milk with the chymosin polypeptide variant or the camel chymosin, wherein quantification is carried out by RP-HPLC coupled to an ESI-Q-TOF mass spectrometer; and
   (e) the variant has fewer than 30 amino acid alterations as compared to SEQ ID NO: 4 as determined by an alignment of the amino acid sequence of the variant with the amino acid sequence of SEQ ID NO: 4.

2. The isolated chymosin polypeptide variant of claim 1, wherein the alteration is S164G.

3. The isolated chymosin polypeptide variant of claim 1, wherein the variant comprises substitutions selected from:
   D59N+H76Q+I96L+L130I+S164G+L222I+R242E+ G251D,
   H76Q+I96L+S164G+L222I+R242E+G251D+S273Y,
   K19T+D59N+H76Q+I96L+S164G+L166V+L222I+ G251D+S273Y,
   H76Q+S164G+L166V+L222I+R242E+G251D+S273Y,
   Y21S+H76Q+S164G+L222I+R242E+G251D+S273Y,
   D59N+H76Q+I96L+S132A+S164G+L222I+S226T+ G251D+S273Y,
   D59N+H76Q+I96L+S132A+S164G+L166V+L222I+ G251D+S273Y,
   H76Q+I96L+S164G+G251D+S273Y+V309I,
   Y21S+D59N+H76Q+S164G+L222I+S226T+G251D+ S273Y+V309 I
   H76Q+S164G+L166V+L222I+S226T+S273Y,
   D59N+H76Q+L130I+S164G+L166V+L222I+G251D+ S273Y+V309I,
   D59N+H76Q+S164G+L222I+S226T+R242E,
   K19T+D59N+I96L+S164G+L222I+G251D,
   D59N+H76Q+I96L+S164G+L222I+S226T+G251D+ S273Y+V309I,
   D59N+H76Q+L130I+S164G+G251D+V309I,
   K19T+D59N+S164G+L166V+L222I+S226T+G251D+ S273Y,
   D59N+H76Q+L130I+S132A+S164G+L222I+R242E+ G251D+S273Y,
   K19T+Y21S+H76Q+S164G+L222I+G251D+S273Y,
   D59N+H76Q+S164G+L222I+R242E+S273Y+V309I,
   K19T+Y21S+D59N+H76Q+S132A+S164G+L222I+ G251D+S273Y, K19T+D59N+H76Q+L130I+S164G+L222I+S226T+
G251D+S273Y,
K19T+Y21S+D59N+H76Q+L130I+S164G+L222I+
S273Y,
Y21S+D59N+S164G+L222I+R242E+G251D+S273Y+
V309I,
D59N+H76Q+S132A+S164G+L166V+S273Y,
K19S+I96L+S164G+L166V+L222I+R242E,
K19T+D59N+I96V+S164G+L166V+L222I+R242E+
I263L,
H76Q+I96L+S164G+L222I+R242E+G251D,
K19T+E83S+I96L+S164G+L222I+R242E+G251D+
L253I ,
K19T+D59N+I96L+S164G+L166V+L222I+R242D+
G251D+L253I ,
D59N+I96L+S164G+L222I+R242E+L253I+I263L,
K19T+D59N+I96L+S164G+L166I+L222I+R242D+
G251D+I263V,
I96L+S164G+L222I+R242E+G251D+S273Y,
K19T+E83T+I96L+S164G+L222I+R242E+L253V,
K19T+I96L+S164G+R242E+L253I,
I96L+S164G+L222I+R242E+G251D,
K19T+I96L+S164N+L222I+R242E+I263L, and
K19T+D59N+E83T+S164G+L166V+L222I+R242D+
G251D.

4. A method of making an isolated chymosin polypeptide variant according to claim 1, comprising:
  (a) producing a chymosin polypeptide variant having an alteration at one or more positions in its amino acid sequence relative to the parent polypeptide, wherein the alteration results in a substitution at amino acid position S164 of the parent polypeptide; and
  (b) isolating the chymosin polypeptide variant of step (a), thereby obtaining the isolated chymosin polypeptide variant.

5. The method of claim 4, wherein the alteration is S164G.

6. A method for making a food or feed product, comprising adding an effective amount of the isolated chymosin polypeptide variant according to claim 1 to food or feed product ingredient(s).

7. The method of claim 6, wherein the food or feed product is a cheese.

8. The method of claim 6, wherein the food or feed product is a cheese selected from Pasta filata, Cheddar, Continental type cheeses, soft Cheese and White Brine Cheese.

9. A food or feed product comprising a chymosin polypeptide variant according to claim 1.

10. The isolated chymosin polypeptide variant of claim 1, having an additional alteration in its amino acid sequence relative to the parent polypeptide selected from a substitution, deletion, or insertion at one or more amino acid positions selected from L12, K19, V51, D59, R61, H76, E83, I96, L105, D144, Q162, M165, L166, L180, V203, L221, L222, S226, T239, R242, G251, L253, V260, I263, R266, S273, Q288, G289, E294, Y307, V309, R316, and V317 of the parent polypeptide, wherein the amino acid position of the parent polypeptide is determined by alignment of the parent polypeptide with the polypeptide of SEQ ID NO: 4.

11. The isolated chymosin polypeptide variant of claim 10, wherein the additional alteration comprises one or more substitutions selected from L12M, K19T, V51L, D59N, R61S, H76Q, E83S, I96L, L105E, D144Q, Q162S, M165E, L166V, L180I, V203A, L221I, L222V, L222I, S226T, T239S, R242E, G251D, G251W, L253I, V260T, I263L, R266V, S273Y, Q288E, G289S, E294Q, Y307F, V309I, R316L, and V317L.

12. The method of claim 4, wherein the variant has an additional alteration in its amino acid sequence relative to the parent polypeptide selected from a substitution, deletion, or insertion at one or more amino acid positions selected from L12, K19, V51, D59, R61, H76, E83, I96, L105, D144, Q162, M165, L166, L180, V203, L221, L222, S226, T239, R242, G251, L253, V260, I263, R266, S273, Q288, G289, E294, Y307, V309, R316, and V317 of the parent polypeptide, wherein the amino acid position of the parent polypeptide is determined by alignment of the parent polypeptide with the polypeptide of SEQ ID NO: 4.

13. The method of claim 12, wherein the additional alteration comprises one or more substitutions selected from L12M, K19T, V51L, D59N, R61S, H76Q, E83S, I96L, L105E, D144Q, Q162S, M165E, L166V, L180I, V203A, L221I, L222V, L222I, S226T, T239S, R242E, G251D, G251W, L253I, V260T, I263L, R266V, S273Y, Q288E, G289S, E294Q, Y307F, V309I, R316L, and V317L.

* * * * *

SEQUENCE LISTING

```
<160> NUMBER OF SEQ ID NOS: 4

<210> SEQ ID NO 1
<211> LENGTH: 381
<212> TYPE: PRT
<213> ORGANISM: Bos

<400> SEQUENCE: 1

Met Arg Cys Leu Val Val Leu Leu Ala Val Phe Ala Leu Ser Gln Gly
1               5                   10                  15

Ala Glu Ile Thr Arg Ile Pro Leu Tyr Lys Gly Lys Ser Leu Arg Lys
                20                  25                  30

Ala Leu Lys Glu His Gly Leu Leu Glu Asp Phe Leu Gln Lys Gln Gln
            35                  40                  45

Tyr Gly Ile Ser Ser Lys Tyr Ser Gly Phe Gly Glu Val Ala Ser Val
        50                  55                  60

Pro Leu Thr Asn Tyr Leu Asp Ser Gln Tyr Phe Gly Lys Ile Tyr Leu
65                  70                  75                  80

Gly Thr Pro Pro Gln Glu Phe Thr Val Leu Phe Asp Thr Gly Ser Ser
```

```
                         85                  90                  95
Asp Phe Trp Val Pro Ser Ile Tyr Cys Lys Ser Asn Ala Cys Lys Asn
                100                 105                 110

His Gln Arg Phe Asp Pro Arg Lys Ser Ser Thr Phe Gln Asn Leu Gly
            115                 120                 125

Lys Pro Leu Ser Ile His Tyr Gly Thr Gly Ser Met Gln Gly Ile Leu
        130                 135                 140

Gly Tyr Asp Thr Val Thr Val Ser Asn Ile Val Asp Ile Gln Gln Thr
145                 150                 155                 160

Val Gly Leu Ser Thr Gln Glu Pro Gly Asp Val Phe Thr Tyr Ala Glu
                165                 170                 175

Phe Asp Gly Ile Leu Gly Met Ala Tyr Pro Ser Leu Ala Ser Glu Tyr
            180                 185                 190

Ser Ile Pro Val Phe Asp Asn Met Met Asn Arg His Leu Val Ala Gln
        195                 200                 205

Asp Leu Phe Ser Val Tyr Met Asp Arg Asn Gly Gln Glu Ser Met Leu
    210                 215                 220

Thr Leu Gly Ala Ile Asp Pro Ser Tyr Tyr Thr Gly Ser Leu His Trp
225                 230                 235                 240

Val Pro Val Thr Val Gln Gln Tyr Trp Gln Phe Thr Val Asp Ser Val
                245                 250                 255

Thr Ile Ser Gly Val Val Ala Cys Glu Gly Gly Cys Gln Ala Ile
        260                 265                 270

Leu Asp Thr Gly Thr Ser Lys Leu Val Gly Pro Ser Ser Asp Ile Leu
    275                 280                 285

Asn Ile Gln Gln Ala Ile Gly Ala Thr Gln Asn Gln Tyr Gly Glu Phe
    290                 295                 300

Asp Ile Asp Cys Asp Asn Leu Ser Tyr Met Pro Thr Val Val Phe Glu
305                 310                 315                 320

Ile Asn Gly Lys Met Tyr Pro Leu Thr Pro Ser Ala Tyr Thr Ser Gln
                325                 330                 335

Asp Gln Gly Phe Cys Thr Ser Gly Phe Gln Ser Glu Asn His Ser Gln
            340                 345                 350

Lys Trp Ile Leu Gly Asp Val Phe Ile Arg Glu Tyr Tyr Ser Val Phe
        355                 360                 365

Asp Arg Ala Asn Asn Leu Val Gly Leu Ala Lys Ala Ile
    370                 375                 380

<210> SEQ ID NO 2
<211> LENGTH: 381
<212> TYPE: PRT
<213> ORGANISM: Camelus

<400> SEQUENCE: 2

Met Arg Cys Leu Val Val Leu Leu Ala Ala Leu Ala Leu Ser Gln Ala
1               5                   10                  15

Ser Gly Ile Thr Arg Ile Pro Leu His Lys Gly Lys Thr Leu Arg Lys
            20                  25                  30

Ala Leu Lys Glu Arg Gly Leu Leu Glu Asp Phe Leu Gln Arg Gln Gln
        35                  40                  45

Tyr Ala Val Ser Ser Lys Tyr Ser Ser Leu Gly Lys Val Ala Arg Glu
    50                  55                  60

Pro Leu Thr Ser Tyr Leu Asp Ser Gln Tyr Phe Gly Lys Ile Tyr Ile
65                  70                  75                  80
```

```
Gly Thr Pro Pro Gln Glu Phe Thr Val Val Phe Asp Thr Gly Ser Ser
                85                  90                  95

Asp Leu Trp Val Pro Ser Ile Tyr Cys Lys Ser Asn Val Cys Lys Asn
            100                 105                 110

His His Arg Phe Asp Pro Arg Lys Ser Ser Thr Phe Arg Asn Leu Gly
        115                 120                 125

Lys Pro Leu Ser Ile His Tyr Gly Thr Gly Ser Met Glu Gly Phe Leu
    130                 135                 140

Gly Tyr Asp Thr Val Thr Val Ser Asn Ile Val Asp Pro Asn Gln Thr
145                 150                 155                 160

Val Gly Leu Ser Thr Glu Gln Pro Gly Glu Val Phe Thr Tyr Ser Glu
                165                 170                 175

Phe Asp Gly Ile Leu Gly Leu Ala Tyr Pro Ser Leu Ala Ser Glu Tyr
            180                 185                 190

Ser Val Pro Val Phe Asp Asn Met Met Asp Arg His Leu Val Ala Arg
        195                 200                 205

Asp Leu Phe Ser Val Tyr Met Asp Arg Asn Gly Gln Gly Ser Met Leu
    210                 215                 220

Thr Leu Gly Ala Ile Asp Pro Ser Tyr Tyr Thr Gly Ser Leu His Trp
225                 230                 235                 240

Val Pro Val Thr Leu Gln Gln Tyr Trp Gln Phe Thr Val Asp Ser Val
                245                 250                 255

Thr Ile Asn Gly Val Ala Val Ala Cys Val Gly Gly Cys Gln Ala Ile
            260                 265                 270

Leu Asp Thr Gly Thr Ser Val Leu Phe Gly Pro Ser Ser Asp Ile Leu
        275                 280                 285

Lys Ile Gln Met Ala Ile Gly Ala Thr Glu Asn Arg Tyr Gly Glu Phe
    290                 295                 300

Asp Val Asn Cys Gly Asn Leu Arg Ser Met Pro Thr Val Val Phe Glu
305                 310                 315                 320

Ile Asn Gly Arg Asp Tyr Pro Leu Ser Pro Ser Ala Tyr Thr Ser Lys
                325                 330                 335

Asp Gln Gly Phe Cys Thr Ser Gly Phe Gln Gly Asp Asn Asn Ser Glu
            340                 345                 350

Leu Trp Ile Leu Gly Asp Val Phe Ile Arg Glu Tyr Tyr Ser Val Phe
        355                 360                 365

Asp Arg Ala Asn Asn Arg Val Gly Leu Ala Lys Ala Ile
    370                 375                 380

<210> SEQ ID NO 3
<211> LENGTH: 323
<212> TYPE: PRT
<213> ORGANISM: Bos

<400> SEQUENCE: 3

Gly Glu Val Ala Ser Val Pro Leu Thr Asn Tyr Leu Asp Ser Gln Tyr
1               5                   10                  15

Phe Gly Lys Ile Tyr Leu Gly Thr Pro Pro Gln Glu Phe Thr Val Leu
                20                  25                  30

Phe Asp Thr Gly Ser Ser Asp Phe Trp Val Pro Ser Ile Tyr Cys Lys
            35                  40                  45

Ser Asn Ala Cys Lys Asn His Gln Arg Phe Asp Pro Arg Lys Ser Ser
        50                  55                  60

Thr Phe Gln Asn Leu Gly Lys Pro Leu Ser Ile His Tyr Gly Thr Gly
65                  70                  75                  80
```

Ser Met Gln Gly Ile Leu Gly Tyr Asp Thr Val Thr Val Ser Asn Ile
            85                  90                  95

Val Asp Ile Gln Gln Thr Val Gly Leu Ser Thr Gln Glu Pro Gly Asp
            100                 105                 110

Val Phe Thr Tyr Ala Glu Phe Asp Gly Ile Leu Gly Met Ala Tyr Pro
            115                 120                 125

Ser Leu Ala Ser Glu Tyr Ser Ile Pro Val Phe Asp Asn Met Met Asn
        130                 135                 140

Arg His Leu Val Ala Gln Asp Leu Phe Ser Val Tyr Met Asp Arg Asn
145                 150                 155                 160

Gly Gln Glu Ser Met Leu Thr Leu Gly Ala Ile Asp Pro Ser Tyr Tyr
                165                 170                 175

Thr Gly Ser Leu His Trp Val Pro Val Thr Val Gln Gln Tyr Trp Gln
            180                 185                 190

Phe Thr Val Asp Ser Val Thr Ile Ser Gly Val Val Ala Cys Glu
            195                 200                 205

Gly Gly Cys Gln Ala Ile Leu Asp Thr Gly Thr Ser Lys Leu Val Gly
        210                 215                 220

Pro Ser Ser Asp Ile Leu Asn Ile Gln Gln Ala Ile Gly Ala Thr Gln
225                 230                 235                 240

Asn Gln Tyr Gly Glu Phe Asp Ile Asp Cys Asp Asn Leu Ser Tyr Met
                245                 250                 255

Pro Thr Val Val Phe Glu Ile Asn Gly Lys Met Tyr Pro Leu Thr Pro
            260                 265                 270

Ser Ala Tyr Thr Ser Gln Asp Gln Gly Phe Cys Thr Ser Gly Phe Gln
        275                 280                 285

Ser Glu Asn His Ser Gln Lys Trp Ile Leu Gly Asp Val Phe Ile Arg
290                 295                 300

Glu Tyr Tyr Ser Val Phe Asp Arg Ala Asn Asn Leu Val Gly Leu Ala
305                 310                 315                 320

Lys Ala Ile

<210> SEQ ID NO 4
<211> LENGTH: 323
<212> TYPE: PRT
<213> ORGANISM: Camelus

<400> SEQUENCE: 4

Gly Lys Val Ala Arg Glu Pro Leu Thr Ser Tyr Leu Asp Ser Gln Tyr
1               5                   10                  15

Phe Gly Lys Ile Tyr Ile Gly Thr Pro Pro Gln Glu Phe Thr Val Val
            20                  25                  30

Phe Asp Thr Gly Ser Ser Asp Leu Trp Val Pro Ser Ile Tyr Cys Lys
        35                  40                  45

Ser Asn Val Cys Lys Asn His His Arg Phe Asp Pro Arg Lys Ser Ser
    50                  55                  60

Thr Phe Arg Asn Leu Gly Lys Pro Leu Ser Ile His Tyr Gly Thr Gly
65                  70                  75                  80

Ser Met Glu Gly Phe Leu Gly Tyr Asp Thr Val Thr Ser Asn Ile
                85                  90                  95

Val Asp Pro Asn Gln Thr Val Gly Leu Ser Thr Glu Gln Pro Gly Glu
            100                 105                 110

Val Phe Thr Tyr Ser Glu Phe Asp Gly Ile Leu Gly Leu Ala Tyr Pro
            115                 120                 125

```
Ser Leu Ala Ser Glu Tyr Ser Val Pro Val Phe Asp Asn Met Met Asp
    130             135             140
Arg His Leu Val Ala Arg Asp Leu Phe Ser Val Tyr Met Asp Arg Asn
145             150             155             160
Gly Gln Gly Ser Met Leu Thr Leu Gly Ala Ile Asp Pro Ser Tyr Tyr
                165             170             175
Thr Gly Ser Leu His Trp Val Pro Val Thr Leu Gln Gln Tyr Trp Gln
            180             185             190
Phe Thr Val Asp Ser Val Thr Ile Asn Gly Val Ala Val Ala Cys Val
        195             200             205
Gly Gly Cys Gln Ala Ile Leu Asp Thr Gly Thr Ser Val Leu Phe Gly
    210             215             220
Pro Ser Ser Asp Ile Leu Lys Ile Gln Met Ala Ile Gly Ala Thr Glu
225             230             235             240
Asn Arg Tyr Gly Glu Phe Asp Val Asn Cys Gly Asn Leu Arg Ser Met
                245             250             255
Pro Thr Val Val Phe Glu Ile Asn Gly Arg Asp Tyr Pro Leu Ser Pro
            260             265             270
Ser Ala Tyr Thr Ser Lys Asp Gln Gly Phe Cys Thr Ser Gly Phe Gln
            275             280             285
Gly Asp Asn Asn Ser Glu Leu Trp Ile Leu Gly Asp Val Phe Ile Arg
    290             295             300
Glu Tyr Tyr Ser Val Phe Asp Arg Ala Asn Asn Arg Val Gly Leu Ala
305             310             315             320
Lys Ala Ile
```